United States Patent
Burns et al.

(10) Patent No.: US 10,828,195 B2
(45) Date of Patent: *Nov. 10, 2020

(54) UVEOSCLERAL SHUNT AND METHODS FOR IMPLANTING SAME

(71) Applicant: GLAUKOS CORPORATION, San Clemente, CA (US)

(72) Inventors: Thomas W. Burns, Dana Point, CA (US); David Haffner, Mission Viejo, CA (US); Harold A. Heitzmann, Irvine, CA (US); Todd N. Fjield, Laguna Hills, CA (US); Richard A. Hill, Irvine, CA (US)

(73) Assignee: Glaukos Corporation, San Clemente, CA (US)

( * ) Notice: Subject to any disclaimer, the term of this patent is extended or adjusted under 35 U.S.C. 154(b) by 301 days.

This patent is subject to a terminal disclaimer.

(21) Appl. No.: 15/971,553

(22) Filed: May 4, 2018

(65) Prior Publication Data
US 2018/0325732 A1    Nov. 15, 2018

Related U.S. Application Data

(63) Continuation of application No. 13/964,579, filed on Aug. 12, 2013, now Pat. No. 9,962,290, which is a
(Continued)

(51) Int. Cl.
A61F 9/007    (2006.01)

(52) U.S. Cl.
CPC ................. *A61F 9/00781* (2013.01)

(58) Field of Classification Search
CPC .. A61F 9/00781; A61F 9/00791; A61F 9/007; A61F 9/0017
See application file for complete search history.

(56) References Cited

U.S. PATENT DOCUMENTS

| 2,031,754 A | 2/1936 | Mills |
| 2,127,903 A | 8/1938 | Bowen |

(Continued)

FOREIGN PATENT DOCUMENTS

| AU | 200072059 A1 | 7/2001 |
| AU | 2004264913 | 12/2011 |

(Continued)

OTHER PUBLICATIONS

Bahler, Cindy K., BS, Gregrory T. Smedley, PhD, Jianbo Zhou, PhD, Douglas H. Johnson, MD., *Trabecular Bypass Stents Decrease Intraocular Pressure in Cultured Human Anterior Segments*, American Journal of Ophthalmology, Dec. 2004, vol. 138, pp. 988-994.

(Continued)

*Primary Examiner* — Philip R Wiest
(74) *Attorney, Agent, or Firm* — Knobbe Martens Olson & Bear LLP

(57) ABSTRACT

Devices and methods for treating intraocular pressure are disclosed. The devices include shunts for draining aqueous humor from the anterior chamber to the uveoscleral outflow pathway, including the supraciliary space and the suprachoroidal space. The shunts are preferably implanted by ab interno procedures.

20 Claims, 38 Drawing Sheets

Related U.S. Application Data continuation of application No. 11/938,238, filed on Nov. 9, 2007, now Pat. No. 8,506,515.

(60) Provisional application No. 60/947,942, filed on Jul. 3, 2007, provisional application No. 60/890,610, filed on Feb. 19, 2007, provisional application No. 60/880,091, filed on Jan. 11, 2007, provisional application No. 60/857,872, filed on Nov. 10, 2006.

(56) References Cited

U.S. PATENT DOCUMENTS

| | | |
|---|---|---|
| 2,269,963 A | 1/1942 | Frederick |
| 3,416,530 A | 12/1968 | Ness |
| 3,439,675 A | 4/1969 | Cohen |
| 3,717,151 A | 2/1973 | Collett |
| 3,788,327 A | 1/1974 | Donowitz et al. |
| 3,809,093 A | 5/1974 | Abraham |
| 3,827,700 A | 8/1974 | Kaller |
| 3,863,623 A | 2/1975 | Trueblood et al. |
| 3,915,172 A | 10/1975 | Krejci et al. |
| 3,948,271 A | 4/1976 | Aklyama |
| 3,948,871 A | 4/1976 | Butterfield et al. |
| 3,976,077 A | 8/1976 | Kerfoot, Jr. |
| 4,030,480 A | 6/1977 | Meyer |
| 4,037,604 A | 7/1977 | Newkirk |
| 4,043,346 A | 8/1977 | Mobley et al. |
| 4,113,088 A | 9/1978 | Binkhorst |
| 4,168,697 A | 9/1979 | Cantekin |
| 4,175,563 A | 11/1979 | Arenberg et al. |
| 4,299,227 A | 11/1981 | Lincoff |
| 4,328,803 A | 5/1982 | Pape |
| 4,366,582 A | 1/1983 | Faulkner |
| 4,402,681 A | 9/1983 | Haas et al. |
| 4,428,746 A | 1/1984 | Mendez |
| 4,449,529 A | 5/1984 | Burns et al. |
| 4,449,974 A | 5/1984 | Messingschlager |
| 4,501,274 A | 2/1985 | Skjaerpe |
| 4,521,210 A | 6/1985 | Wong |
| 4,554,918 A | 11/1985 | White |
| 4,560,383 A | 12/1985 | Leiske |
| 4,578,058 A | 3/1986 | Grandon |
| 4,583,224 A | 4/1986 | Ishii et al. |
| 4,604,087 A | 8/1986 | Joseph |
| 4,632,842 A | 12/1986 | Karwoski et al. |
| 4,634,418 A | 1/1987 | Binder |
| 4,642,090 A | 2/1987 | Ultrata |
| 4,692,142 A | 9/1987 | Dignam et al. |
| 4,718,907 A | 1/1988 | Karwoski et al. |
| 4,722,724 A | 2/1988 | Schocket |
| 4,733,665 A | 3/1988 | Palmaz |
| 4,750,901 A | 6/1988 | Molteno |
| 4,782,819 A | 11/1988 | Adair |
| 4,787,885 A | 11/1988 | Binder |
| 4,800,870 A | 1/1989 | Reid, Jr. |
| 4,800,890 A | 1/1989 | Cramer |
| 4,804,382 A | 2/1989 | Turina et al. |
| 4,820,626 A | 4/1989 | Williams et al. |
| 4,846,172 A | 7/1989 | Berlin |
| 4,846,793 A | 7/1989 | Leonard et al. |
| 4,853,224 A | 8/1989 | Wong |
| 4,863,457 A | 9/1989 | Lee |
| 4,867,173 A | 9/1989 | Leoni |
| 4,870,953 A | 10/1989 | DonMicheal et al. |
| 4,883,864 A | 11/1989 | Scholz |
| 4,886,488 A | 12/1989 | White |
| 4,900,300 A | 2/1990 | Lee |
| 4,905,667 A | 3/1990 | Foerster et al. |
| 4,936,825 A | 6/1990 | Ungerleider |
| 4,946,436 A | 8/1990 | Smith |
| 4,968,296 A | 11/1990 | Ritch et al. |
| 4,986,810 A | 1/1991 | Semrad |
| 4,991,602 A | 2/1991 | Amplatz et al. |
| 4,997,652 A | 3/1991 | Wong |
| 5,005,577 A | 4/1991 | Frenekl |
| 5,041,081 A | 8/1991 | Odrich |
| 5,053,040 A | 10/1991 | Goldsmith, III |
| 5,053,044 A | 10/1991 | Mueller et al. |
| 5,073,163 A | 12/1991 | Lippman |
| 5,092,837 A | 3/1992 | Ritch et al. |
| 5,095,887 A | 3/1992 | Leon et al. |
| 5,116,327 A | 5/1992 | Seder et al. |
| 5,127,901 A | 7/1992 | Odrich |
| 5,129,895 A | 7/1992 | Vassiliadis et al. |
| 5,139,502 A | 8/1992 | Berg et al. |
| 5,164,188 A | 11/1992 | Wong |
| 5,169,386 A | 12/1992 | Becker et al. |
| 5,171,213 A | 12/1992 | Price, Jr. |
| 5,178,604 A | 1/1993 | Baerveldt et al. |
| 5,180,362 A | 1/1993 | Worst |
| 5,207,685 A | 5/1993 | Cinberg et al. |
| 5,221,255 A | 6/1993 | Mahurkar et al. |
| 5,246,451 A | 9/1993 | Trescony et al. |
| 5,248,231 A | 9/1993 | Denham et al. |
| 5,284,476 A | 2/1994 | Koch |
| 5,290,295 A | 3/1994 | Querals et al. |
| 5,300,020 A | 4/1994 | L'Esperance, Jr. |
| 5,318,513 A | 6/1994 | Leib et al. |
| 5,324,306 A | 6/1994 | Makower et al. |
| 5,334,137 A | 8/1994 | Freeman |
| 5,338,291 A | 8/1994 | Speckman et al. |
| 5,342,370 A | 8/1994 | Simon et al. |
| 5,346,464 A | 9/1994 | Camras |
| 5,358,492 A | 10/1994 | Feibus |
| 5,360,399 A | 11/1994 | Stegmann |
| 5,370,607 A | 12/1994 | Memmen |
| 5,370,641 A | 12/1994 | O'Donnell, Jr. |
| 5,372,577 A | 12/1994 | Ungerleider |
| 5,397,300 A | 3/1995 | Baerveldt et al. |
| 5,409,457 A | 4/1995 | del Cerro et al. |
| 5,415,666 A | 5/1995 | Gourlay et al. |
| 5,433,701 A | 7/1995 | Rubinstein |
| 5,443,505 A | 8/1995 | Wong et al. |
| 5,445,637 A | 8/1995 | Bretton |
| 5,454,796 A | 10/1995 | Krupin |
| 5,462,558 A | 10/1995 | Kolesa et al. |
| 5,472,440 A | 12/1995 | Beckman |
| 5,476,445 A | 12/1995 | Baerveldt et al. |
| 5,486,165 A | 1/1996 | Stegmann |
| 5,502,052 A | 3/1996 | DeSantis |
| 5,516,522 A | 5/1996 | Peyman et al. |
| 5,520,631 A | 5/1996 | Nordquist et al. |
| 5,547,993 A | 8/1996 | Miki |
| 5,556,400 A | 9/1996 | Tunis |
| 5,557,453 A | 9/1996 | Schalz et al. |
| 5,558,629 A | 9/1996 | Baerveldt et al. |
| 5,558,630 A | 9/1996 | Fisher |
| 5,558,637 A | 9/1996 | Allonen et al. |
| 5,562,641 A | 10/1996 | Flomenblit et al. |
| RE35,390 E | 12/1996 | Smith |
| 5,601,094 A | 2/1997 | Reiss |
| 5,601,549 A | 2/1997 | Miyagi |
| 5,626,558 A | 5/1997 | Suson |
| 5,626,559 A | 5/1997 | Solomon |
| 5,626,588 A | 5/1997 | Sauer et al. |
| 5,639,278 A | 6/1997 | Dereume et al. |
| 5,643,321 A | 7/1997 | McDevitt |
| 5,651,782 A | 7/1997 | Simon et al. |
| 5,651,783 A | 7/1997 | Reynard |
| 5,652,236 A | 7/1997 | Krauss |
| 5,653,724 A | 8/1997 | Imonti |
| 5,663,205 A | 9/1997 | Ogawa et al. |
| 5,665,114 A | 9/1997 | Weadock et al. |
| 5,669,501 A | 9/1997 | Hissong et al. |
| 5,670,161 A | 9/1997 | Healy et al. |
| 5,676,679 A | 10/1997 | Simon et al. |
| 5,681,275 A | 10/1997 | Ahmed |
| 5,681,323 A | 10/1997 | Arick |
| 5,695,479 A | 12/1997 | Jagpal |
| 5,702,414 A | 12/1997 | Richter et al. |
| 5,702,419 A | 12/1997 | Berry et al. |
| 5,704,907 A | 1/1998 | Nordquist et al. |
| 5,713,844 A | 2/1998 | Peyman |
| 5,723,005 A | 3/1998 | Herrick |

(56) References Cited

U.S. PATENT DOCUMENTS

| | | |
|---|---|---|
| 5,725,493 A | 3/1998 | Avery et al. |
| 5,725,529 A | 3/1998 | Nicholson et al. |
| 5,725,546 A | 3/1998 | Samson |
| 5,733,256 A | 3/1998 | Costin |
| 5,741,292 A | 4/1998 | Mendius |
| 5,741,333 A | 4/1998 | Frid |
| 5,743,868 A | 4/1998 | Brown et al. |
| 5,752,928 A | 5/1998 | de Roulhac et al. |
| 5,762,625 A | 6/1998 | Igaki |
| 5,766,242 A | 6/1998 | Wong et al. |
| 5,766,243 A | 6/1998 | Christensen et al. |
| 5,767,079 A | 6/1998 | Glaser et al. |
| 5,785,674 A | 7/1998 | Mateen |
| 5,792,099 A | 8/1998 | DeCamp et al. |
| 5,800,376 A | 9/1998 | Vaskelis |
| 5,807,244 A | 9/1998 | Barot |
| 5,807,302 A | 9/1998 | Wandel |
| 5,810,870 A | 9/1998 | Myers et al. |
| 5,814,620 A | 9/1998 | Robinson et al. |
| 5,817,100 A | 10/1998 | Igaki |
| 5,824,071 A | 10/1998 | Nelson et al. |
| 5,824,072 A | 10/1998 | Wong |
| 5,830,139 A | 11/1998 | Abrue |
| 5,830,171 A | 11/1998 | Wallace |
| 5,833,694 A | 11/1998 | Poncet |
| 5,836,939 A | 11/1998 | Negus et al. |
| 5,840,041 A | 11/1998 | Petter et al. |
| 5,846,199 A | 12/1998 | Hijlkema et al. |
| 5,865,831 A | 2/1999 | Cozean et al. |
| 5,868,697 A | 2/1999 | Richter et al. |
| 5,869,468 A | 2/1999 | Freeman |
| 5,879,319 A | 3/1999 | Pynson et al. |
| 5,882,327 A | 3/1999 | Jacob |
| 5,886,822 A | 3/1999 | Spitzer |
| 5,891,084 A | 4/1999 | Lee |
| 5,893,837 A | 4/1999 | Eagles et al. |
| 5,908,449 A | 6/1999 | Bruchman et al. |
| 5,913,852 A | 6/1999 | Magram |
| 5,925,342 A | 7/1999 | Adorante et al. |
| 5,927,585 A | 7/1999 | Moorman et al. |
| 5,932,299 A | 8/1999 | Katoot |
| 5,941,250 A | 8/1999 | Aramant et al. |
| 5,952,378 A | 9/1999 | Stjerschantz et al. |
| 5,968,058 A | 10/1999 | Richter et al. |
| 5,980,928 A | 11/1999 | Terry |
| 5,981,598 A | 11/1999 | Tatton |
| 5,984,913 A | 11/1999 | Kritzinger et al. |
| 6,004,302 A | 12/1999 | Brierley |
| 6,007,510 A | 12/1999 | Nigam |
| 6,007,511 A | 12/1999 | Prywes |
| 6,030,416 A | 2/2000 | Huo et al. |
| 6,033,434 A | 3/2000 | Borghi |
| 6,036,678 A | 3/2000 | Giungo |
| 6,036,682 A | 3/2000 | Lange et al. |
| 6,045,557 A | 4/2000 | White et al. |
| 6,050,970 A | 4/2000 | Baeverldt |
| 6,050,999 A | 4/2000 | Paraschac et al. |
| 6,059,772 A | 5/2000 | Hsia et al. |
| 6,059,812 A | 5/2000 | Clerc et al. |
| 6,060,463 A | 5/2000 | Freeman |
| 6,063,116 A | 5/2000 | Kelleher |
| 6,063,396 A | 5/2000 | Kelleher |
| 6,071,286 A | 6/2000 | Mawad |
| 6,074,395 A | 6/2000 | Trott et al. |
| 6,077,299 A | 6/2000 | Adelberg et al. |
| 6,102,045 A | 8/2000 | Nordquist et al. |
| 6,110,912 A | 8/2000 | Kaufman et al. |
| 6,123,668 A | 9/2000 | Abreu |
| 6,135,977 A | 10/2000 | Drasler et al. |
| 6,142,990 A | 11/2000 | Burk |
| 6,146,387 A | 11/2000 | Trott et al. |
| 6,159,458 A | 12/2000 | Bowman et al. |
| 6,165,210 A | 12/2000 | Lau et al. |
| 6,168,575 B1 | 1/2001 | Soltanpour |
| 6,174,305 B1 | 1/2001 | Mikus et al. |
| 6,177,427 B1 | 1/2001 | Clark et al. |
| 6,184,250 B1 | 2/2001 | Klimko et al. |
| 6,186,974 B1 | 2/2001 | Allan et al. |
| 6,187,016 B1 | 2/2001 | Hedges et al. |
| 6,193,656 B1 | 2/2001 | Jeffries et al. |
| 6,194,415 B1 | 2/2001 | Wheeler et al. |
| 6,197,056 B1 | 3/2001 | Schachar |
| 6,201,001 B1 | 3/2001 | Wang et al. |
| 6,203,513 B1 | 3/2001 | Yaron et al. |
| 6,217,895 B1 | 4/2001 | Guo et al. |
| 6,221,078 B1 | 4/2001 | Bylsma |
| 6,224,570 B1 | 5/2001 | Le et al. |
| 6,228,873 B1 | 5/2001 | Brandt et al. |
| 6,231,597 B1 | 5/2001 | Deem et al. |
| 6,231,853 B1 | 5/2001 | Hillman et al. |
| 6,241,721 B1 | 6/2001 | Cozean et al. |
| 6,251,090 B1 | 6/2001 | Avery et al. |
| 6,254,612 B1 | 7/2001 | Hieshima |
| 6,261,256 B1 | 7/2001 | Ahmed |
| 6,264,668 B1 | 7/2001 | Prywes |
| 6,266,182 B1 | 7/2001 | Morita |
| 6,268,398 B1 | 7/2001 | Ghosh et al. |
| 6,274,138 B1 | 8/2001 | Bandman et al. |
| 6,287,256 B1 | 9/2001 | Park et al. |
| 6,287,313 B1 | 9/2001 | Sasso |
| 6,299,603 B1 | 10/2001 | Hecker et al. |
| 6,299,895 B1 | 10/2001 | Hammang et al. |
| 6,306,114 B1 | 10/2001 | Freeman et al. |
| 6,331,313 B1 | 12/2001 | Wong et al. |
| 6,342,058 B1 | 1/2002 | Portney |
| 6,348,042 B1 | 2/2002 | Warren, Jr. |
| 6,355,033 B1 | 3/2002 | Moorman et al. |
| 6,358,222 B1 | 3/2002 | Grundei |
| 6,361,519 B1 | 3/2002 | Knudson et al. |
| 6,363,938 B2 | 4/2002 | Saadat et al. |
| 6,375,642 B1 | 4/2002 | Grieshaber et al. |
| 6,378,526 B1 | 4/2002 | Bowman |
| 6,402,734 B1 | 6/2002 | Weiss |
| 6,405,732 B1 | 6/2002 | Edwards et al. |
| 6,413,540 B1 | 7/2002 | Yaacobi |
| 6,416,777 B1 | 7/2002 | Yaacobi |
| 6,428,501 B1 | 8/2002 | Reynard |
| 6,428,566 B1 | 8/2002 | Holt |
| 6,436,427 B1 | 8/2002 | Hammang et al. |
| 6,450,937 B1 | 9/2002 | Mercereau et al. |
| 6,450,984 B1 | 9/2002 | Lynch et al. |
| 6,454,787 B1 | 9/2002 | Maddalo et al. |
| 6,464,724 B1 | 10/2002 | Lynch et al. |
| 6,471,666 B1 | 10/2002 | Odrich |
| 6,494,857 B1 | 12/2002 | Neuhann |
| 6,510,600 B2 | 1/2003 | Yaron et al. |
| 6,517,483 B2 | 2/2003 | Park et al. |
| 6,524,275 B1 | 2/2003 | Lynch et al. |
| 6,530,896 B1 | 3/2003 | Elliott |
| 6,533,768 B1 | 3/2003 | Hill |
| 6,544,249 B1 | 4/2003 | Yu et al. |
| 6,548,078 B2 | 4/2003 | Guo et al. |
| 6,558,342 B1 | 5/2003 | Yaron et al. |
| 6,561,974 B1 | 5/2003 | Grieshaber et al. |
| 6,579,235 B1 | 6/2003 | Abita et al. |
| 6,582,426 B2 | 6/2003 | Moorman et al. |
| 6,582,453 B1 | 6/2003 | Tran et al. |
| 6,585,680 B2 | 7/2003 | Bugge |
| 6,585,753 B2 | 7/2003 | Eder et al. |
| 6,589,198 B1 | 7/2003 | Soltanpour et al. |
| 6,589,203 B1 | 7/2003 | Mitrev |
| 6,595,945 B2 | 7/2003 | Brown |
| 6,605,053 B1 | 8/2003 | Kamm et al. |
| 6,607,542 B1 | 8/2003 | Wild |
| 6,613,343 B2 | 9/2003 | Dillingham et al. |
| 6,620,154 B1 | 9/2003 | Amirkhanian et al. |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,841 B2 | 12/2003 | Gharib et al. |
| 6,676,607 B2 | 1/2004 | De Juan, Jr. et al. |
| 6,682,500 B2 | 1/2004 | Soltanpour et al. |
| 6,699,211 B2 | 3/2004 | Savage |
| 6,699,272 B2 | 3/2004 | Slepian et al. |

(56) References Cited

U.S. PATENT DOCUMENTS

| | | |
|---|---|---|
| 6,726,664 B2 | 4/2004 | Yaron et al. |
| 6,726,676 B2 | 4/2004 | Stegmann et al. |
| D490,152 S | 5/2004 | Myall et al. |
| 6,736,791 B1 | 5/2004 | Tu et al. |
| 6,763,833 B1 | 7/2004 | Khera et al. |
| 6,764,439 B2 | 7/2004 | Schaaf et al. |
| 6,767,346 B2 | 7/2004 | Damasco et al. |
| 6,780,164 B2 | 8/2004 | Bergheim et al. |
| 6,780,165 B2 | 8/2004 | Kadziauskas et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,827,738 B2 | 12/2004 | Willis et al. |
| 6,893,413 B2 | 5/2005 | Martin |
| 6,902,577 B2 | 6/2005 | Lipshitz et al. |
| 6,955,656 B2 | 10/2005 | Bergheim et al. |
| 6,966,888 B2 | 11/2005 | Cullen et al. |
| 6,969,384 B2 | 11/2005 | De Juan, Jr. et al. |
| 6,981,958 B1 | 1/2006 | Gharib et al. |
| 7,033,603 B2 | 4/2006 | Nelson et al. |
| 7,041,077 B2 | 5/2006 | Shields |
| 7,077,821 B2 | 7/2006 | Durgin |
| 7,077,848 B1 | 7/2006 | de Juan et al. |
| 7,090,681 B2 | 8/2006 | Weber et al. |
| 7,094,225 B2 | 8/2006 | Tu et al. |
| 7,101,402 B2 | 9/2006 | Phelps et al. |
| 7,135,009 B2 | 11/2006 | Tu et al. |
| 7,135,016 B1 | 11/2006 | Asia et al. |
| 7,144,616 B1 | 12/2006 | Unger et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,192,484 B2 | 3/2007 | Chappa et al. |
| 7,217,263 B2 | 5/2007 | Humayun et al. |
| 7,220,238 B2 | 5/2007 | Lynch et al. |
| 7,273,475 B2 | 9/2007 | Tu et al. |
| 7,291,125 B2 | 11/2007 | Coroneo |
| 7,294,115 B1 | 11/2007 | Wilk |
| 7,297,130 B2 | 11/2007 | Bergheim et al. |
| 7,331,984 B2 | 2/2008 | Tu et al. |
| 7,344,528 B1 | 3/2008 | Tu et al. |
| 7,431,710 B2 | 10/2008 | Tu et al. |
| 7,458,953 B2 | 12/2008 | Peyman |
| 7,468,065 B2 | 12/2008 | Weber et al. |
| 7,488,303 B1 | 2/2009 | Haffner et al. |
| 7,520,876 B2 | 4/2009 | Ressemann et al. |
| D592,746 S | 5/2009 | Highley et al. |
| RE40,722 E | 6/2009 | Chappa |
| 7,563,241 B2 | 7/2009 | Tu et al. |
| D606,190 S | 12/2009 | Pruitt et al. |
| 7,662,123 B2 | 2/2010 | Shields |
| 7,678,065 B2 | 3/2010 | Haffner et al. |
| 7,708,711 B2 | 5/2010 | Tu et al. |
| 7,713,228 B2 | 5/2010 | Robin |
| 7,758,624 B2 | 7/2010 | Dorn et al. |
| 7,771,388 B2 | 8/2010 | Olsen et al. |
| 7,815,592 B2 | 10/2010 | Coroneo |
| 7,850,637 B2 | 12/2010 | Lynch et al. |
| 7,850,638 B2 | 12/2010 | Coroneo |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,905,904 B2 | 3/2011 | Stone et al. |
| 7,931,660 B2 | 4/2011 | Aranyi et al. |
| 7,945,336 B2 | 5/2011 | Sauter-Starace et al. |
| 7,959,632 B2 | 6/2011 | Fugo |
| 7,967,772 B2 | 6/2011 | McKenzie et al. |
| 7,997,460 B2 | 8/2011 | Pardes et al. |
| 8,007,459 B2 | 8/2011 | Haffner et al. |
| 8,062,244 B2 | 11/2011 | Tu et al. |
| 8,075,511 B2 | 12/2011 | Tu et al. |
| 8,118,768 B2 | 2/2012 | Tu et al. |
| 8,142,364 B2 | 3/2012 | Haffner et al. |
| 8,197,418 B2 | 6/2012 | Lal et al. |
| 8,267,882 B2 | 9/2012 | Euteneuer et al. |
| 8,273,050 B2 | 9/2012 | Bergheim et al. |
| 8,333,742 B2 | 12/2012 | Bergheim et al. |
| 8,337,445 B2 | 12/2012 | Tu et al. |
| 8,348,877 B2 | 1/2013 | Tu et al. |
| 8,419,673 B2 | 4/2013 | Rickard |
| 8,506,515 B2 * | 8/2013 | Burns ..................... A61P 27/06 604/8 |
| 8,540,659 B2 | 9/2013 | Berlin |
| 8,545,431 B2 | 10/2013 | Rickard |
| 8,579,846 B2 | 11/2013 | Tu et al. |
| 8,579,848 B2 | 11/2013 | Field et al. |
| 8,585,664 B2 | 11/2013 | Dos Santos et al. |
| 8,603,024 B2 | 12/2013 | Bohm et al. |
| 8,617,094 B2 | 12/2013 | Smedley et al. |
| 8,656,958 B2 | 2/2014 | Unger et al. |
| 8,679,089 B2 | 3/2014 | Berlin |
| 8,721,580 B2 | 5/2014 | Rickard et al. |
| 8,753,305 B2 | 6/2014 | Field et al. |
| 8,771,220 B2 | 7/2014 | Nissan |
| 8,801,648 B2 | 8/2014 | Bergheim et al. |
| 8,808,219 B2 | 8/2014 | Bergheim et al. |
| 8,808,220 B2 | 8/2014 | Coroneo |
| 8,808,224 B2 | 8/2014 | Rickard |
| 8,814,820 B2 | 8/2014 | Bergheim et al. |
| 8,840,578 B2 | 9/2014 | Dos Santos et al. |
| 8,852,137 B2 | 10/2014 | Horvath et al. |
| 8,852,266 B2 | 10/2014 | Brooks et al. |
| 8,864,701 B2 | 10/2014 | Dos Santos et al. |
| 8,956,320 B2 | 2/2015 | Ovchinnikov et al. |
| 8,986,240 B2 | 3/2015 | Dos Santos et al. |
| 8,998,838 B2 | 4/2015 | Yalamanchili |
| 8,998,983 B2 | 4/2015 | Auld |
| 9,066,782 B2 | 6/2015 | Tu et al. |
| 9,072,588 B2 | 7/2015 | Bohm et al. |
| 9,125,721 B2 | 9/2015 | Field |
| 9,132,034 B2 | 9/2015 | Dos Santos |
| 9,155,653 B2 | 10/2015 | Field |
| 9,155,654 B2 | 10/2015 | Tu et al. |
| 9,173,775 B2 | 11/2015 | Haffner et al. |
| 9,220,632 B2 | 12/2015 | Smedley et al. |
| 9,226,851 B2 | 1/2016 | Gunn |
| 9,283,115 B2 | 3/2016 | Lind et al. |
| 9,289,324 B2 | 3/2016 | Johnson et al. |
| 9,301,875 B2 | 4/2016 | Tu et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,585,789 B2 * | 3/2017 | Silvestrini ........... A61F 9/00781 |
| 9,592,151 B2 | 3/2017 | Rangel-Friedman et al. |
| 9,597,230 B2 | 3/2017 | Haffner et al. |
| 9,603,738 B2 | 3/2017 | Haffner et al. |
| 9,603,741 B2 | 3/2017 | Berlin |
| 9,636,255 B2 | 5/2017 | Haffner et al. |
| 9,668,915 B2 | 6/2017 | Haffner et al. |
| 9,833,357 B2 | 12/2017 | Berlin |
| 9,849,027 B2 | 12/2017 | Highley et al. |
| 9,962,290 B2 * | 5/2018 | Burns ................. A61F 9/00781 |
| 9,987,472 B2 | 6/2018 | Tu et al. |
| 9,993,368 B2 | 6/2018 | Bergheim et al. |
| 10,188,551 B2 | 1/2019 | Rangel-Friedman et al. |
| 10,206,813 B2 | 2/2019 | Haffner et al. |
| 10,271,989 B2 | 4/2019 | Haffner et al. |
| 10,406,029 B2 | 9/2019 | Tu et al. |
| 10,485,701 B2 | 11/2019 | Haffner et al. |
| 10,492,950 B2 | 12/2019 | Lynch et al. |
| 10,517,759 B2 | 12/2019 | Crimaldi et al. |
| 2001/0000527 A1 | 4/2001 | Yaron et al. |
| 2001/0025150 A1 | 9/2001 | de Juan et al. |
| 2001/0053873 A1 | 12/2001 | Schaaf et al. |
| 2002/0013546 A1 | 1/2002 | Grieshaber et al. |
| 2002/0013572 A1 | 1/2002 | Berlin |
| 2002/0026200 A1 | 2/2002 | Savage |
| 2002/0052640 A1 | 5/2002 | Bigus et al. |
| 2002/0072673 A1 | 6/2002 | Yamamoto et al. |
| 2002/0099434 A1 | 7/2002 | Buscemi et al. |
| 2002/0111608 A1 | 8/2002 | Baerveldt et al. |
| 2002/0120284 A1 | 8/2002 | Schachar et al. |

(56) References Cited

U.S. PATENT DOCUMENTS

| | | |
|---|---|---|
| 2002/0120285 A1 | 8/2002 | Schachar et al. |
| 2002/0133168 A1 | 9/2002 | Smedley et al. |
| 2002/0143284 A1 | 10/2002 | Tu et al. |
| 2002/0165522 A1 | 11/2002 | Holmen |
| 2002/0177856 A1 | 11/2002 | Richter et al. |
| 2002/0188308 A1 | 12/2002 | Tu et al. |
| 2003/0014021 A1 | 1/2003 | Holmen |
| 2003/0014092 A1 | 1/2003 | Neuhann |
| 2003/0019833 A1 | 1/2003 | Unger et al. |
| 2003/0055372 A1 | 3/2003 | Lynch et al. |
| 2003/0060752 A1 | 3/2003 | Bergheim et al. |
| 2003/0069637 A1 | 4/2003 | Lynch et al. |
| 2003/0079329 A1 | 5/2003 | Yaron et al. |
| 2003/0088260 A1 | 5/2003 | Smedley et al. |
| 2003/0093084 A1 | 5/2003 | Nissan et al. |
| 2003/0097117 A1 | 5/2003 | Buono |
| 2003/0097151 A1 | 5/2003 | Smedley et al. |
| 2003/0105456 A1 | 6/2003 | Lin |
| 2003/0109907 A1 | 6/2003 | Shadduck |
| 2003/0135149 A1 | 7/2003 | Cullen et al. |
| 2003/0139729 A1 | 7/2003 | Stegmann et al. |
| 2003/0181848 A1 | 9/2003 | Bergheim et al. |
| 2003/0187384 A1 | 10/2003 | Bergheim et al. |
| 2003/0187385 A1 | 10/2003 | Bergheim et al. |
| 2003/0195438 A1 | 10/2003 | Petillo |
| 2003/0208163 A1 | 11/2003 | Yaron et al. |
| 2003/0208217 A1 | 11/2003 | Dan |
| 2003/0212383 A1 | 11/2003 | Cote et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0050392 A1 | 3/2004 | Tu et al. |
| 2004/0088048 A1 | 5/2004 | Richter et al. |
| 2004/0098122 A1 | 5/2004 | Lee et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0154946 A1 | 8/2004 | Solovay et al. |
| 2004/0193095 A1 | 9/2004 | Shadduck |
| 2004/0193262 A1 | 9/2004 | Shadduck |
| 2004/0215126 A1 | 10/2004 | Ahmed |
| 2004/0225250 A1 | 11/2004 | Yablonski |
| 2004/0236343 A1 | 11/2004 | Taylor et al. |
| 2004/0243227 A1 | 12/2004 | Starksen et al. |
| 2004/0249404 A1 | 12/2004 | Haefliger |
| 2004/0254517 A1 | 12/2004 | Quiroz-Mercado et al. |
| 2004/0254520 A1 | 12/2004 | Porteous et al. |
| 2004/0254521 A1 | 12/2004 | Simon |
| 2004/0260227 A1 | 12/2004 | Lisk, Jr. et al. |
| 2005/0038334 A1 | 2/2005 | Lynch et al. |
| 2005/0038498 A1 | 2/2005 | Dubrow et al. |
| 2005/0049578 A1 | 3/2005 | Tu et al. |
| 2005/0055075 A1 | 3/2005 | Pinchuk et al. |
| 2005/0096639 A1 | 5/2005 | Slatkine et al. |
| 2005/0107734 A1 | 5/2005 | Coroneo |
| 2005/0119737 A1 | 6/2005 | Bene et al. |
| 2005/0125003 A1 | 6/2005 | Pinchuk et al. |
| 2005/0165385 A1 | 7/2005 | Simon |
| 2005/0171562 A1 | 8/2005 | Criscuolo et al. |
| 2005/0192527 A1 | 9/2005 | Gharib et al. |
| 2005/0209549 A1 | 9/2005 | Bergheim et al. |
| 2005/0209672 A1 | 9/2005 | George et al. |
| 2005/0240143 A1 | 10/2005 | Dohlman |
| 2005/0240222 A1 | 10/2005 | Shipp |
| 2005/0250788 A1 | 11/2005 | Tu et al. |
| 2005/0267478 A1 | 12/2005 | Corradi et al. |
| 2005/0271704 A1 | 12/2005 | Tu et al. |
| 2005/0277864 A1 | 12/2005 | Haffner et al. |
| 2006/0032507 A1 | 2/2006 | Tu |
| 2006/0069340 A1 | 3/2006 | Simon |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0155238 A1 | 7/2006 | Shields |
| 2006/0155300 A1 | 7/2006 | Stamper et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0210605 A1 | 9/2006 | Chang et al. |
| 2006/0217741 A1 | 9/2006 | Ghannoum |
| 2006/0241580 A1 | 10/2006 | Mittelstein et al. |
| 2006/0241749 A1 | 10/2006 | Tu et al. |
| 2007/0004998 A1 | 1/2007 | Rodgers et al. |
| 2007/0021653 A1 | 1/2007 | Hattenbach et al. |
| 2007/0073275 A1 | 3/2007 | Conston et al. |
| 2007/0073390 A1 | 3/2007 | Lee |
| 2007/0078471 A1 | 4/2007 | Schachar et al. |
| 2007/0088242 A1 | 4/2007 | Coroneo |
| 2007/0093740 A1 | 4/2007 | Shetty |
| 2007/0106199 A1 | 5/2007 | Krivoy et al. |
| 2007/0106235 A1 | 5/2007 | Coroneo |
| 2007/0106236 A1 | 5/2007 | Coroneo |
| 2007/0118065 A1 | 5/2007 | Pinchuk et al. |
| 2007/0118066 A1 | 5/2007 | Pinchuk et al. |
| 2007/0123812 A1 | 5/2007 | Pinchuk et al. |
| 2007/0123919 A1 | 5/2007 | Schachar et al. |
| 2007/0149915 A1 | 6/2007 | Yablonski |
| 2007/0149927 A1 | 6/2007 | Itou et al. |
| 2007/0154621 A1 | 7/2007 | Raad |
| 2007/0156079 A1 | 7/2007 | Brown |
| 2007/0161981 A1 | 7/2007 | Sanders et al. |
| 2007/0179426 A1 | 8/2007 | Selden |
| 2007/0179471 A1 | 8/2007 | Christian et al. |
| 2007/0191863 A1 | 8/2007 | De Juan et al. |
| 2007/0202186 A1 | 8/2007 | Yamamoto et al. |
| 2007/0207186 A1 | 9/2007 | Scanlon et al. |
| 2007/0212386 A1 | 9/2007 | Patravale et al. |
| 2007/0212387 A1 | 9/2007 | Patravale et al. |
| 2007/0212388 A1 | 9/2007 | Patravale et al. |
| 2007/0212393 A1 | 9/2007 | Patravale et al. |
| 2007/0233037 A1 | 10/2007 | Gifford, III et al. |
| 2007/0276315 A1 | 11/2007 | Haffner |
| 2007/0276316 A1 | 11/2007 | Haffner |
| 2007/0282244 A1 | 12/2007 | Tu et al. |
| 2007/0287958 A1 | 12/2007 | McKenzie et al. |
| 2007/0292470 A1 | 12/2007 | Thornton |
| 2007/0293807 A1 | 12/2007 | Lynch et al. |
| 2007/0293873 A1 | 12/2007 | Chang |
| 2008/0027304 A1 | 1/2008 | Pardo et al. |
| 2008/0033351 A1 | 2/2008 | Trogden et al. |
| 2008/0039931 A1 | 2/2008 | Jelle et al. |
| 2008/0045878 A1 | 2/2008 | Bergheim et al. |
| 2008/0051681 A1 | 2/2008 | Schwartz |
| 2008/0058704 A1 | 3/2008 | Hee et al. |
| 2008/0082078 A1 | 4/2008 | Berlin |
| 2008/0091224 A1 | 4/2008 | Griffis, III et al. |
| 2008/0097214 A1 | 4/2008 | Meyers et al. |
| 2008/0097335 A1 | 4/2008 | Trogden et al. |
| 2008/0108932 A1 | 5/2008 | Rodgers |
| 2008/0108933 A1 | 5/2008 | Yu et al. |
| 2008/0109037 A1 | 5/2008 | Steiner et al. |
| 2008/0114440 A1 | 5/2008 | Hlavka et al. |
| 2008/0125691 A1 | 5/2008 | Yaron et al. |
| 2008/0140059 A1 | 6/2008 | Schachar et al. |
| 2008/0147083 A1 | 6/2008 | Vold et al. |
| 2008/0161907 A1 | 7/2008 | Chen et al. |
| 2008/0183289 A1 | 7/2008 | Werblin |
| 2008/0188860 A1 | 8/2008 | Vold |
| 2008/0195027 A1 | 8/2008 | Coroneo |
| 2008/0200860 A1 | 8/2008 | Tu et al. |
| 2008/0200923 A1 | 8/2008 | Beckman et al. |
| 2008/0208176 A1 | 8/2008 | Loh |
| 2008/0210322 A1 | 9/2008 | Unger et al. |
| 2008/0215062 A1 | 9/2008 | Bowen et al. |
| 2008/0221501 A1 | 9/2008 | Cote et al. |
| 2008/0228127 A1 | 9/2008 | Burns et al. |
| 2008/0236669 A1 | 10/2008 | Unger et al. |
| 2008/0243156 A1 | 10/2008 | John |
| 2008/0243243 A1 | 10/2008 | Williams et al. |
| 2008/0255545 A1 | 10/2008 | Mansfield et al. |

(56) References Cited

U.S. PATENT DOCUMENTS

| | | |
|---|---|---|
| 2008/0269730 A1 | 10/2008 | Dotson |
| 2008/0277007 A1 | 11/2008 | Unger et al. |
| 2008/0281250 A1 | 11/2008 | Bergsneider et al. |
| 2008/0289710 A1 | 11/2008 | Unger et al. |
| 2008/0306429 A1 | 12/2008 | Shields et al. |
| 2009/0043242 A1 | 2/2009 | Bene et al. |
| 2009/0043321 A1 | 2/2009 | Conston et al. |
| 2009/0043365 A1 | 2/2009 | Friedland et al. |
| 2009/0112245 A1 | 4/2009 | Haefliger |
| 2009/0124973 A1 | 5/2009 | D'Agostino et al. |
| 2009/0132040 A1 | 5/2009 | Frion et al. |
| 2009/0137983 A1 | 5/2009 | Bergheim et al. |
| 2009/0137989 A1 | 5/2009 | Kataoka |
| 2009/0138081 A1 | 5/2009 | Bergheim et al. |
| 2009/0151422 A1 | 6/2009 | Unger et al. |
| 2009/0182421 A1 | 7/2009 | Silvestrini et al. |
| 2009/0198213 A1 | 8/2009 | Tanaka |
| 2009/0204053 A1 | 8/2009 | Nissan et al. |
| 2009/0227933 A1 | 9/2009 | Karageozian |
| 2009/0227934 A1 | 9/2009 | Eutenever et al. |
| 2009/0264813 A1 | 10/2009 | Chang |
| 2009/0287233 A1 | 11/2009 | Huculak |
| 2009/0326432 A1 | 12/2009 | Schmidt et al. |
| 2010/0004581 A1 | 1/2010 | Brigatti et al. |
| 2010/0010416 A1 | 1/2010 | Juan, Jr. et al. |
| 2010/0010452 A1 | 1/2010 | Paques et al. |
| 2010/0025613 A1 | 2/2010 | Tai et al. |
| 2010/0030150 A1 | 2/2010 | Paques et al. |
| 2010/0042209 A1 | 2/2010 | Guarnieri |
| 2010/0057055 A1 | 3/2010 | Camras et al. |
| 2010/0057093 A1 | 3/2010 | Ide et al. |
| 2010/0076419 A1 | 3/2010 | Chew et al. |
| 2010/0087774 A1 | 4/2010 | Haffner et al. |
| 2010/0106073 A1 | 4/2010 | Haffner et al. |
| 2010/0121248 A1 | 5/2010 | Yu et al. |
| 2010/0121249 A1 | 5/2010 | Yu et al. |
| 2010/0121342 A1 | 5/2010 | Schieber et al. |
| 2010/0137981 A1 | 6/2010 | Silvestrini et al. |
| 2010/0152626 A1 | 6/2010 | Schwartz |
| 2010/0152641 A1 | 6/2010 | Yablonski |
| 2010/0158980 A1 | 6/2010 | Kopczynski et al. |
| 2010/0173866 A1 | 7/2010 | Hee et al. |
| 2010/0175767 A1 | 7/2010 | Unger et al. |
| 2010/0185138 A1 | 7/2010 | Yaron et al. |
| 2010/0185205 A1 | 7/2010 | Novakovic et al. |
| 2010/0191103 A1 | 7/2010 | Stamper et al. |
| 2010/0225061 A1 | 9/2010 | Bath |
| 2010/0234791 A1 | 9/2010 | Lynch et al. |
| 2010/0240987 A1 | 9/2010 | Christian et al. |
| 2010/0241046 A1 | 9/2010 | Pinchuk et al. |
| 2010/0255061 A1 | 10/2010 | De Juan, Jr. et al. |
| 2010/0262174 A1 | 10/2010 | Sretavan |
| 2010/0274258 A1 | 10/2010 | Silvestrini et al. |
| 2010/0274259 A1 | 10/2010 | Yaron et al. |
| 2010/0278898 A1 | 11/2010 | Hughes et al. |
| 2010/0280317 A1 | 11/2010 | Silvestrini et al. |
| 2011/0009874 A1 | 1/2011 | Wardle et al. |
| 2011/0009958 A1 | 1/2011 | Wardle et al. |
| 2011/0022065 A1 | 1/2011 | Shipp |
| 2011/0028883 A1 | 2/2011 | Juan, Jr. et al. |
| 2011/0028884 A1 | 2/2011 | Coroneo |
| 2011/0028983 A1 | 2/2011 | Silvestrini et al. |
| 2011/0046536 A1 | 2/2011 | Stegmann et al. |
| 2011/0046728 A1 | 2/2011 | Shareef et al. |
| 2011/0066098 A1 | 3/2011 | Stergiopulos |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0071524 A1 | 3/2011 | Keller |
| 2011/0077626 A1 | 3/2011 | Baerveldt et al. |
| 2011/0082385 A1 | 4/2011 | Diaz et al. |
| 2011/0087151 A1 | 4/2011 | Coroneo |
| 2011/0092878 A1 | 4/2011 | Tu et al. |
| 2011/0092965 A1 | 4/2011 | Slatkine et al. |
| 2011/0098629 A1 | 4/2011 | Juan, Jr. et al. |
| 2011/0098809 A1 | 4/2011 | Wardle et al. |
| 2011/0105987 A1 | 5/2011 | Bergheim et al. |
| 2011/0112546 A1 | 5/2011 | Juan, Jr. et al. |
| 2011/0118649 A1 | 5/2011 | Stegmann et al. |
| 2011/0118835 A1 | 5/2011 | Silvestrini et al. |
| 2011/0144641 A1 | 6/2011 | Dimalanta, Jr. et al. |
| 2011/0202049 A1 | 8/2011 | Jia et al. |
| 2011/0224597 A1 | 9/2011 | Stegmann et al. |
| 2011/0230877 A1 | 9/2011 | Huculak et al. |
| 2011/0244014 A1 | 10/2011 | Williams et al. |
| 2011/0245753 A1 | 10/2011 | Sunalp |
| 2011/0257623 A1 | 10/2011 | Marshall et al. |
| 2011/0306915 A1 | 12/2011 | De Juan, Jr. et al. |
| 2011/0319793 A1 | 12/2011 | Hyhynen |
| 2011/0319806 A1 | 12/2011 | Wardle |
| 2012/0016286 A1 | 1/2012 | Silvestrini et al. |
| 2012/0022409 A1 | 1/2012 | Gertner et al. |
| 2012/0022424 A1 | 1/2012 | Yamamoto et al. |
| 2012/0022429 A1 | 1/2012 | Silvestrini et al. |
| 2012/0035524 A1 | 2/2012 | Silvestrini |
| 2012/0035525 A1 | 2/2012 | Silvestrini |
| 2012/0065570 A1 | 3/2012 | Yeung et al. |
| 2012/0071809 A1 | 3/2012 | Tu et al. |
| 2012/0071908 A1 | 3/2012 | Sorensen et al. |
| 2012/0078158 A1 | 3/2012 | Haffner et al. |
| 2012/0078281 A1 | 3/2012 | Cox et al. |
| 2012/0078362 A1 | 3/2012 | Haffner et al. |
| 2012/0089072 A1 | 4/2012 | Cunningham, Jr. |
| 2012/0089073 A1 | 4/2012 | Cunningham, Jr. |
| 2012/0109040 A1 | 5/2012 | Smedley et al. |
| 2012/0123439 A1 | 5/2012 | Romoda et al. |
| 2012/0123440 A1 | 5/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0203262 A1 | 8/2012 | Connors et al. |
| 2012/0220917 A1 | 8/2012 | Silvestrini et al. |
| 2012/0232570 A1 | 9/2012 | Jenson et al. |
| 2012/0238994 A1 | 9/2012 | Nazzaro et al. |
| 2012/0259195 A1 | 10/2012 | Haffner et al. |
| 2012/0271272 A1 | 10/2012 | Hammack et al. |
| 2012/0283557 A1 | 11/2012 | Berlin |
| 2012/0289883 A1 | 11/2012 | Meng et al. |
| 2012/0310137 A1 | 12/2012 | Silvestrini |
| 2012/0323159 A1 | 12/2012 | Wardle et al. |
| 2013/0006164 A1 | 1/2013 | Yaron et al. |
| 2013/0006165 A1 | 1/2013 | Eutenener et al. |
| 2013/0018295 A1 | 1/2013 | Haffner et al. |
| 2013/0018296 A1 | 1/2013 | Bergheim et al. |
| 2013/0018412 A1 | 1/2013 | Journey et al. |
| 2013/0079701 A1 | 3/2013 | Schieber et al. |
| 2013/0079759 A1 | 3/2013 | Dotson et al. |
| 2013/0090534 A1 | 4/2013 | Burns et al. |
| 2013/0110125 A1 | 5/2013 | Silvestrini et al. |
| 2013/0131577 A1 | 5/2013 | Bronstein et al. |
| 2013/0144202 A1 | 6/2013 | Field et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0150776 A1 | 6/2013 | Bohm et al. |
| 2013/0150777 A1 | 6/2013 | Bohm et al. |
| 2013/0158381 A1 | 6/2013 | Rickard |
| 2013/0165840 A1 | 6/2013 | Orge |
| 2013/0184631 A1 | 7/2013 | Pinchuk |
| 2013/0245532 A1 | 9/2013 | Tu et al. |
| 2013/0253404 A1 | 9/2013 | Tu |
| 2013/0253405 A1 | 9/2013 | Tu |
| 2013/0253528 A1 | 9/2013 | Haffner et al. |
| 2013/0281910 A1 | 10/2013 | Tu et al. |
| 2013/0289467 A1 | 10/2013 | Haffner et al. |
| 2014/0034607 A1 | 2/2014 | Meng et al. |
| 2014/0052046 A1 | 2/2014 | Peartree et al. |
| 2014/0081194 A1 | 3/2014 | Burns et al. |
| 2014/0135916 A1 | 5/2014 | Clauson et al. |
| 2014/0155803 A1 | 6/2014 | Silvestrini |

(56) References Cited

U.S. PATENT DOCUMENTS

| | | |
|---|---|---|
| 2014/0276332 A1 | 9/2014 | Crimaldi et al. |
| 2015/0065940 A1 | 3/2015 | Rangel-Friedman et al. |
| 2015/0374546 A1 | 12/2015 | Hill |
| 2016/0038338 A1 | 2/2016 | Rangel-Friedman et al. |
| 2016/0151204 A1 | 6/2016 | Haffner et al. |
| 2018/0021170 A1 | 1/2018 | Haffner et al. |
| 2018/0177633 A1 | 6/2018 | Haffner et al. |
| 2020/0155349 A1 | 5/2020 | Haffner et al. |
| 2020/0179171 A1 | 6/2020 | Crimaldi et al. |

FOREIGN PATENT DOCUMENTS

| | | |
|---|---|---|
| CA | 2273331 | 6/1998 |
| CA | 2244646 A1 | 2/1999 |
| CA | 2311244 | 6/1999 |
| CA | 2643357 | 11/1999 |
| CH | 92111244 | 7/1993 |
| DE | 19840047 A1 | 3/2000 |
| DE | 10042310 A1 | 3/2002 |
| DE | 10127666 A1 | 1/2003 |
| EP | 0436232 A1 | 7/1991 |
| EP | 0550791 A | 7/1993 |
| EP | 0858788 A1 | 8/1998 |
| EP | 0881055 A1 | 12/1998 |
| EP | 0898947 A2 | 3/1999 |
| EP | 1114627 A1 | 7/2001 |
| EP | 1534363 A2 | 6/2005 |
| EP | 2088976 | 8/2009 |
| EP | 2260803 A2 | 12/2010 |
| EP | 2351589 | 8/2011 |
| EP | 2982354 A1 | 2/2016 |
| EP | 2985012 A1 | 2/2016 |
| FR | 2553658 A1 | 4/1985 |
| FR | 2710269 A1 | 3/1995 |
| FR | 2721499 | 12/1995 |
| FR | 2757068 A1 | 6/1998 |
| GB | 2296663 A | 7/1996 |
| JP | 11-123205 | 5/1999 |
| JP | 2001-504732 | 4/2001 |
| JP | 2003-520077 | 7/2003 |
| JP | 2004-500220 A | 1/2004 |
| JP | 2005-512607 A | 5/2005 |
| JP | 2005-533619 | 11/2005 |
| JP | 2012-198134 | 9/2012 |
| JP | 2013-208434 | 10/2013 |
| JP | 5328788 B2 | 10/2013 |
| JP | 2014-193366 | 10/2014 |
| JP | 2014-240022 | 12/2014 |
| RU | 2022539 C1 | 11/1994 |
| RU | 2143250 | 12/1999 |
| RU | 2160573 C1 | 12/2000 |
| WO | WO 89/00869 A1 | 2/1989 |
| WO | WO 91/08784 | 6/1991 |
| WO | WO 91/18568 A1 | 12/1991 |
| WO | WO 92/08406 | 5/1992 |
| WO | WO 92/19294 | 11/1992 |
| WO | WO 94/02081 | 2/1994 |
| WO | WO 94/13234 | 6/1994 |
| WO | WO 94/21205 A1 | 9/1994 |
| WO | WO 95/08310 A1 | 3/1995 |
| WO | WO 96/20742 A1 | 7/1996 |
| WO | WO 98/23237 A1 | 6/1998 |
| WO | WO 1998/030181 A1 | 7/1998 |
| WO | WO 98/35639 A1 | 8/1998 |
| WO | WO 98/37831 | 9/1998 |
| WO | WO 99/26567 A1 | 6/1999 |
| WO | WO 99/30641 A1 | 6/1999 |
| WO | WO 99/30644 | 6/1999 |
| WO | WO 99/38470 A2 | 8/1999 |
| WO | WO 99/38470 A3 | 8/1999 |
| WO | WO 00/13627 A1 | 3/2000 |
| WO | WO 00/64389 A1 | 11/2000 |
| WO | WO 00/64390 A1 | 11/2000 |
| WO | WO 00/64391 A1 | 11/2000 |
| WO | WO 00/64393 A1 | 11/2000 |
| WO | WO 00/67687 A1 | 11/2000 |
| WO | WO 00/72788 A1 | 12/2000 |
| WO | WO 01/50943 A2 | 7/2001 |
| WO | WO 01/68016 A2 | 9/2001 |
| WO | WO 01/78631 A2 | 10/2001 |
| WO | WO 01/78656 A2 | 10/2001 |
| WO | WO 01/85065 | 11/2001 |
| WO | WO 01/94784 | 12/2001 |
| WO | WO 01/97727 | 12/2001 |
| WO | WO 02/36052 | 5/2002 |
| WO | WO 02/074052 A2 | 9/2002 |
| WO | WO 02/102274 A2 | 12/2002 |
| WO | WO 03/015659 A2 | 2/2003 |
| WO | WO 03/041622 | 5/2003 |
| WO | WO 03/045290 A1 | 6/2003 |
| WO | WO 03/073968 A2 | 9/2003 |
| WO | WO 04/008945 A2 | 1/2004 |
| WO | WO 2004/093761 A1 | 11/2004 |
| WO | WO 05/046782 A2 | 5/2005 |
| WO | WO 2005/107664 A2 | 11/2005 |
| WO | WO 2005/107845 | 11/2005 |
| WO | WO 05/117780 | 12/2005 |
| WO | WO 07/084582 | 7/2007 |
| WO | WO 07/087061 A2 | 8/2007 |
| WO | WO 2008/061043 A2 | 5/2008 |
| WO | WO 2008/083118 | 7/2008 |
| WO | WO 2009/012406 | 1/2009 |
| WO | WO 2009/126569 | 10/2009 |
| WO | WO 2009/151543 | 12/2009 |
| WO | WO 2010/093945 A3 | 8/2010 |
| WO | WO 2010/135369 | 11/2010 |
| WO | WO 2011/020633 A1 | 2/2011 |
| WO | WO 13/148275 | 10/2013 |
| WO | WO 14/151070 | 9/2014 |

OTHER PUBLICATIONS

Chu, Jennifer, "Detecting the Danger Signs of Glaucoma", Technology Review Published by MIT, Aug. 15, 2007, 2 pp., http://www.technologyreview.com/printer_friendly_article.aspx?id=19257.

Constad, William H., et al., Use of an Angiotensin Converting Enzyme Inhibitor in Ocular Hypertension and Primary Open-Angle Glaucoma, 103 AM J Opthalmol 674 (1988).

Coote, "Glaucoma Hollow Fiber Filters—A New Glaucoma Seton. Preliminary Results," J. Glaucoma, vol. 8, No. 1, Supplement (1999), p. S4 (1 page).

De Juan et al., "Refinements in microinstrumentation for vitrous surgery," Am. J. Ophthalmol. 109:218-20 (1990).

Dorland's Illustrated Medical Dictionary, 28th Edition, Philadelphia: W.B. Saunders Company, 1994, p. 167.

Ellis, R., "Reduction of Intraocular Pressure Using Plastics in Surgery," American Journal of Ophthalmology, vol. 50, pp. 733-743 (1960).

Emi, Kazayuki, et al., Hydrostatic Pressure of the Suprachoroidal Space, Investigative Ophthalmology & Visual Science, vol. 30, No. 2, Feb. 1989 (pp. 233-239).

Fletcher, Daniel A., Ph.D., Daniel V. Palanker, Ph.D., Philip Hule, M.D., Jason Miller, MS, Michael F. Marmor, M.D. and Mark S. Blumenkranz, M.D.; *Intravascular Drug Delivery With a Pulsed Liquid Microjet*; (Reprinted) Arch Ophthalmology; vol. 120, Sep. 2002, pp. 1206-1208.

Grant, W.M., MD, Further Studies on Facility of Flow Through the Trabecular Meshwork, *AMA Archives of Ophthalmology*, Oct. 1958, vol. 60, pp. 523-533.

Grierson, I., R.C. Howes, and Q. Wang, *Age-related Changes in the Canal of Schlemm*, Exp. Eye Res., 1984, vol. 39, pp. 505-512.

Hill, R.A., Q. Ren, D.C. Nguyen, L.H. Liaw, & M.W. Berns, Free-electron Laser (FEL) Ablation of Ocular Tissues, *Lasers Med Sci* 1998, vol. 13, pp. 219-226.

Hill, Richard A., MD, George Baerveldt, MD, Serdar A. Ozler, MD, Michael Pickford, BA, Glen A. Profeta, BS, & Michael W. Berns, PhD, Laser Ablation (LTA), *Lasers in Trabecular Surgery and Medicine*, 1991, vol. 11, pp. 341-346.

(56) References Cited

OTHER PUBLICATIONS

Hoeh et al., Early Postoperative Safety and Surgical Outcomes After Implantation of a Suprachoroidal Micro-Stent for the Treatment of Open-Angle Glaucoma Concomitant with Cataract Surgery, 39 J. Cataract Refract. Surg. 431 (2013).

Hoerauf, Hans, Christopher Wirbelauer, Christian Scholz, Ralf Engelhardt, Peter Koch, Horst Laqua, and Reginald Birngruber, *Slit-lamp-adapted optical coherence tomography of the anterior segment*, Graefe's Arch Clin Exp Ophthalmol, 2000, vol. 238, pp. 8-18.

Hoskins, et al., "Aqueous Humor Outflow", Becker-Shaffer's Diagnosis and Therapy of the Glaucomas, 6th Edition, Chapter 4, pp. 41-66, 1989.

Hoskins, H. Dunbar, et al., Diagnosis and Therapy of the Glaucomas, Chapter 4: Aqueous Humor Outflow, 61 edition, pp. 41-66 (1989) (28 pages).

Jacobi, Phillip C., MD, Thomas S. Dietlein, MD and Gunter K. Krieglstein, MD, Microendoscopic Trabecular Surgery in Glaucoma Management, *Ophthalmology*, 1999 vol. 106, No. 3, pp. 538-544.

Jacobi, Phillip C., MD, Thomas S. Dietlein, MD and Gunter K. Krieglstein, MD, Bimanual Trabecular Aspiration in Pseudoexfoliation Glaucoma, *Ophthalmology*, 1998, vol. 105, No. 5, May 1998, pp. 886-894.

Jacobi, Phillip C., MD, Thomas S. Dietlein, MD and Gunter K. Krieglstein, MD, Goniocurettage for Removing Trabecular Meshwork: Clinical Results of a new Surgical Technique in Advanced Chronic Open-Angle Glaucoma, *American Journal of Ophthalmology*, May 1999, pp. 505-510.

Jocson, Vincente, L., M.D.; *Air Trabeculotomy*, American Journal of Ophthalmolgy: vol. 79, No. 1, Jan.-Jun. 1975; pp. 107-111.

Johnson, et al., *Schlemm's Canal Becomes Smaller After Successful Filtration Surgery*, (reprinted) ARCM Ophthalmol/vol. 118, Sep. 2000 (www.archophthalmol.com) p. 1251-1256.

Johnstone, M.A., R. Stegmann, and B.A. Smit, *American Glaucoma Society, 12th Annual Meeting, Cylindrical Tubular Structures Spanning from Trabecular Meshwork Across SC*, Laboratory Studies with SEM, TEM and Tracers Correlated with Clinical Findings, Abstract No. 18., p. 39, 2002.

Jordan et al., Cyclodialysis ab interno as a surgical approach to intractable glaucoma, Graefe's Arch Clin Exp Opthalmol (2007) 245, pp. 1071-1076.

Jordon, et al., "A Novel Approach to Suprachoroidal Drainage for the Surgical Treatment of Intractable Glaucoma," J Glaucoma 15(3): 200-205 (2006).

Katuri, Kalyan C., Asrani, Sanjay and Ramasubramanian, Melur K., "Intraocular Pressure Monitoring Sensors", IEEE Sensors Journal, vol. 8, No. 1, Jan. 2008, 8 pp.

Katz, L. Jay, MD, A Call for Innovative Operations for Glaucoma, *Arch Ophthalmology*, Mar. 2000, vol. 118, pp. 412-413.

Kimura, T., et al.; The Efficacy of Isopropyl Unoppostone in the Concomitant Application of B Blocker, Dipivefrin and Pilocarpine; Glaucoma Clinical Pharmacology II, Abstract B56, IVOS 1998 vol. 39, (cover page and p. No. S258).

Klemm, A. Balazs, J. Draeger, R. Wiezorrek, *Experimental use of space-retaining substances with extended duration: functional and morphological results*, Graefe's Arch Clin Exp Ophthalmol (1995) 233:592-597.

Krejci, "Cyclodialysis with Hydroxyethyl Methacrylate Capillary Strip (HCS)," Opthalmologica, vol. 164 (1972), pp. 113-121 (9 pages).

Llobet, et al., Understanding Trabecular Meshwork Physiology: A Key to the Control of Intraocular Pressure?, News Physiol Sci vol. 18, pp. 205-209 (2003).

Matsumoto, Yasuhiro and Douglas H. Johnson, *Trabecular Meshwork Phagocytosis in Glaucomatous Eyes*, Ophthalmologica 1977, vol. 211, pp. 147-152.

Moses, Robert A., et al., "Blood Reflux in Schlemm's Canal", Arch Ophthamol., vol. 97, Jul 1979, pp. 1307-1310.

Nickells, Robert W., *Apoptosis of Retinal Ganglion Cells in Glaucoma: An Update of the Molecular Pathways Involved in Cell Death*, Survey of Ophthalmology, vol. 43, Supplement 1, Jun. 1999, pp. S-151 through S-161.

Oatts et al., "In vitro an in vivo comparison of two suprachoroidal shunts," Invest. Opthalmol. Vis. Sci. 54:5416-23 (2013).

Ocular Swan Autoclavable Gonioprism from at least as early as Jun. 29, 2007 in 3 pages, downloaded from http://ocularinc.com.

Olsen, et al., "Cannulation of the Suprachoroidal Space: A Novel Drug Delivary Methodology to the Posterior Segment", American Journal of Ophthalmology, Nov. 2006, pp. 777-787.e2 (13 pages).

Ozdamar, et al., "Suprachoroidal Seton Implantation in Refractory Glaucoma: A novel Surgical Technique", Journal of Glaucoma 12:354-359, 2003.

Pinnas, G., et al., "Cyclodialysis With Teflon Tube Implants, "American Journal of Ophthalmology, vol. 68, No. 5 pp. 879-883 (Nov. 1969).

Portney, G., M.D., "Silicone Elastomer Implantation Cyclodialysis: A Negative Report," Arch. Opthalmol., vol. 89, pp. 10-12 (Jan. 1973).

Putney, Luanna K., Cecile Rose T. Vibat, and Martha E. O'Donnell, *Intracellular C1 Regulates Na—K—C1 Cotransport Activity in Human Trabecular Meshwork Cells*, 1999 American Physiological Society, Sep. 1999, pp. C373 through C383.

Qu, I., et al., Isolation and characterization of noncytopathic pestivirus mutants reveals a role for nonstructural protein NS4B in viral cytopathogenicity. Nov. 2001 Journal of Virology. vol. 75, No. 22, 10651-62, see Fig. 1 and p. 10654.

Radhakrishnan, Sumita, Andrew M. Rollins, Jonathan E. Roth, S. Yazddanfar, Volker Westphal, David Bardenstein, and Joseph Izatt, *Real-Time Optical Coherence Tomography of the Anterior Segment at 1310 nm*, Arch Ophthalmology, Aug. 2001, vol. 119, pp. 1179-1185.

Ritch, et al., "Uveoscleral Outflow," The Glaucomas, 2nd Edition, Chapter 15, pp. 337-343, 1996.

Rohen, Johannes W., Grune & Stratton, Harcourt Brace Jovanovich Publishers, edited by J.E. Cairns, *Glaucoma*, vol. 1, Chapter 14, *Anatomy of the Aqueous Outflow Channels*, 1986 pp. 277-296.

Rosenberg, et al., "Implants in Glaucoma Surgery", The Glaucomas 1996, Chapter 88, pp. 1783-1807 (27 pages).

Rowan, MD, *Combined Cyclodialysis and Cataract Surgery*, Ophthalmic Surgery and Lasers, Dec. 1998, vol. 29, No. 12, pp. 962-968 (9 pages).

Schwartz, Arthur L., MD, & Douglas R. Anderson, MD, Trabecular Surgery, *Arch Ophthalmol*, vol. 92, Aug. 1974, pp. 134-138.

Sherman, Steven H., et al., "The Fate of Anterior Chamber Fluorescein in the Monkey Eye 1. The Anterior Chamber Outflow Pathways", Exp. Eye Res. vol. 27, pp. 159-173 (1978) (15 pages).

Shields, M. Bruce, MD, *A Study Guide for Glaucoma: Aqueous Humor Dynamics*, Copyright 1982, pp. 6-43.

Shields, M. Bruce, Aqueous Humor Dynamics, Textbook of Glaucoma, Fourth Ed., Williams & Wilkins Publishers, 1998, Ch. 2, pp. 5-31.

Spiegel, Detlev, *7 chirurgische Glaukomtherapie*, (English translation enclosed) pp. 79-88 Spiegel, D., "Surgical Glaucoma Therapy" in Benefits and Risks of Ophthalmological Therapy (Kampik & Grehn, Eds.) Ch. 7 (Germany 1998).

Spiegel, Detliev, MD, Karin Kobuch, MD, Richard A. Hill, MD, Ronald L. Gross, MD, Schlemm's Canal Implant: A New Method to Lower Intraocular Pressure in Patients With POAG?, *Opthalmic Surgery and Lasers*, Jun. 1999, vol. 30, No. 6, pp. 492-494.

Strange, Kevin (edited by), *Cellular and Molecular Physiology of Cell Volume Regulation*, Library of Congress Cataloging in-Publication Data, CRC Press, Inc., 1994 pp. 312-321.

Tatton, W.G., *Apoptotic Mechanisms in Neurodegeneration: Possible Relevance to Glaucoma*, European Journal of Ophthalmology, Jan.-Mar. 1999, vol. 9, Supplement 1, pp. S22 through S29.

Tatton, William, Ruth M.E. Chalmers-Redman, Ajay Sud, Steven M. Podos, and Thomas Mittag, *Maintaining Mitochondrial Membrane Impermeability: An Opportunity for New Therapy in Glaucoma*, Survey of Ophthalmology, vol. 45, Supplement 3, May 2001, pp. S277 through S283.

(56) References Cited

OTHER PUBLICATIONS

Timmermans, et al., Possible Subdivion of Postsynapic Adrenoceptors Mediating Pressor Responses in the Pithed Rat; Nauyn-Schmeideberg's Arch. Pharmacol., 310, pp. 189-193 (1979).
Tsontcho Ianchulev, Chapter 21: The CyPass Suprachoroidal Micro-Stent, in J.R. Samples &I.I.K. Ahmed (eds.), Surgical Innovations in Glaucoma 229 (Springer Science+Business Media 2014).
Troncoso, M.D., Cyclodialysis with Insertion of a Metal Implant in the Treatment of Glaucoma, Read before the Section on Ophthalmology at the Ninetieth Annual Session of the American Medical Association, St. Louis, May 17, 1939, Archives of Ophthalmology, pp. 270-300, downloaded from www.archophthalmol.com on Aug. 5, 2010.
Troncoso, Manuel U., Use of tantalum implants for inducing a permanent hypotony in rabbits' eyes, American Journal of Ophthalmology, vol. 32, No. 4, Apr. 1949, pp. 499-508 (11 pages).
Wagner, Justin A., Edwards, Aurélie, and Schuman, Joel S., Characterization of Uveoscleral Outflow in Enucleated Porcine Eyes Perfused Under Constant Pressure, *Invest Ophthalmol Vis Sci.* Sep. 2004; 45(9): 3203-3206 (9 pages).
Welsh, N. H., et al., "The 'deroofing' of Schlemm's canal in patients with open-angle glaucoma through placement of a collagen drainage device", Ophthalmic Surg. Lasers, vol. 29, No. 3, Mar. 1998,pp. 216-226 (abstract only).
Zhou, Jianbo, PhD, Gregory T. Smedley, PhD., *A Trabecular Bypass Flow Hypothesis*, Feb. 2005, vol. 14 No. 1, pp. 74-83.
Bae, et al., "In vitro experiment of the pressure regulating valve for a glaucoma implant", Journal of Micromechanics and Microengineering 13.5, 13:613-619, No. 5, Sep. 2003.
Bartolomei, et al., "Seton implantation to divert aqueous humor", Journal of Glaucoma, 13:348-349, No. 4, Aug. 2004.
Bucciarelli, Patrice D., Working Model is Next Step in Team's Long Journey to Commercial Product, Healthfirst, Business First of Louisville, louisville.bizjournals.com, Feb. 27, 2004.
Chen, et al., "Trabeculetomy combined with implantation of sil-icon rubber slice for intractable glaucoma", Eye Science, 18:95-98, vol. 2, Jun. 2002.
Chen, P.-J., Rodger, D.C., Meng, E., Humayun, M.S., Tai, Y.-C., "Implantable Unpowered Parylene MEMS Intraocular Pressure Sensor", Microtechnologies in Medicine and Biology, 2006 International Conference on Publication Date: May 9-12, 2006, 5pp., downloaded from http://ieeezxplore.ieee.org/xpl/freeabs_all.jsp?arnumber=4281361.
Duane's Ophthalmology on CD-ROM, 2006 Edition, Chapter 56—Medical Therapy of Glaucoma by Marc Weitzman and Joseph Caprioli.
Gal, "A novel glaucoma drainage valve", ProQuest Dissertations Publishing, 131 pages, 1999.
Johnson, Douglas H., M.D., et al.: Basic Sciences in Clinical Glaucomal How Does Nonpenetrating Glaucoma Surgery Work? Aqueous Outflow Resistance and Glaucoma Surgery; Journal of Glaucoma; 2001, vol. 10, No. 1, pp. 55-67.
Karlen, M. E., et al., "Deep sclerectomy with collagen implant: medium term results", Br. J. Ophthalmol. vol. 83, No. 1, Jan. 1999, pp. 6-11 (abstract only).
Kim et al., Controlled Drug Release from an Ocular Implant: An Evaluation Using Dynamic Three-Dimensional Magnetic Resonance Imaging. Invest Ophthalmol Vis Sci. 2004;45:2722-2731.
Lim, "Development of a new glaucoma drainage device", ProQuest Dissertations Publishing, 147 pages, 2001.
Ning, "Optimum Design of a New Aqueous Humor Drainage Implant for Glaucoma and the Animal", ProQuest Dissertations Publishing, 2004.
Pajic, Bojan et al., "A novel technique of ab interno glaucoma surgery: follow-up results after 24 months", Graefe's Arch Clin Exp Ophthalmol, Jul. 2005, (2006) 244:22-27.
Pederson, Jonathan et al., "Uveoscleral Aqueous Outflow in the Rhesus Monkey: Importance of Uveal Reabsorption," Invest. Ophthalmol, Visual Sci. Nov. 1977, Uveal Reabsorption of Aqueous Humor, vol. 16, No. 11, pp. 1008-1017.
Refojo, "Current status of biomaterials in ophthalmology", Survey of ophthalmology, 26:257-265, No. 5, 1982.
Rizq et al., Intraocular Pressure Measurement at the Choroid Surface: A Feasibility Study with Implications for Implantable Microsystems, Br J Ophthalmol 2001; 85:868-871, Jul. 2001.
Scott, et al., "Use of glaucoma drainage devices in the management of glaucoma associated with aniridia", American Journal of Ophthalmology, 135:155-159, No. 2, Feb. 1, 2003.
Tham, et al., "Incisional surgery for angle closure glaucoma", Seminars in Ophthalmology, 17:92-99, No. 2, Jun. 2002.
Tsontcho Ianchulev, Chapter 3: Suprachoroidal Space as a Therapeutic Target, in J.R. Samples & I.I.K. Ahmed (eds.), Surgical Innovations in Glaucoma 33 (Springer Science + Business Media 2014).
Van Der Veen, G., et al., "The Gonioseton, A Surgical Treatment for Chronic Glaucoma," Documenta Ophthalmologica, 1990 (75) pp. 365-375.
Walter, et al., Development of a Completely Encapsulated Intraocular Pressure Sensor, Ophthalmic Research Nov.-Dec. 2000; 32:278-284.
Webster's Third New International Dictionary of the English Language (Unabridged), definitions of "deploy" and "deployment", p. 605 (2002) (4 pages).
Yablonski, "Internal tube shunt from anterior chamber to suprachoroidal space: A novel glaucoma surgery", IOVS, vol. 46, No. Suppl., p. 1223, 2005.
Yablonski, "Trabeculectomy with internal Tube Shunt—A novel Glaucoma surgery", Journal of Glaucoma, vol. 14, No. 2:91-97, 2005.

\* cited by examiner

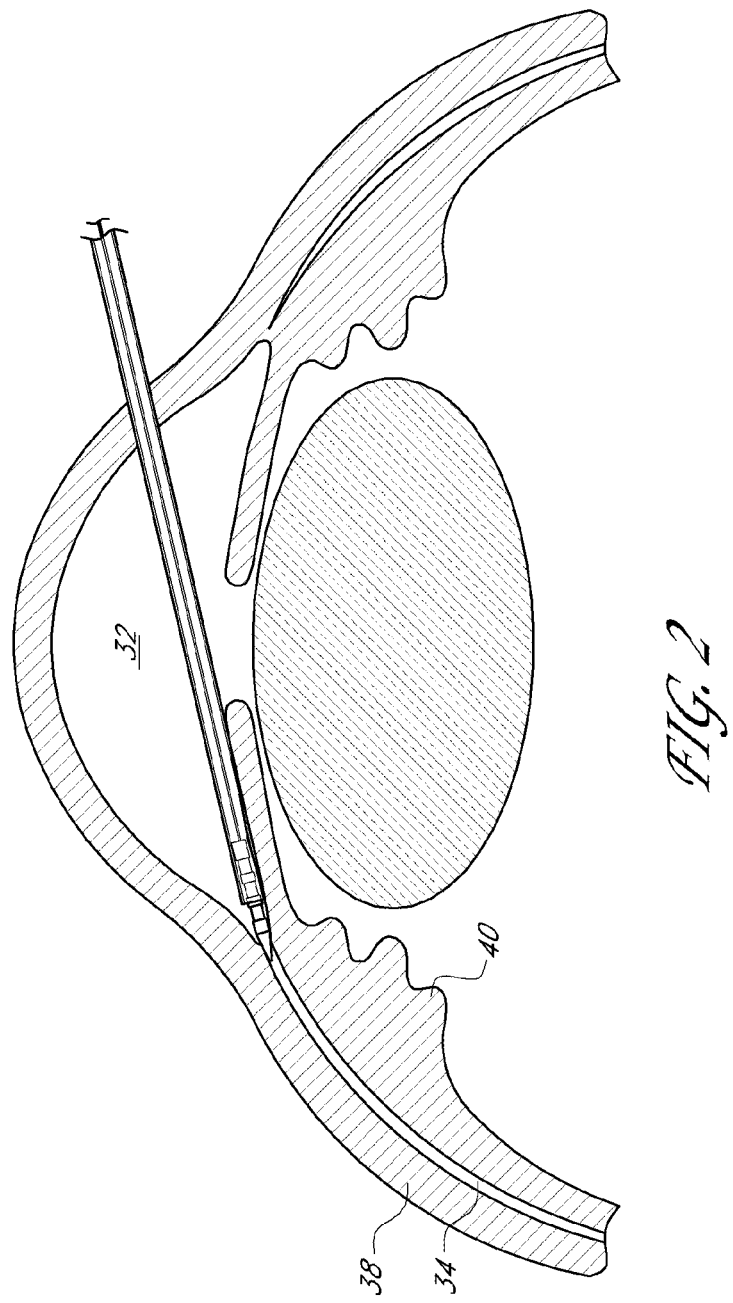

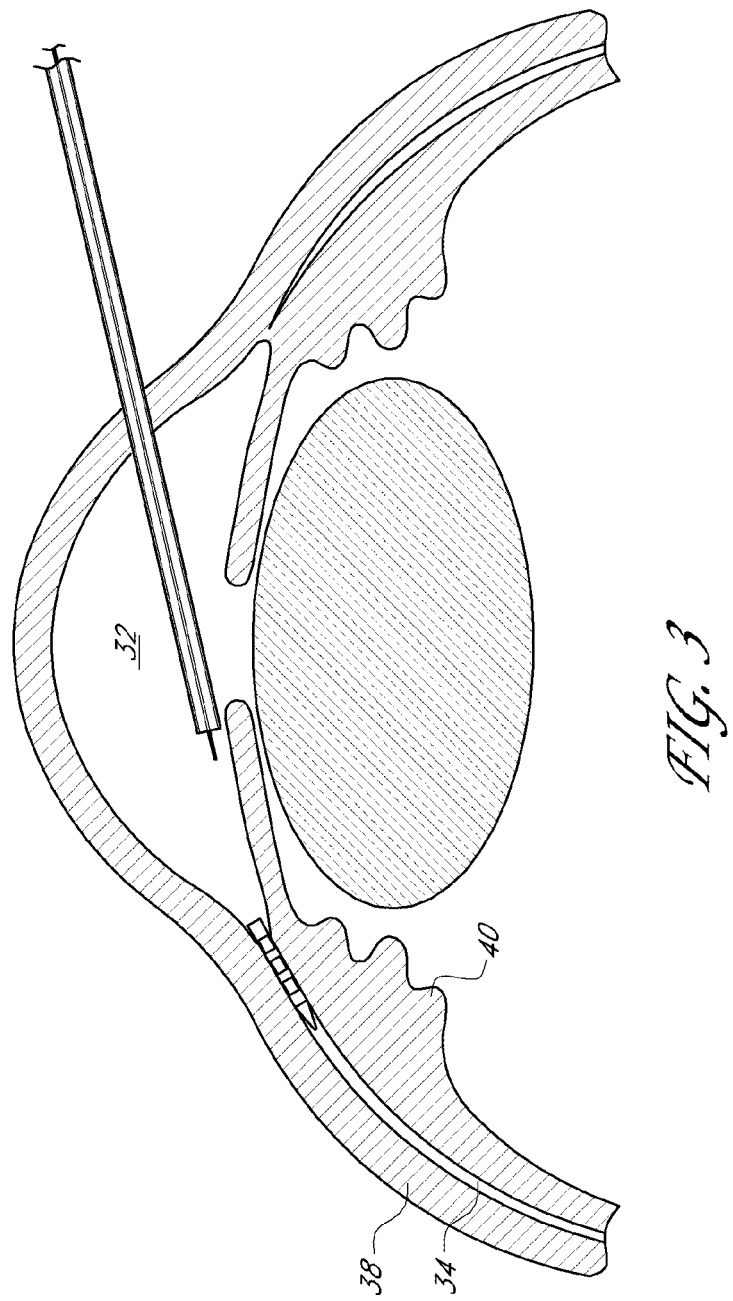

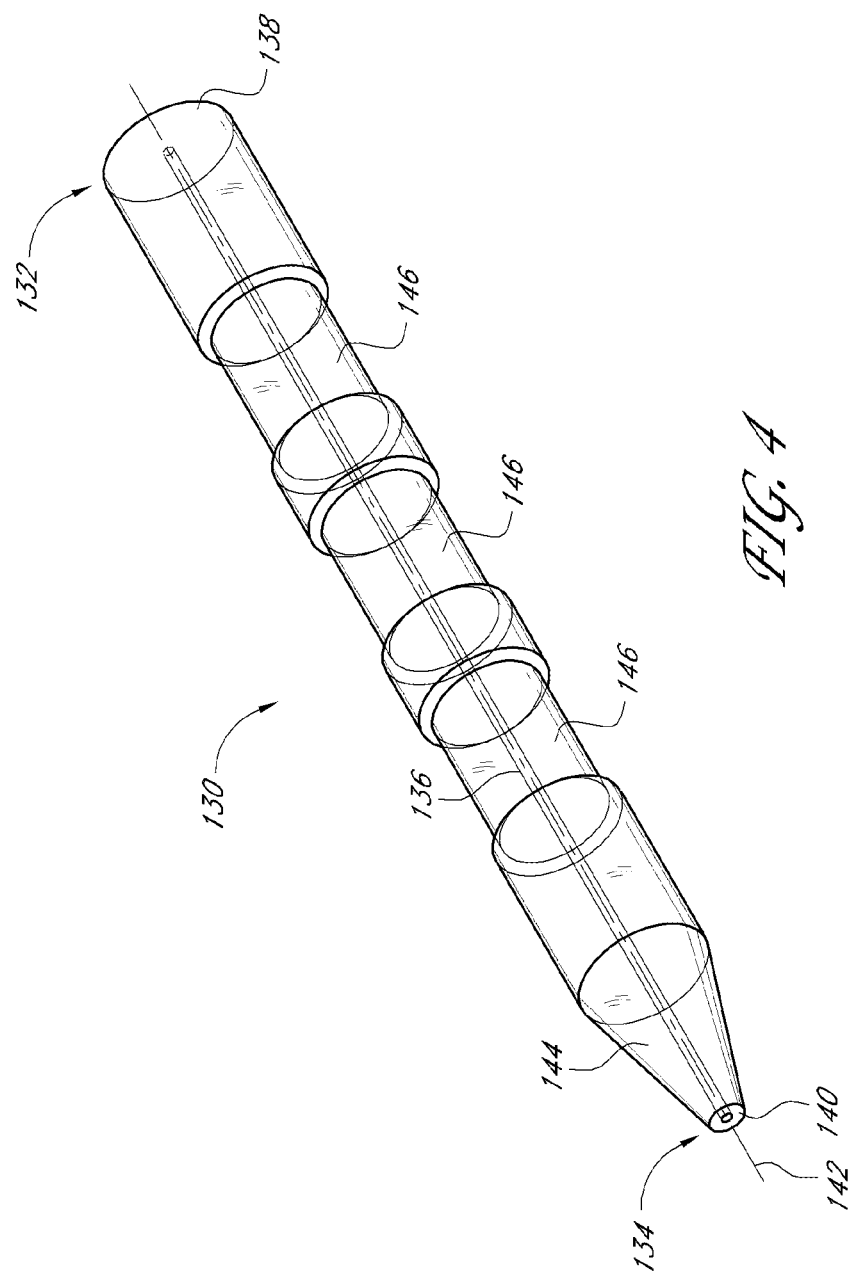

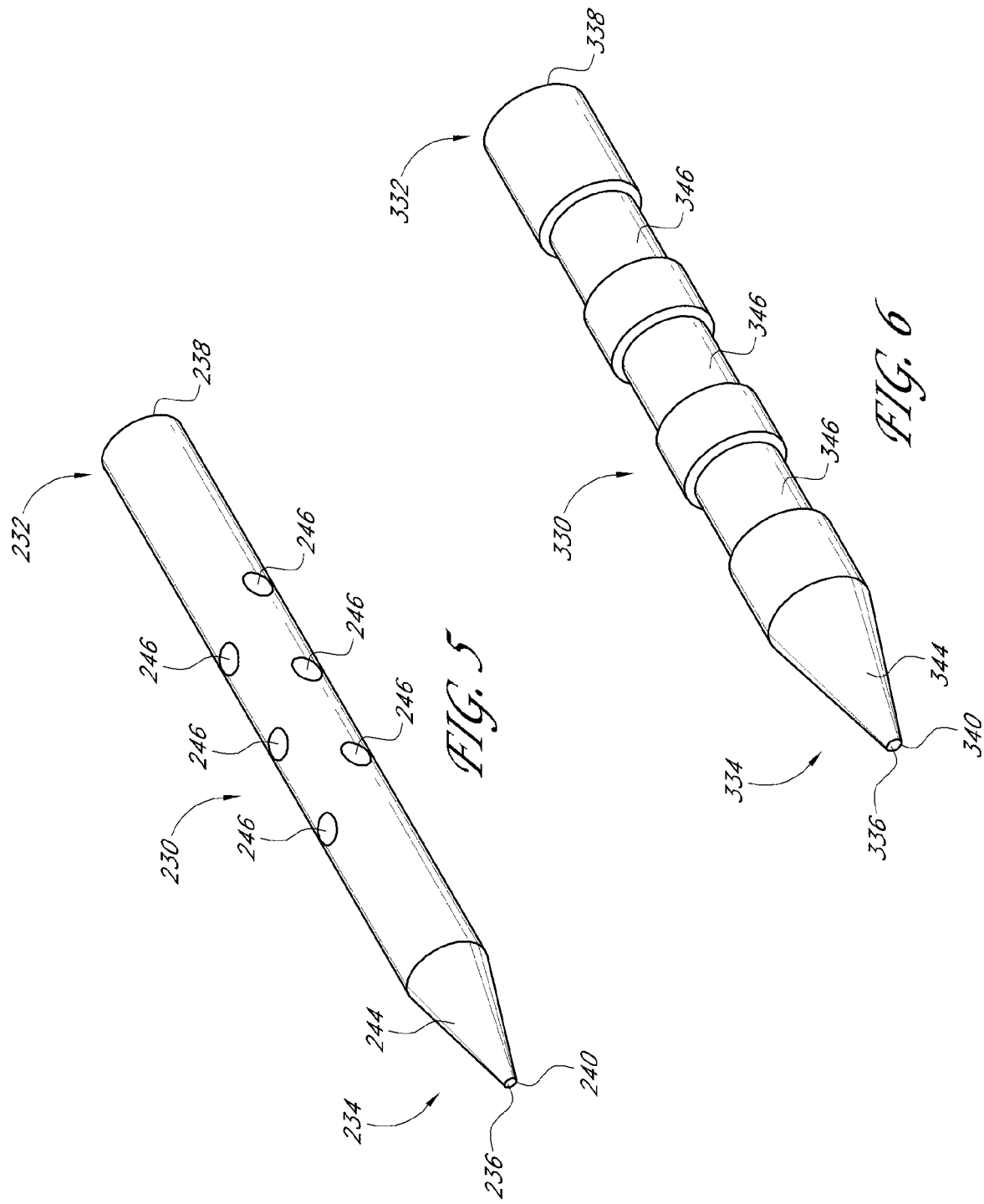

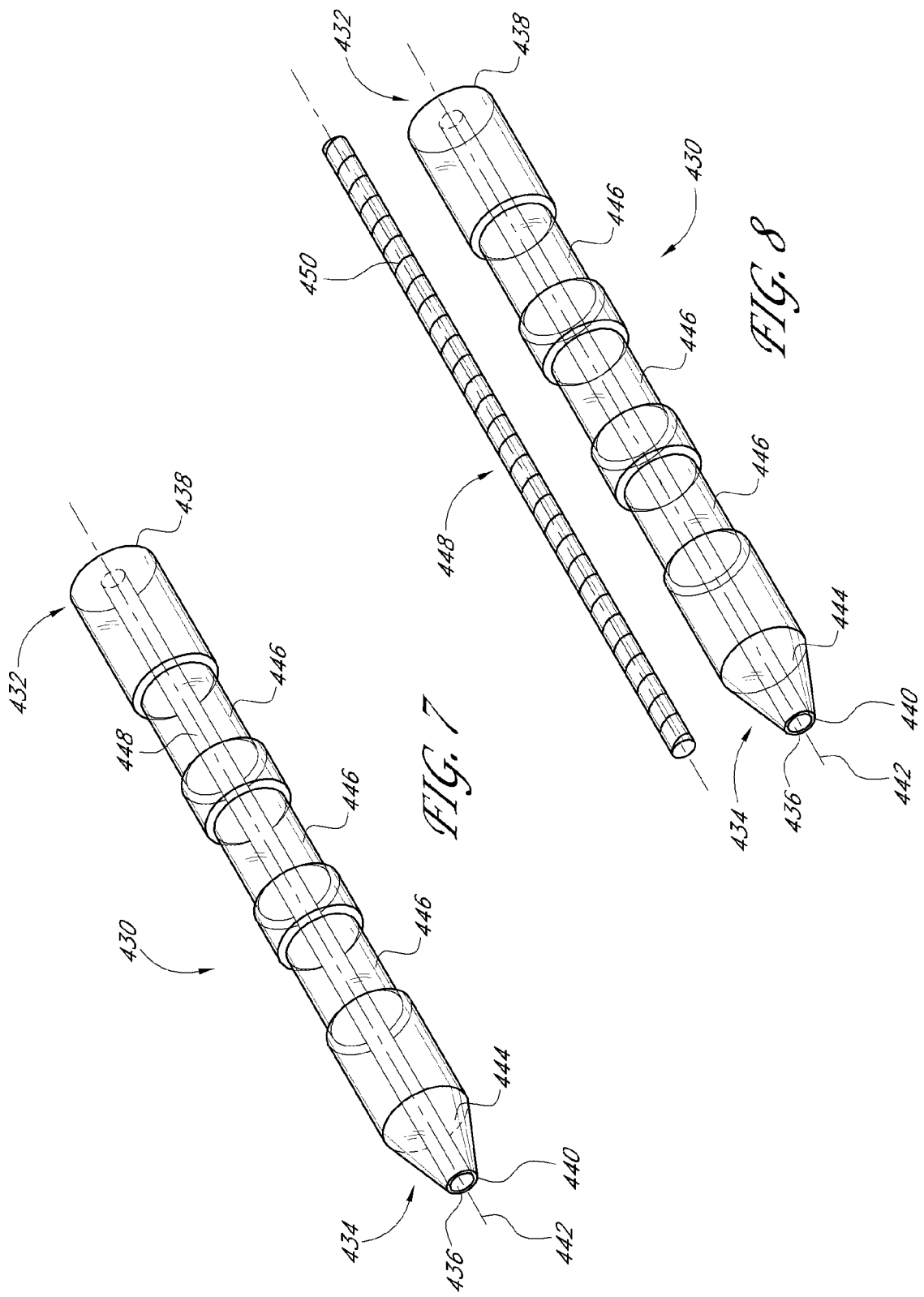

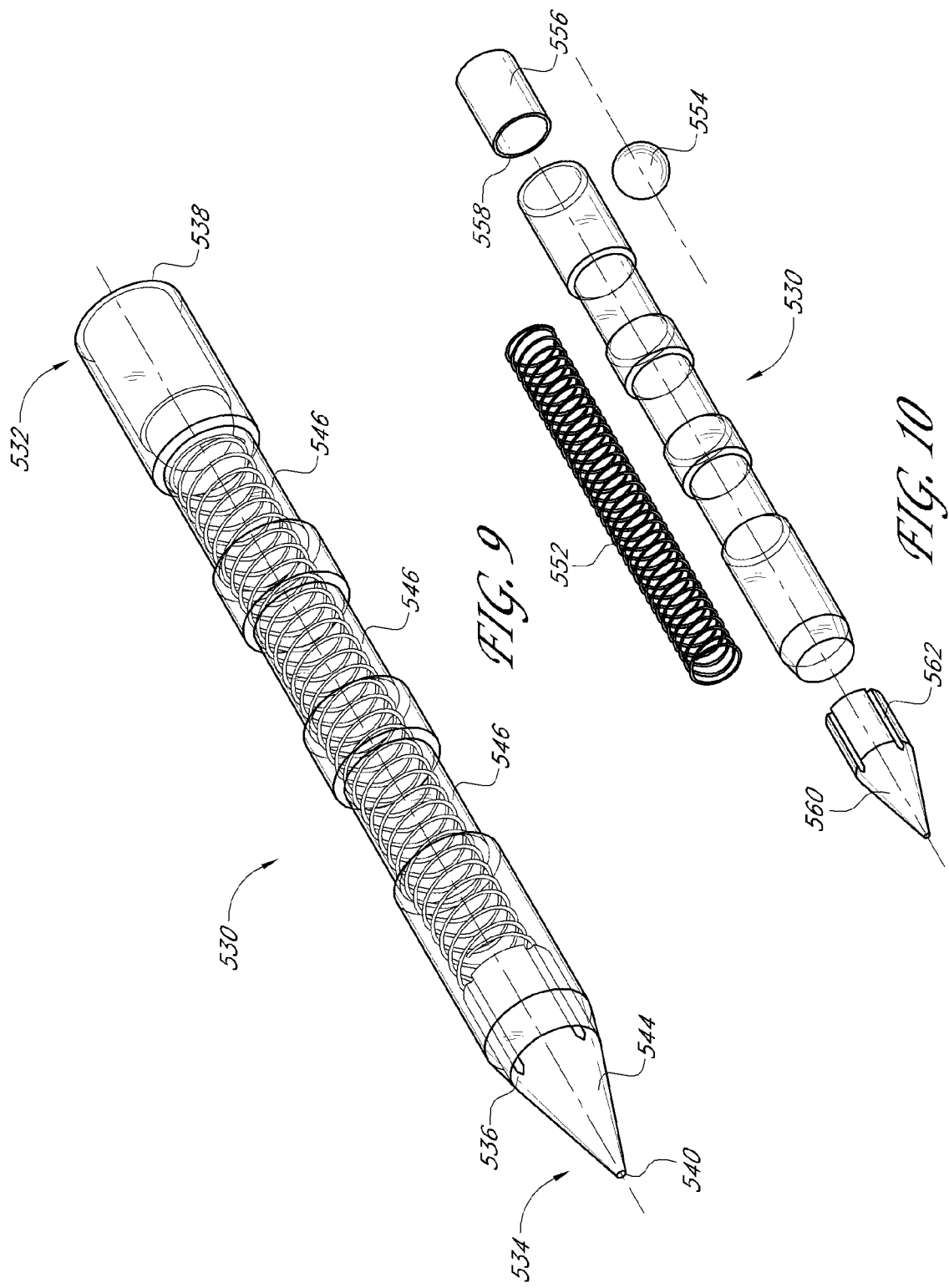

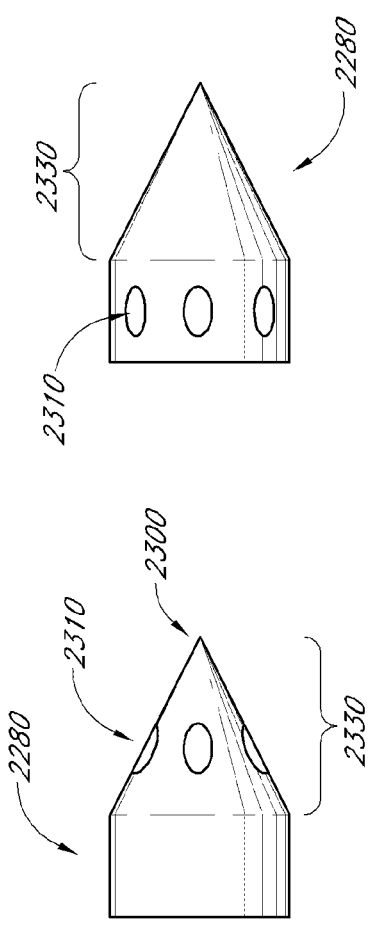
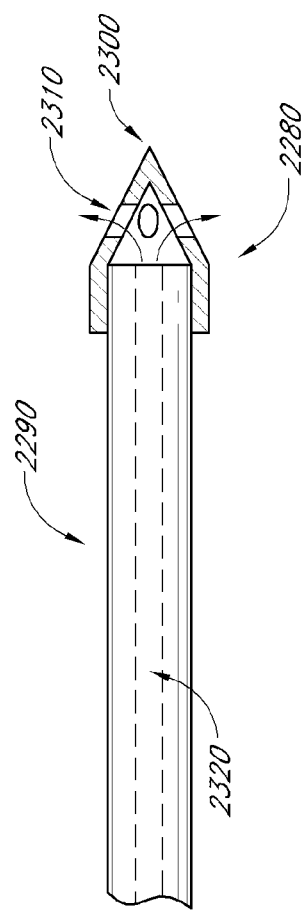
FIG. 26A
FIG. 26B
FIG. 26C

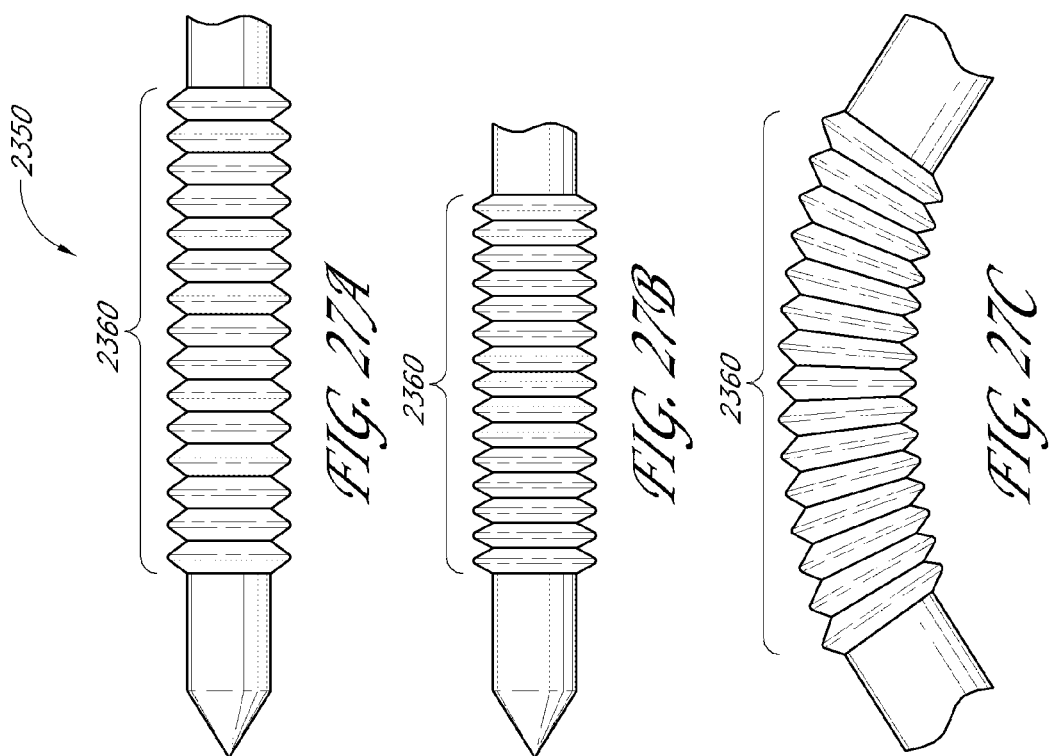

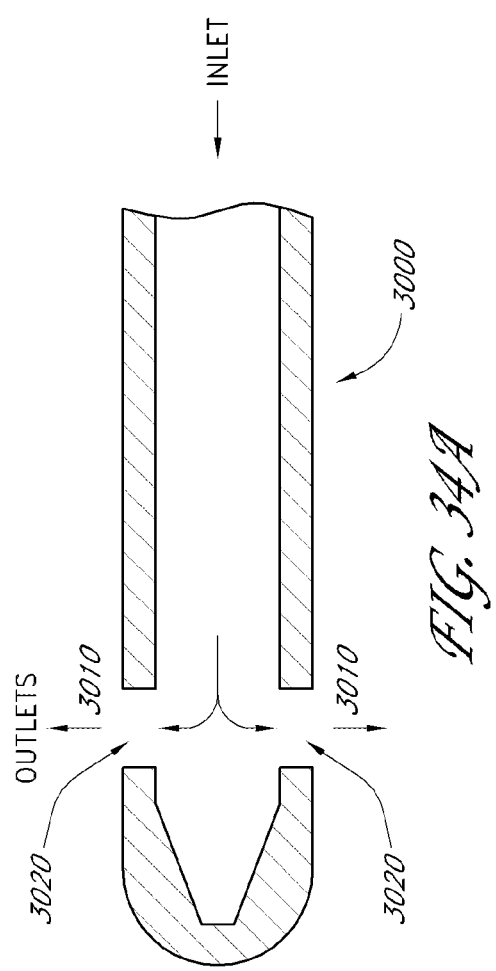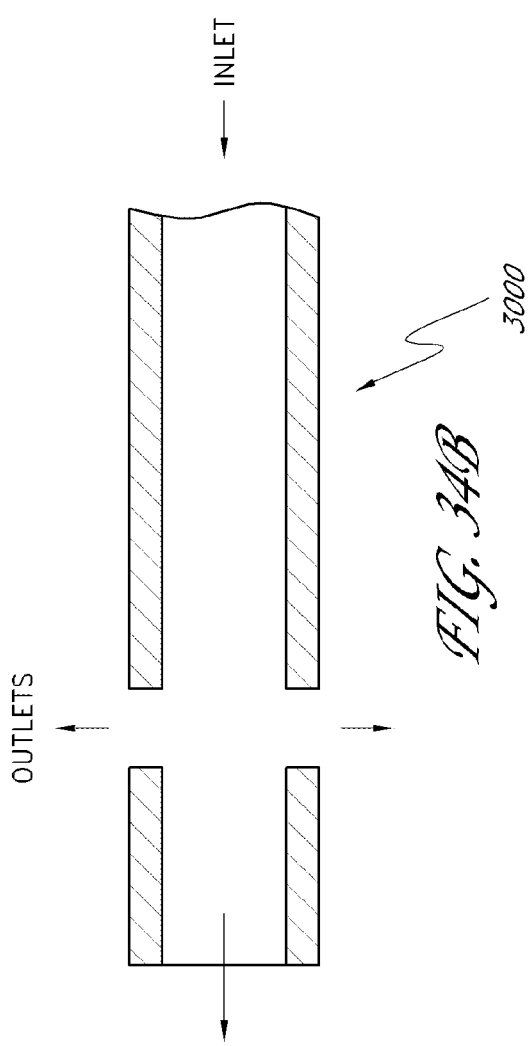

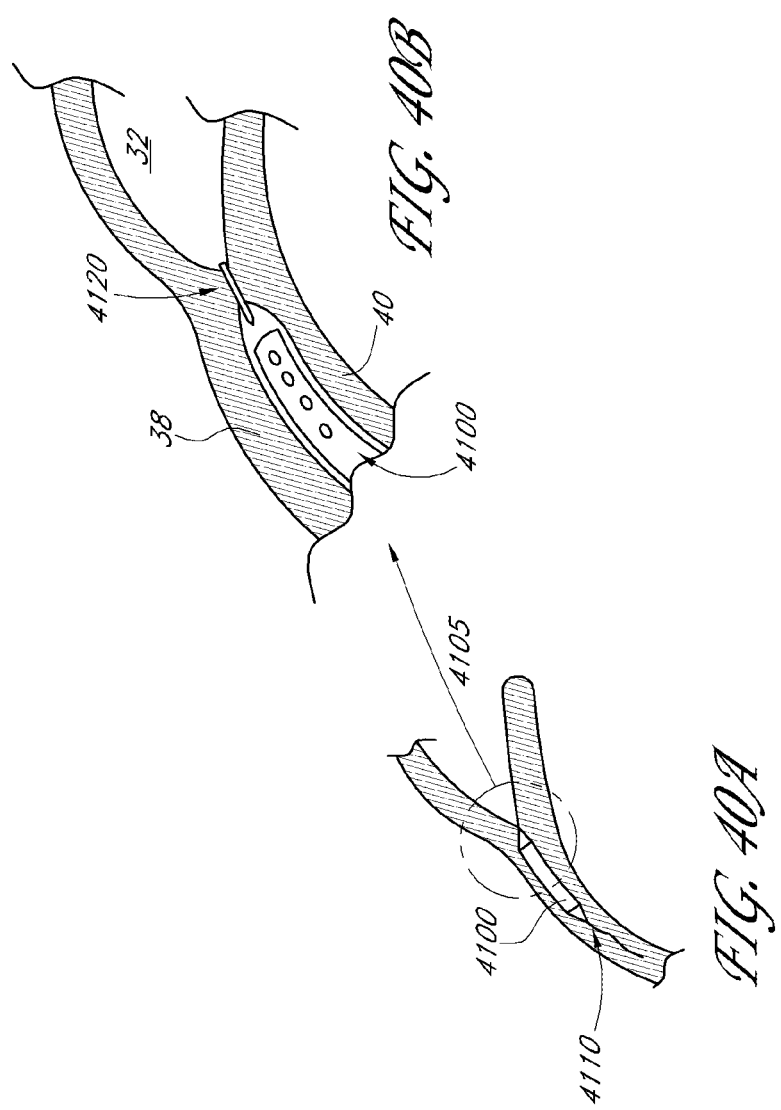

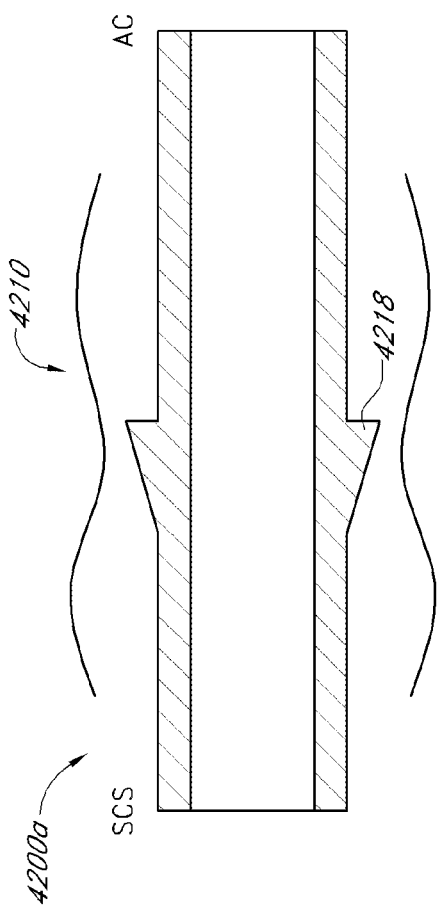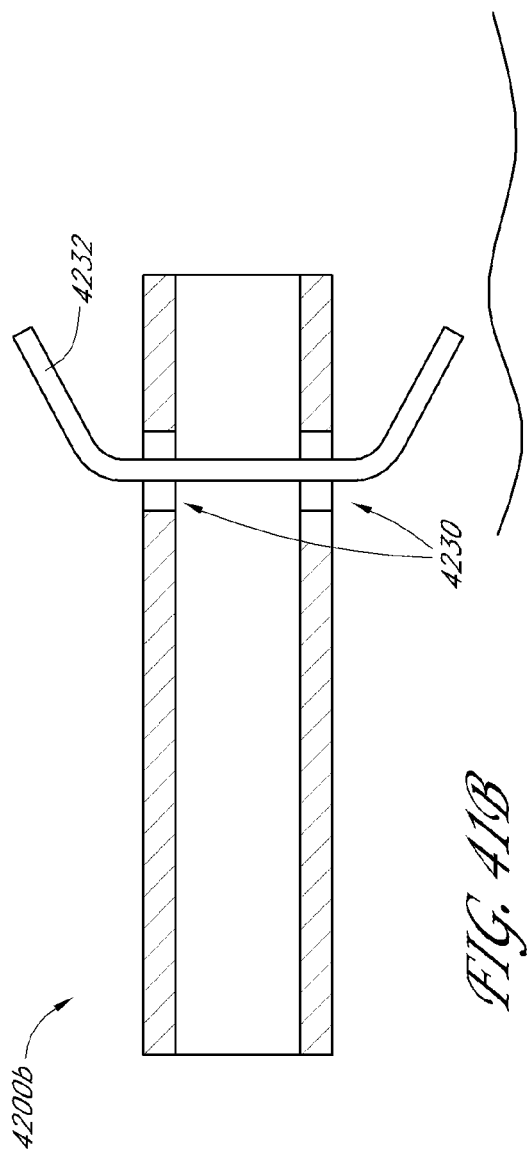
FIG. 41A
FIG. 41B

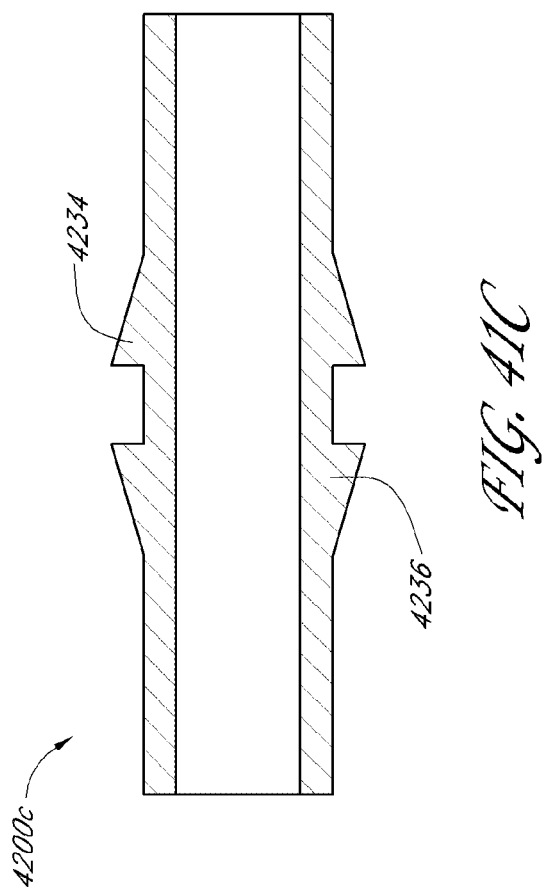

UVEOSCLERAL SHUNT AND METHODS FOR IMPLANTING SAME

RELATED CASES

This application is a continuation of U.S. patent application Ser. No. 13/964,579, filed Aug. 12, 2013, which is a continuation of U.S. patent application Ser. No. 11/938,238, filed Nov. 9, 2007, now U.S. Pat. No. 8,506,515, which claims priority and the benefit under 35 U.S.C. § 119(e) to Provisional Patent Application Ser. No. 60/857,872, filed Nov. 10, 2006, Ser. No. 60/880,091, filed Jan. 11, 2007, Ser. No. 60/890,610, filed Feb. 19, 2007, and Ser. No. 60/947,942, filed Jul. 3, 2007. Each of these disclosures is hereby incorporated by reference herein in its entirety.

BACKGROUND OF THE INVENTION

Field of the Invention

This disclosure relates to reducing intraocular pressure within the eye. This disclosure also relates to a treatment of glaucoma and/or other ocular disorders wherein aqueous humor is permitted to flow out of an anterior chamber of the eye through a surgically implanted pathway.

Description of the Related Art

A human eye is a specialized sensory organ capable of light reception and is able to receive visual images. Aqueous humor is a transparent liquid that fills at least the region between the cornea, at the front of the eye, and the lens. A trabecular meshwork, located in an anterior chamber angle, which is formed between the iris and the cornea, normally serves as a drainage channel for aqueous humor from the anterior chamber so as to maintain a balanced pressure within the anterior chamber of the eye.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork normally allows the aqueous humor (hereinafter referred to as "aqueous") to enter Schlemm's canal, which then empties into aqueous collector channels in the posterior wall of Schlemm's canal and then into aqueous veins, which form the episcleral venous system. Aqueous is continuously secreted by a ciliary body around the lens, so there is a constant flow of aqueous from the ciliary body to the anterior chamber of the eye. Pressure within the eye is determined by a balance between the production of aqueous and its exit through the trabecular meshwork (major route) and uveoscleral outflow (minor route). The portion of the trabecular meshwork adjacent to Schlemm's canal (the juxtacanalicular meshwork) causes most of the resistance to aqueous outflow.

While a majority of the aqueous leaves the eye through the trabecular meshwork and Schlemm's canal, it is believed that about 10 to about 20 percent of the aqueous in humans leaves through the uveoscleral pathway. The degree with which uveoscleral outflow contributes to the total outflow of the eye appears to be species dependent. As used herein, the term "uveoscleral outflow pathway" is to be given its ordinary and customary meaning to a person of ordinary skill in the art (and it is not to be limited to a special or customized meaning), and refers without limitation to the space or passageway whereby aqueous exits the eye by passing through the ciliary muscle bundles located angle of the anterior chamber and into the tissue planes between the choroid and the sclera, which extend posteriorly to the optic nerve. From these tissue planes, it is believed that the aqueous travels through the surrounding scleral tissue and drains via the scleral and conjunctival vessels, or is absorbed by the uveal blood vessels. It is unclear from studies whether the degree of physiologic uveoscleral outflow is pressure-dependent or pressure-independent. As used herein, the term "supraciliary space" is to be given its ordinary and customary meaning to a person of ordinary skill in the art (and it is not to be limited to a special or customized meaning), and refers without limitation to the portion of the uveoscleral pathway through the ciliary muscle and between the ciliary body and the sclera, and the term "suprachoroidal space" is to be given its ordinary and customary meaning to a person of ordinary skill in the art (and it is not to be limited to a special or customized meaning), and refers without limitation to the portion of the uveoscleral pathway between the choroid and sclera. Although it is not completely understood, some studies have suggested that there may be a "compact zone" of connective tissue associated with the junction between the retina and ciliary body, known as the ora serrata. This "compact zone" may act as a site of resistance along the uveoscleral outflow pathway. The ora serrata can vary in length from about 5.75 mm to 7.5 mm nasally to about 6.5 mm to about 8.5 mm temporally. Other studies suggest that the ciliary muscle bundles are the primary site of resistance.

Certain therapeutic agents have been shown to reduce intraocular pressure by increasing uveoscleral outflow, but the mechanism by which uveoscleral outflow is increased is unclear. Some studies have suggested that relaxation of the ciliary muscle may reduce resistance through the ciliary muscle bundles to increase flow. Other studies suggest that dilation of the post-capillary venules or constriction of the pre-capillary arterioles may reduce downstream fluid pressure and increase uveoscleral outflow.

Glaucoma is broadly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous from the anterior chamber of the eye. Open-angle glaucoma is any glaucoma in which the exit of aqueous through the trabecular meshwork is diminished while the angle of the anterior chamber remains open. For most cases of open-angle glaucoma, the exact cause of diminished filtration is unknown. Primary open-angle glaucoma is the most common of the glaucomas, and is often asymptomatic in the early to moderately advanced stages of glaucoma. Patients may suffer substantial, irreversible vision loss prior to diagnosis and treatment. However, there are secondary open-angle glaucomas that may include edema or swelling of the trabecular spaces (e.g., from corticosteroid use), abnormal pigment dispersion, or diseases such as hyperthyroidism that produce vascular congestion.

All current therapies for glaucoma are directed toward decreasing intraocular pressure. Currently recognized categories of drug therapy for glaucoma include but are not limited to: (1) Miotics (e.g., pilocarpine, carbachol, and acetylcholinesterase inhibitors), (2) Sympathomimetics (e.g., epinephrine and dipivalylepinephxine), (3) Beta-blockers (e.g., betaxolol, levobunolol and timolol), (4) Carbonic anhydrase inhibitors (e.g., acetazolamide, methazolamide and ethoxzolamide), and (5) Prostaglandins (e.g., metabolite derivatives of arachindonic acid). Medical therapy includes topical ophthalmic drops or oral medications that reduce the production of aqueous or increase the outflow of aqueous. However, drug therapies for glaucoma are sometimes associated with significant side effects. The most frequent and perhaps most serious drawback to drug therapy, especially the elderly, is patient compliance. Patients often forget to take their medication at the appropriate times or else administer eye drops improperly, resulting in under- or overdosing. Patient compliance is particularly problematic with therapeutic agents requiring dosing frequencies of three times a day or more, such as pilocarpine. Because the effects of glaucoma are irreversible, when patients dose improperly, allowing ocular concentrations to drop below appropriate therapeutic levels, further permanent damage to vision occurs. Furthermore, current drug therapies are targeted to be deposited directly into the ciliary body where the aqueous is produced. And current therapies do not provide for a continuous slow-release of the drug. When drug therapy fails, surgical therapy is pursued.

Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if ocular morbidity associated with trabeculectomy could be decreased. The current morbidity associated with trabeculectomy consists of failure (10-15%); infection (a life long risk of 2-5%); choroidal hemorrhage, a severe internal hemorrhage from low intraocular pressure, resulting in visual loss (1%); cataract formation; and hypotony maculopathy (potentially reversible visual loss from low intraocular pressure). For these reasons, surgeons have tried for decades to develop a workable surgery for reducing intraocular pressure.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Q-switched Neodymium (Nd) YAG lasers also have been investigated as an optically invasive trabeculopuncture technique for creating full-thickness holes in trabecular meshwork. However, the relatively small hole created by this trabeculopuncture technique exhibits a filling-in effect and fails.

Goniophotoablation is disclosed by Berlin in U.S. Pat. No. 4,846,172 and involves the use of an excimer laser to treat glaucoma by ablating the trabecular meshwork. This method did not succeed in a clinical trial. Hill et al. used an Erbium YAG laser to create full-thickness holes through trabecular meshwork (Hill et al., Lasers in Surgery and Medicine 11:341346, 1991). This laser trabecular ablation technique was investigated in a primate model and a limited human clinical trial at the University of California, Irvine. Although ocular morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage is an "ab interno" (from the inside), mechanically disruptive technique that uses an instrument similar to a cyclodialysis spatula with a microcurette at the tip. Initial results were similar to trabeculotomy: it failed due to repair mechanisms and a process of filling in.

Although trabeculectomy is the most commonly performed filtering surgery, viscocanalostomy (VC) and non-penetrating trabeculectomy (NPT) are two new variations of filtering surgery. These are "ab externo" (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous through the surgical opening will continue. The risk of placing a glaucoma drainage device also includes hemorrhage, infection, and diplopia (double vision).

All of the above embodiments and variations thereof have numerous disadvantages and moderate success rates. They involve substantial trauma to the eye and require great surgical skill in creating a hole through the full thickness of the sclera into the subconjunctival space. The procedures are generally performed in an operating room and involve a prolonged recovery time for vision. The complications of existing filtration surgery have prompted ophthalmic surgeons to find other approaches to lowering intraocular pressure.

Because the trabecular meshwork and juxtacanalicular tissue together provide the majority of resistance to the outflow of aqueous, they are logical targets for surgical removal in the treatment of open-angle glaucoma. In addition, minimal amounts of tissue need be altered and existing physiologic outflow pathways can be utilized. Some procedures bypass the trabecular meshwork and juxtacanalicular tissue to drain fluid to physiologic outflow channels. However, in severe cases, it has been found that these procedures do not sufficiently reduce intraocular pressure.

As reported in Arch. Ophthalm. (2000) 118:412, glaucoma remains a leading cause of blindness, and filtration surgery remains an effective, important option in controlling glaucoma. However, modifying existing filtering surgery techniques in any profound way to increase their effectiveness appears to have reached a dead end.

SUMMARY OF THE INVENTION

A need exists for an extended, site-specific treatment method for placing a drainage implant (preferably by an ab interno implantation procedure) for diverting aqueous humor in an eye from the anterior chamber to a location within the eye that will permit further reduction of intraocular pressure. One such location disclosed herein is the uveoscleral outflow pathway, which comprises the supraciliary space and/or the suprachoroidal space. In some embodiments of the present disclosure, a method is provided for implanting a drainage implant ab interno in an eye to divert aqueous humor from the anterior chamber to the supraciliary space.

In accordance with some embodiments of the present invention, a method for reducing intraocular pressure in an eye of a mammal (e.g., human) is provided, comprising introducing an ocular implant into the anterior chamber of the eye, the ocular implant having proximal and distal ends, cutting eye tissue using a distal portion of the implant at a location posterior of a scleral spur of the eye, advancing the implant from the anterior chamber into the cut eye tissue such that the distal end is located in the suprachoroidal space and the proximal end is located in the anterior chamber, and conducting aqueous humor between the proximal and distal ends of the implant.

An ocular implant is disclosed in accordance with some embodiments of the present invention. In some embodiments, the implant comprises a substantially straight, rigid, generally cylindrical body of a length no greater than 7 mm, preferably not greater than about 5 mm, and more preferably not greater than about 4 mm and not shorter than about 2 mm. The body has a tip that narrows toward an end, at least one inlet communicating with at least one inner lumen that terminates at one or more outlets. The lumen is of a sufficient length to extend from an anterior chamber to a suprachoroidal space of an eye. Means are provided for regulating fluid flow through the lumen.

A method for regulating intraocular pressure is disclosed in accordance with some embodiments of the present invention. In some embodiments, the method comprises placing an elongated implant in eye tissue with an inlet in an anterior chamber and an outlet in a uveoscleral outflow pathway of an eye, and utilizing intraocular pressure to apply a force to move a valve surface within the implant in a direction transverse to a longitudinal axis of the implant such that aqueous humor flows from the anterior chamber to the uveoscleral outflow pathway at intraocular pressures greater than a threshold pressure.

An intraocular implant is disclosed in accordance with some embodiments of the present invention. In some embodiments, the intraocular implant comprises an inlet portion that provides an ingress flow path comprising one or more influent openings that have a total cross-sectional flow area and communicate with an interior chamber within the implant, an outlet portion providing an egress flow path comprising one or more effluent openings, and a pressure regulation valve having a deflectable plate or diaphragm with a surface area exposed to fluid within the interior chamber. The surface area is substantially greater than the total cross-sectional flow area. The valve is disposed between the interior chamber and the one or more effluent openings such that movement of the deflectable plate regulates flow from the interior chamber to the one or more effluent openings. The plate extends in a direction generally parallel to the inlet flow path and to the outlet flow path.

A method of performing surgery to lower intraocular pressure of an eye is disclosed in accordance with some embodiments of the present invention. In some embodiments, the method comprises providing an opening into an anterior chamber of the eye, inserting an instrument into the anterior chamber through said opening to perform a cataract extraction from the eye, providing an ocular implant having an inflow portion in fluid communication with an outflow portion, transporting the ocular implant from the opening through the anterior chamber of the eye to the anterior chamber angle of the eye, positioning the ocular implant such that the inflow portion of the ocular implant is positioned in the anterior chamber and the outflow portion of the ocular implant is positioned in the suprachoroidal space, and permitting aqueous humor to flow from the anterior chamber of the eye through the inflow portion of the ocular implant to the outflow portion of the ocular implant and into the suprachoroidal space of the eye.

A system for treating an ocular disorder in a patient is disclosed in accordance with some embodiments of the present invention. In some embodiments, the system comprises a drainage implant which, following implantation at an implantation site, conducts fluid from the anterior chamber to a uveoscleral outflow pathway, such as the supraciliary space and a delivery instrument for implanting the drainage implant. The instrument has a distal end sufficiently sharp to penetrate eye tissue at an insertion site near the limbus of the patient's eye, and is sufficiently long to advance the implant transocularly from the insertion site across the anterior chamber to the implantation site. The instrument also has a sufficiently small cross section such that the insertion site self seals without suturing upon withdrawal of the instrument from the eye. The instrument comprises a plurality of members longitudinally moveable relative to each other and a seal between the members to prevent aqueous humor from passing between the members proximal the seal when the instrument is in the eye.

A system for treating an ocular disorder in a patient is disclosed in accordance with some embodiments of the present invention. In some embodiments, the system comprises a shunt that includes a central lumen that terminates at an outlet opening at a distal end of the shunt and a delivery instrument for implanting the shunt. The shunt further includes a transitional region that continually decreases in the radial dimension toward the distal end. The shunt also has a sufficient length such that, following implantation at an implantation site, the lumen conducts fluid from the anterior chamber to a uveoscleral outflow pathway of an eye. The delivery instrument comprises an outer needle, an implantation member and a trocar. The outer needle has a distal end sufficiently sharp to penetrate eye tissue at an insertion site near the limbus of the patient's eye. The implantation member is sufficiently long to advance the shunt transocularly from the insertion site across the anterior chamber to the implantation site, and is movable along an axis of the delivery instrument. The trocar cooperates with the implantation member and is movable relative to the implantation member. The trocar is sized to extend through the central lumen of the shunt and has a distal portion that narrows toward a distal end of the trocar. The distal end of the trocar is rounded.

A method for treating glaucoma is disclosed in accordance with some embodiments of the present invention. In some embodiments, the method comprises forming as incision in eye tissue located near the limbus of the eye, introducing a delivery instrument through the incision, the delivery instrument carrying a drainage device, implanting the drainage device in eye tissue at a location posterior of a scleral spur of the eye, without introducing a viscoelectic material into the anterior chamber, to establish a flow path for aqueous humor from the anterior chamber to a physiologic outflow path, and withdrawing the delivery instrument from the eye, wherein the incision is sufficient small that it is self-sealing once the delivery instrument is withdrawn.

A method for lowering intraocular pressure in a patient having at least one ocular shunt implanted in the trabecular meshwork to drain aqueous humor from the anterior chamber towards Schlemm's canal is disclosed in accordance with some embodiments of the present invention. In some embodiments, the method comprises introducing a drainage device through tissue adjacent the limbus into the anterior chamber, advancing the drainage device across the anterior chamber to a location near the scleral spur, and implanting the drainage device in eye tissue at a location spaced from the at least one ocular shunt and the trabecular meshwork to establish a flow path from the anterior chamber towards the suprachoroidal space.

A further aspect of the invention involves a system for treating glaucoma. The system comprises a plurality of implants, each implant has a distal end sufficiently sharp to extend through tissue into a physiologic outflow pathway, and an instrument that has a chamber in which the implants are loaded for serial delivery into eye tissue. At least a first implant of the plurality of implants includes a recess that is sized to receive a distal end of a second implant of the plurality of implants. The recess is shaped so that with the implants contacting each other when placed in tandem in the instrument, the distal end of the second implant does not bear against the first implant.

Further aspects, features and advantages of the present invention will become apparent from the detailed description of the preferred embodiments of ocular implants, methods of implantation, and treatment courses that follow.

BRIEF DESCRIPTION OF THE DRAWINGS

These and other features, aspects, and advantages of the present disclosure will now be described with reference to the drawings of embodiments, which embodiments are intended to illustrate and not to limit the disclosure.

FIG. 2 illustrates a schematic cross-sectional view of an eye with a delivery device being advanced adjacent the anterior chamber angle. The size of the shunt is exaggerated for illustration purposes.

FIG. 3 illustrates a schematic cross-section view of an eye with a delivery device implanting an implant that extends between the anterior chamber and the uveoscleral outflow pathway.

FIG. 4 illustrates a drainage implant in accordance with embodiments disclosed herein.

FIG. 5 illustrates another drainage implant in accordance with embodiments disclosed herein.

FIG. 6 illustrates another drainage implant in accordance with embodiments disclosed herein.

FIG. 7 illustrates another drainage implant in accordance with embodiments disclosed herein including a core extending through a lumen of the implant.

FIG. 8 illustrates the implant of FIG. 7 with the core removed from the lumen of the implant.

FIG. 9 illustrates another drainage implant in accordance with embodiments disclosed herein including a ball-check pressure regulator.

FIG. 10 illustrates an exploded view of the implant of FIG. 9.

FIGS. 26A-C illustrates another drainage implant in accordance with embodiments disclosed herein including a cap.

FIGS. 27A-C illustrates another drainage implant in accordance with embodiments disclosed herein including a flexible portion.

FIGS. 34A and 34B are cross-sectional views of a shunt with side ports.

FIGS. 40A and 40B illustrate sectional views of the implant of FIG. 39 and an associated drainage implant as implanted into any eye in accordance with embodiments disclosed herein.

FIGS. 41A to 41H illustrate cross-sectional views of other drainage implants in accordance with embodiments disclosed herein.

DETAILED DESCRIPTION OF THE PREFERRED EMBODIMENTS

Figure 1:
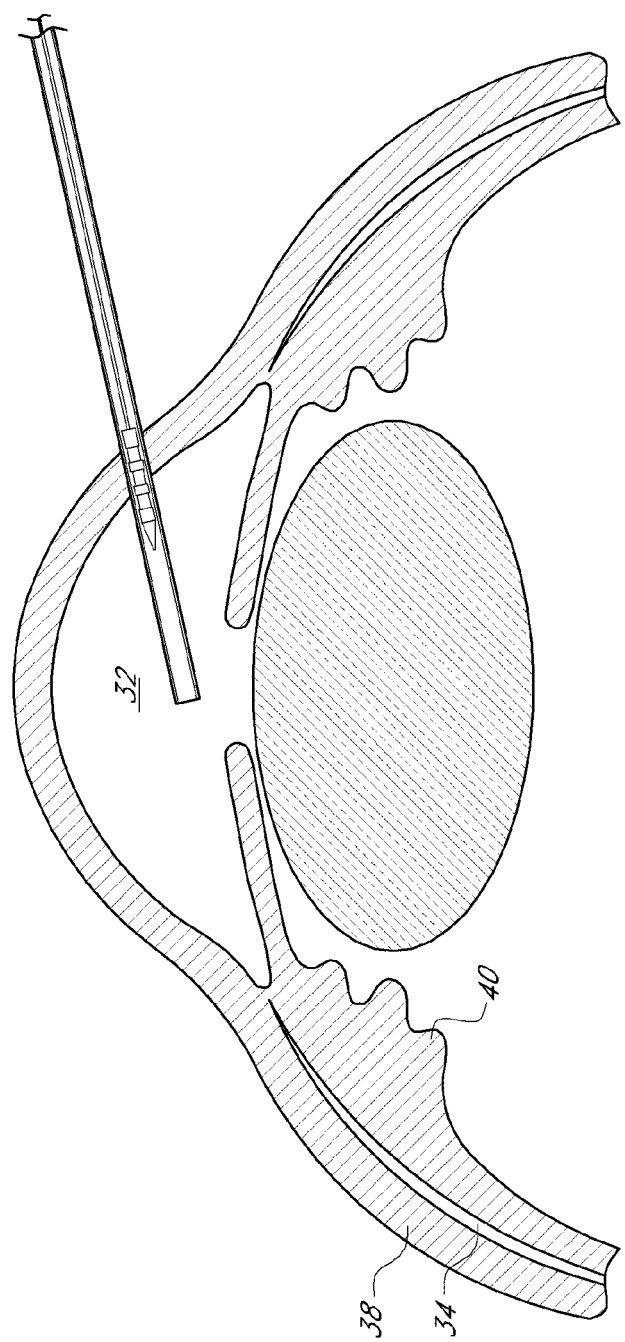
FIG. 1 illustrates a schematic cross-sectional view of an eye with a delivery device containing an implant being advanced across the anterior chamber.

An ophthalmic implant system is provided that comprises a shunt and a delivery instrument for implanting the shunt. While this and other systems and associated methods are described herein in connection with glaucoma treatment, the disclosed systems and methods can be used to treat other types of ocular disorders in addition to glaucoma.

The shunt, following implantation at an implantation site, drains fluid from the anterior chamber into a physiologic outflow space. In some embodiments, the shunt is configured to provide a fluid flow path for draining aqueous humor from the anterior chamber of an eye to the uveoscleral outflow pathway to reduce intraocular pressure. In some embodiments, an instrument is provided for delivering and/or implanting the drainage shunt ab interno in an eye to divert aqueous humor from the anterior chamber to the uveoscleral outflow pathway. In some embodiments, a method is provided for implanting a drainage shunt ab interno in an eye to divert aqueous humor from the anterior chamber to the uveoscleral outflow pathway. In some embodiments, the aqueous humor is diverted to the supraciliary space or the suprachoroidal space of the uveoscleral outflow pathway.

The term "shunt" as used herein is a broad term, and is to be given its ordinary and customary meaning to a person of ordinary skill in the art (and it is not to be limited to a special or customized meaning), and refers without limitation to an implant defining one or more fluid passages. The fluid passage(s) in some embodiments remains patent and, in other embodiments, the passage(s) is fully or partially occluded under at least some circumstances (e.g., at lower intraocular pressure levels). The shunts may feature a variety of characteristics, described in more detail below, which facilitate the regulation of intraocular pressure. The mechanical aspects and material composition of the shunt can be important for controlling the amount and direction of fluid flow. Therefore, various examples of shunt dimensions, features, tip configurations, material flexibility, coatings, and valve design, in accordance with some embodiments of the present disclosure, are discussed in detail below.

The delivery instruments, described in more detail below, may be used to facilitate delivery and/or implantation of the shunt to the desired location of the eye. The delivery instrument preferably is used to place the shunt into a desired position by application of a continual implantation force, by tapping the shunt into place using a distal portion of the delivery instrument, or by a combination of these methods. The design of the delivery instruments may take into account, for example, the angle of implantation and the location of the shunt relative to an incision. For example, in some embodiments, the delivery instrument may have a fixed geometry, be shape-set, or actuated. In some embodiments, the delivery instrument may have adjunctive or ancillary functions. In some embodiments, the delivery instrument may additionally be used to, for example, inject dye and/or viscoelastic fluid, to dissect, or be used as a guidewire.

The shunt can be advanced through the ciliary attachment tissue, which lies to the posterior of the scleral spur, during implantation. This tissue typically is fibrous or porous, which is relatively easy to pierce or cut with a surgical device, and lies inward of the scleral spur. The shunt can be advanced through this tissue and abut against the sclera once the shunt extends into the uveoscleral outflow pathway. The shunt can then slide within the uveoscleral outflow pathway along the interior wall of the sclera. As the shunt is advanced into the uveoscleral outflow pathway and against the sclera, the shunt will likely be oriented at an angle with respect to the interior wall of the sclera. The shunt is advanced until it reaches the desired implantation site within the uveoscleral outflow pathway. In some embodiments, the shunt is advanced into the ciliary body or ciliary muscle bundles to achieve drainage into the supraciliary space. In other embodiments, the shunt is advanced through the ciliary body or ciliary muscle bundles to achieve fluid communication between the anterior chamber and the suprachoroidal space. In still other embodiments, the shunt is advanced into the compact zone or through the compact to drain aqueous humor into the more distal portions of the suprachoroidal space.

Shunts

The disclosed embodiments include shunts that provide a fluid flow path for conducting aqueous humor from the anterior chamber of an eye to the uveoscleral outflow pathway to reduce intraocular pressure, preferably below episcleral venous pressure without hypotony. The shunts can have an inflow portion and an outflow portion. The outflow portion of the shunt preferably is disposed at or near a distal end of the shunt. When the shunt is implanted, the inflow portion may be sized and configured to reside in the anterior chamber of the eye and the outflow portion may be sized and configured to reside in the uveoscleral outflow pathway. In some embodiments, the outflow portion may be sized and configured to reside in the supraciliary region of the uveoscleral outflow pathway or in the suprachoroidal space.

One or more lumens can extend through the shunt to form at least a portion of the flow path. Preferably, there is at least one lumen that operates to conduct the fluid through the shunt. Each lumen preferably extends from an inflow end to an outflow end along a lumen axis. In some embodiments the lumen extends substantially through the longitudinal center of the shunt. In other embodiments, the lumen can be offset from the longitudinal center of the shunt. In still other embodiments, the flow path can be defined by grooves, channel or reliefs formed on an outer surface of the shunt body.

One or more openings can extend through the wall of the shunt. In some embodiments, the openings can extend through a middle portion of the shunt. In other embodiments the openings can extend through other portions of the shunt.

The openings can be one or more of a variety of functions. One such function is that when the shunt is inserted into the suprachoroidal or supraciliary space, the openings provide a plurality of routes through which the aqueous humor can drain. For example, once the shunt is inserted into the eye, if the shunt only has one outflow channel (e.g., one end of a lumen), that outflow channel can be plugged, for example, by the shunt's abutment against the interior surface of the sclera or the outer surface of the choroid. Additionally, the outflow channel can be clogged with tissue that is accumulated or cored during the advancement of the shunt through the fibrous or porous tissue. A plurality of openings provides a plurality of routes through which the fluid may flow to maintain patency and operability of the drainage shunt. In embodiments where the shunt has a porous body, the openings can define surface discontinuities to assist in anchoring the shunt once implanted.

The shunt in some embodiments can include a distal portion that is sufficiently sharp to pierce eye tissue near the scleral spur of the eye, and that is disposed closer to the outlet portion than to the inlet portion. In some embodiments, the distal portion is located at the distal end of the implant. The distal portion can be sufficiently blunt so as not to substantially penetrate scleral tissue of the eye. In some embodiments, the shunts have a generally sharpened forward end and are self-trephinating, i.e., self-penetrating, so as to pass through tissue without pre-forming an incision, hole or aperture. The sharpened forward end can be, for example, conical or tapered. The tip can be sufficiently sharp to pierce eye tissue near the scleral spur of the eye. The tip also can be sufficiently blunt so as not to substantially penetrate scleral tissue of the eye. The taper angle of the sharpened end can be, for example, about 30°±15° in some embodiments. The radius of the tip can be about 70 to about 200 microns. In other embodiments, where an outlet opening is formed at the distal end of the shunt, the distal portion gradually increases in cross-sectional size in the proximal direction, preferably at a generally constant taper or radius or in a parabolic manner.

The body of the shunt can include at least one surface irregularity. The surface irregularity can comprise, for example, a ridge, groove, relief, hole, or annular groove. The surface discontinuities or irregularities can also be formed by barbs or other projections, which extend from the outer surface of the shunt, to inhibit migration of the shunt from its implanted position. In some embodiments, the projections may comprise external ribbing to resist displacement of the shunt. The surface irregularity in some embodiments can interact with the tissue of the interior wall of the sclera and/or with the tissue of the ciliary attachment tissue. In some embodiments, the shunts are anchored by mechanical interlock between tissue and an irregular surface and/or by friction fit. In other embodiments, the shunt includes cylindrical recessed portions (e.g., annular groves) along an elongate body to provide enhanced gripping features during implantation and anchoring following implantation within the eye tissue.

The shunt may also incorporate fixation features, such as flexible radial (i.e., outwardly extending) extensions. The extensions may be separate pieces attached to the shunt, or may be formed by slitting the shunt wall, and thermally forming or mechanically deforming the extensions radially outward. If the extensions are separate pieces, they may be comprised of flexible material such as nitinol or polyimide. The extensions may be located at the proximal or distal ends of the shunt, or both, to prevent extrusion of the shunt from its intended location. The flexibility of the fixation features will facilitate entry through the corneal incision, and also through the ciliary muscle attachment tissue.

In some embodiments, the body of the shunt has an outlet opening on a side surface to allow fluid flow. In some embodiments, the body of the shunt has a plurality of outlet openings on a side surface to allow fluid flow. In other embodiments, there is a plurality of outlet openings at one end of the shunt, such as the distal end. The openings can facilitate fluid flow through the shunt.

The shunt may have a cap, or tip, at one end. The cap can include a tissue-piercing end and one or more outlet openings. Each of the one or more outlet openings can communicate with at least one of the one or more lumens. In some embodiments the cap can have a conically shaped tip with a plurality of outlet openings disposed proximal of the tip's distal end. In other embodiments, the cap can have a tapered angle tip. The tip can be sufficiently sharp to pierce eye tissue near the scleral spur of the eye. The tip also can be sufficiently blunt so as not to substantially penetrate scleral tissue of the eye. In some embodiments, the conically shaped tip facilitates delivery of the shunt to the desired location. In some embodiments, the cap has an outlet opening on a side surface to allow fluid flow. In some embodiments, the cap has a plurality of outlet openings on a side surface to allow fluid flow. In other embodiments, there is a plurality of outlet openings on the conical surface of the cap. The openings on the cap can facilitate fluid flow through the shunt. The opening may provide an alternate route for fluid flow which is beneficial in case the primary outflow portion of the shunt becomes blocked.

In some embodiments, multiple shunts are configured to be delivered during a single procedure. In some embodiments when multiple shunts are delivered, the shunts are arranged tandemly. The shunt can include a tip protector at one end. The tip protector can comprise a recess shaped to receive and protect, for example, the tip of an adjacent shunt. In some embodiments, the tip of the adjacent shunt has a conical shape. The recess may be shaped to contact the sides of the conical tip while protecting the more tapered tip, or end, from impact. The tip protector is particularly useful for delivery of multiple shunts.

The shunts may be of varied lengths to optimize flows. In some preferred embodiments, the shunt has sufficient length such that the outflow portion resides in the suprachoroidal space and the inflow portion is exposed to the anterior chamber. In other preferred embodiments, the length of the shunt is a length such that the outflow portion resides in the supraciliary space of the uveoscleral outflow pathway. In some embodiments, the length of the shunt is a length such that the outflow portion resides in the membranous region of the uveoscleral outflow pathway adjacent to the retina, while in other embodiments, the shunt has a length that extends distally past the membranous region. In some embodiments, the length of the shunt from the portion residing in the anterior chamber to the portion residing in the uveoscleral outflow pathway may be about 0.5 mm to about 5 mm. In preferred embodiments, the length of the shunt may be about 1.5 mm to about 5 mm. In more preferred embodiments, the length of the shunt may be about 2.0 mm. In some embodiments, the length of the shunt is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mm.

The shunt can have an outer diameter that will permit the shunt to fit within a 23-gauge needle during implantation. The shunt can also have a diameter that is designed to be inserted with larger needles. For example, the shunt can also be delivered with 18-, 19- or 20-gauge needles. In other embodiments, smaller gauge applicators, such as a 23-gauge (or smaller) applicator, may be used. The shunt can have a substantially constant cross-sectional shape through most of the length of the shunt, or the shunt can have portions of reduced or enlarged cross-sectional size (e.g., diameter), or cylindrical channels, e.g., annular grooves, disposed on the outer surface between the proximal end and the distal end. The distal end of the shunt can have a tapered portion, or a portion having a continually decreasing radial dimension with respect to the lumen axis along the length of the axis. The tapered portion preferably in some embodiments terminates with a smaller radial dimension at the outflow end. During implantation, the tapered portion can operate to form, dilate, and/or increase the size of, an incision or puncture created in the tissue. The tapered portion may have a diameter of about 23 gauge to about 30 gauge, and preferably about 25 gauge.

The diameter of one or more drainage lumens within the shunt may be varied to alter flow characteristics. The cross-sectional size of a shunt may be, for example, 0.1 mm to about 1.0 mm, or preferably about 0.3 mm to about 0.4 mm. A small cross-sectional size can be used to restrict flow. The cross-sectional shape of the shunt or a shunt may be any of a variety of cross-sectional shapes suitable for allowing fluid flow. For example, the cross-sectional shape of the shunt or shunt may be circular, oval, square, trapezoidal, rectangular, or any combination thereof.

In some embodiments, the shunt is configured to expand, either radially or axially, or both radially and axially. In some embodiments, the shunt may be self-expanding. In other embodiments, the shunt may be expanded by, for example, using a balloon device.

The structure of the shunt may be flexible. At least a portion of the structure of the shunt may be flexible, or the whole structure may be flexible. In some embodiments, the structure of the shunt is accordion- or balloon-like. This pleated like structure provides flexibility. In other embodiments, at least a portion of the shunt is curved. In some embodiments, at least a portion of the shunt is straight. In some embodiments, the shunt has both curved and straight portions, and in some embodiments, the shunt is generally rigid (i.e., maintains its preformed shape when implanted).

The shunt is preferably made of one or more biocompatible materials. Suitable biocompatible materials include polypropylene, polyimide, glass, nitinol, polyvinyl alcohol, polyvinyl pyrrolidone, collagen, chemically-treated collagen, polyethersulfone (PES), poly(styrene-isobutyl-styrene), Pebax, acrylic, polyolefin, polysilicon, polypropylene, hydroxyapatite, titanium, gold, silver, platinum, other metals, ceramics, plastics and a mixture thereof. The shunts can be manufactured by conventional sintering, micro machining, laser machining, and/or electrical discharge machining.

In some embodiments, the shunt is made of a flexible material. In other embodiments, the shunt is made of a rigid material. In some embodiments, a portion of the shunt is made from flexible material while another portion of the shunt is made from rigid material. The body can have an outer surface of which at least a portion is porous. Some embodiments include porosity that can be varied by masking a portion of the exterior with a band. Where the shunts include a porous body, the cross-section and porosity can be calibrated (down to 0.5 micrometers) to control the flow rates of aqueous humor through the shunt.

In some embodiments, at least a portion of the shunt (e.g., an internal spine or an anchor) is made of a material capable of shape memory. A material capable of shape memory may be compressed and, upon release, may expand axially or radially, or both axially and radially, to assume a particular shape. In some embodiments, at least a portion of the shunt has a preformed shape. In other embodiments, at least a portion of the shunt is made of a superelastic material. In some embodiments, at least a portion of the shunt is made up nitinol. In other embodiments, at least a portion of the shunt is made of a deformable material.

The body of the shunt can comprise material that includes a therapeutic agent, and/or can house, anchor, or support a therapeutic agent, or can include a coating. The coating can include a therapeutic agent. The coatings can be, for example, a drug eluting coating, an antithrombogenic coating, and a lubricious coating. The therapeutic agent can be selected from the group consisting of: heparin, TGF-beta, an intraocular pressure-lowering drug, and an anti-proliferative agent. Materials that may be used for a drug-eluting coating include parylene C, poly (butyl methacrylate), poly (methyl methacrylate), polyethylene-co-vinyl acetate, and other materials known in the art.

The shunt can further comprise a biodegradable material in or on the shunt. The biodegradable material can be selected from the group consisting of poly(lactic acid), polyethylene-vinyl acetate, poly(lactic-co-glycolic acid), poly(D,L-lactide), poly(D,L-lactide-co-trimethylene carbonate), collagen, heparinized collagen, poly(caprolactone), poly(glycolic acid), and a copolymer. All or a portion of the shunt may be coated with a therapeutic agent, e.g. with heparin, preferably in the flow path, to reduce blood thrombosis or tissue restenosis.

The flow path through the shunt can be configured to be regulated to a flow rate that will reduce the likelihood of hypotony in the eye. In some embodiments, the intraocular pressure is maintained at about 8 mm Hg. In other embodiments, the intraocular pressure is maintained at pressures less than about 8 mmHg, for example the intraocular pressure may be maintained between about 6 mm Hg and about 8 mm Hg. In other embodiments, the intraocular pressure is maintained at pressures greater than about 8 mm Hg. For example, the pressures may be maintained between about 8 mmHg and about 18 mm Hg, and more preferably between 8 mm Hg and 16 mm Hg, and most preferably not greater than 12 mm Hg. In some embodiments, the flow rate can be limited to about 2.5 μL/min or less. In some embodiments the flow rate can be limited to between about 1.9 μL/min and about 3.1 μL/min.

For example, the Hagen-Poiseuille equation suggests that a 4 mm long stent at a flow rate of 2.5 μL/min should have an inner diameter of 52 mm to create a pressure gradient of 5 mm Hg above the pressure in the suprachoroidal space.

The shunt may or may not comprise means for regulating fluid flow through the shunt. Means for regulating fluid flow can include flow restrictors, pressure regulators, or both. Alternatively, in some embodiments the shunt has neither a flow restrictor nor a pressure regulator. Regulating flow of aqueous humor can comprise varying between at least first and second operational states in which aqueous humor flow is more restricted in a first state and less restricted in a second state. Increasing the restriction to flow when changing from the second state to the first state can involve moving a valve toward a valve seat in a direction generally parallel or generally normal to a line connecting the proximal and distal ends of the shunt.

As noted above, the outflow portion of the shunt, in some embodiments is sized and configured to reside in the supraciliary region of the uveoscleral outflow pathway. In such embodiments, there is a lesser need for means for regulating fluid flow through the shunt.

The means for flow restriction may be, for example, a valve, a long lumen length, small lumen cross section, or any combination thereof. In some embodiments, the flow of fluid is restricted by the size of a lumen within the shunt, which produces a capillary effect that limits the fluid flow for given pressures. The capillary effect of the lumen allows the shunt to restrict flow and provides a valveless regulation of fluid flow.

The flow path length may be increased without increasing the overall length of the shunt by creating a lumen with a spiral flow path. A lumen within the shunt is configured to accommodate placement therein of a spiral flow channel core that is configured to provide preferred flow restriction. In effect, the spiral flow channel provides an extended path for the flow of fluid between the inlet(s) and outlet(s) of the shunt that is greater than a straight lumen extending between the ends of the shunt. The extended path provides a greater potential resistance of fluid flow through the shunt without increasing the length of the shunt. The core could have a single spiral flow channel, or a plurality of spiral flow channels for providing a plurality of flow paths through which fluid may flow through the shunt. For example, the core can have two or more spiral flow channels, which can intersect.

In some embodiments, the means for flow regulation comprises a pressure regulating valve. The valve can open when fluid pressure within the anterior chamber exceeds a preset level. Intraocular pressure may be used to apply a force to move a valve surface within the shunt in a direction transverse to a longitudinal axis of the shunt such that aqueous humor flows from the anterior chamber to the uveoscleral outflow pathway at intraocular pressures greater than a threshold pressure.

A shunt may have any number of valves to restrict flow and/or regulate pressure. The valve is preferably located between the anterior chamber and one or more effluent openings such that movement of the valve regulates flow from the interior chamber to the one or more effluent openings. A variety of valves are useful with the shunt for restricting flow. In some embodiments, the valve is a unidirectional valve and/or is a pressure relief valve. The pressure relief valve can comprise a ball, a ball seat and a biasing member urging the ball towards the ball seat. In some embodiments, the valve is a reed-type valve. In a reed valve, for example, one end of the valve may be fixed to a portion of the shunt. The body of the reed valve is capable of being deflected in order to allow flow. Pressure from fluid in the anterior chamber can deflect the body of the reed valve, thereby causing the valve to open.

In some embodiments, the shunt includes a pressure regulation valve having a deflectable plate or diaphragm with a surface area exposed to fluid within the interior chamber, the surface area being substantially greater than the total cross-sectional flow area of the one or more influent openings of the shunt. Such a valve can be disposed between an interior chamber of the shunt and the one or more effluent openings such that movement of the deflectable plate regulates flow from the interior chamber to the one or more effluent openings. The plate can extend in a direction generally parallel to the inlet flow path and to the outlet flow path.

When the intraocular pressure exceeds a particular pressure, the check pressure relief valve will open and permit fluid to flow between the anterior chamber and the uveoscleral outflow pathway. When the intraocular pressure reaches a second, lower pressure, the valve will close and limit or inhibit fluid from being conducted to the suprachoroidal space. The valve will remain closed until the intraocular pressure again reaches the particular pressure, and at which time the valve will reopen to permit or enhance drainage of fluid to the uveoscleral outflow pathway. Accordingly, the shunt provides drainage of the anterior chamber through the shunt based on the intraocular pressure levels and reduces the likelihood for over-draining the anterior chamber and causing hypotony.

Delivery Instruments

Another aspect of the systems and methods described herein relates to delivery instruments for implanting a shunt for draining fluid from the anterior chamber into a physiologic outflow space. In some embodiments, the shunt is inserted from a site transocularly situated from the implantation site. The delivery instrument can be sufficiently long to advance the shunt transocularly from the insertion site across the anterior chamber to the implantation site. At least a portion of the instrument can be flexible. Alternatively, the instrument can be rigid. The instrument can comprise a plurality of members longitudinally moveable relative to each other. In some embodiments, at least a portion of the delivery instrument is curved or angled. In some embodiments, a portion of the delivery instrument is rigid and another portion of the instrument is flexible.

In some embodiments, the delivery instrument has a distal curvature. The distal curvature of the delivery instrument may be characterized as a radius of approximately 10 to 30 mm, and preferably about 20 mm.

In some embodiments, the delivery instrument has a distal angle. The distal angle may be characterized as approximately 90 to 170 degrees relative to an axis of the proximal segment of the delivery instrument, and preferably about 145 degrees. The angle can incorporate a small radius of curvature at the "elbow" so as to make a smooth transition from the proximal segment of the delivery instrument to the distal segment. The length of the distal segment may be approximately 0.5 to 7 mm, and preferably about 2 to 3 mm.

In some embodiments, the instruments have a sharpened forward end and are self-trephinating, i.e., self-penetrating, so as to pass through tissue without pre-forming an incision, hole or aperture. Alternatively, a trocar, scalpel, or similar instrument can be used to pre-form an incision in the eye tissue before passing the shunt into such tissue.

For delivery of some embodiments of the ocular shunt, the instrument can have a sufficiently small cross section such that the insertion site self seals without suturing upon withdrawal of the instrument from the eye. An outer diameter of the delivery instrument preferably is no greater than about 18 gauge and is not smaller than about 27 gauge.

For delivery of some embodiments of the ocular shunt, the incision in the corneal tissue is preferable made with a hollow needle through which the shunt is passed. The needle has a small diameter size (e.g., 18 or 19 or 20 or 21 or 22 or 23 or 24 or 25 or 26 or 27 gauge) so that the incision is self sealing and the implantation occurs in a closed chamber with or without viscoelastic. A self-sealing incision also can be formed using a conventional "tunneling" procedure in which a spatula-shaped scalpel is used to create a generally inverted V-shaped incision through the cornea. In a preferred mode, the instrument used to form the incision through the cornea remains in place (that is, extends through the corneal incision) during the procedure and is not removed until after implantation. Such incision-forming instrument either can be used to carry the ocular shunt or can cooperate with a delivery instrument to allow implantation through the same incision without withdrawing the incision-forming instrument. Of course, in other modes, various surgical instruments can be passed through one or more corneal incisions multiple times.

Once into the anterior chamber, a delivery instrument can be advanced from the insertion site transocularly into the anterior chamber angle and positioned at a location near the scleral spur. Using the scleral spur as a reference point, the delivery instrument can be advanced further in a generally posterior direction to drive the shunt into eye tissue at a location just inward of the scleral spur toward the iris. The placement and implantation of the shunt can be performed using a gonioscope or other conventional imaging equipment. The delivery instrument preferably is used to force the shunt into a desired position by application of a continual implantation force, by tapping the shunt into place using a distal portion of the delivery instrument, or by a combination of these methods. Once the shunt is in the desired position, it may be further seated by tapping using a distal portion of the delivery instrument.

The delivery instrument can include an open distal end with a lumen extending therethrough. Positioned within the lumen is preferably a pusher tube that is axially movable within the lumen. The pusher tube can be any device suitable for pushing or manipulating the shunt in relation to the delivery instrument, such as, for example, but without limitation a screw, a rod, a stored energy device such as a spring. A wall of the delivery instrument preferably extends beyond pusher tube to accommodate placement within the lumen of a shunt. The shunt can be secured in position. For example, the shunt can be secured by viscoelastic or mechanical interlock with the pusher tube or wall. When the shunt is brought into position adjacent the tissue in the anterior chamber angle, the pusher tube is advanced axially toward the open distal end of the delivery instrument. As the pusher tube is advanced, the shunt is also advanced. When the shunt is advanced through the tissue and such that it is no longer in the lumen of the delivery instrument, the delivery instrument is retracted, leaving the shunt in the eye tissue.

Some embodiments can include a spring-loaded or stored-energy pusher system. The spring-loaded pusher preferably includes a button operably connected to a hinged rod device. The rod of the hinged rod device engages a depression in the surface of the pusher, keeping the spring of the pusher in a compressed conformation. When the user pushes the button, the rod is disengaged from the depression, thereby allowing the spring to decompress, thereby advancing the pusher forward.

In some embodiments, an over-the wire system is used to deliver the shunt. The shunt can be delivered over a wire. Preferably, the wire is self-trephinating. The wire can function as a trocar. The wire can be superelastic, flexible, or relatively inflexible with respect to the shunt. The wire can be pre-formed to have a certain shape. The wire can be curved. The wire can have shape memory, or be elastic. In some embodiments, the wire is a pull wire. The wire can be a steerable catheter.

In some embodiments, the wire is positioned within a lumen in the shunt. The wire can be axially movable within the lumen. The lumen may or may not include valves or other flow regulatory devices.

In some embodiments, the delivery instrument comprises is a trocar. The trocar may be angled or curved. The trocar can be rigid, semi-rigid or flexible. In embodiments where the trocar is stiff, the shunt can be, but need not be relatively flexible. The diameter of the trocar can be about 0.001 inches to about 0.01 inches. In some embodiments, the diameter of the trocar is 0.001, 0.002, 0.004, 0.005, 0.006, 0.007, 0.008, 0.009, or 0.01 inches.

In some embodiments, delivery of the shunt is achieved by applying a driving force at or near the distal end of the shunt. The driving force can be a pulling or a pushing applied generally to the end of the shunt.

The instrument can include a seal to prevent aqueous humor from passing through the delivery instrument and/or between the members of the instrument when the instrument is in the eye. The seal can also aid in preventing backflow of aqueous humor through the instrument and out the eye. Suitable seals for inhibiting leakage include, for example, an o-ring, a coating, a hydrophilic agent, a hydrophobic agent, and combinations thereof. The coating can be, for example, a silicone coat such as MDX™ silicone fluid. In some embodiments, the instrument is coated with the coating and a hydrophilic or hydrophobic agent. In some embodiments, one region of the instrument is coated with the coating plus the hydrophilic agent, and another region of the instrument is coated with the coating plus the hydrophobic agent. The delivery instrument can additionally comprise a seal between various members comprising the instrument. The seal can comprise a hydrophobic or hydrophilic coating between slip-fit surfaces of the members of the instrument. The seal can be disposed proximate of the drainage shunt when carried by the delivery instrument. Preferably, the seal is present on at least a section of each of two devices that are machined to fit closely with one another.

In some embodiments, the delivery instrument can include a distal end having a beveled shape. The delivery instrument can include a distal end having a spatula shape. The beveled or spatula shape can have a sharpened edge. The beveled or spatula shape can include a recess to contain the shunt. The recess can include a pusher or other suitable means to push out or eject the shunt.

The delivery instrument further can be configured to deliver multiple shunts. In some embodiments, when multiple shunts are delivered, the shunts can be arranged in tandem, as described in greater detail below.

Procedures

For delivery of some embodiments of the ocular shunt, the implantation occurs in a closed chamber with or without viscoelastic.

The shunts may be placed using an applicator, such as a pusher, or they may be placed using a delivery instrument having energy stored in the instrument, such as disclosed in U.S. Patent Publication 2004/0050392, filed Aug. 28, 2002, the entirety of which is incorporated herein by reference and made a part of this specification and disclosure. In some embodiments, fluid may be infused through the delivery instrument or another instrument used in the procedure to create an elevated fluid pressure at the distal end of the shunt to ease implantation.

In some embodiments, the shunt is implanted through the fibrous attachment of the ciliary muscle to the sclera. This fibrous attachment zone extends about 0.5 mm posteriorly from the scleral spur, as shown between the two arrows (1020) in FIG. 17.

In some embodiments it is desirable to deliver the shunt ab interno across the eye, through a small incision at or near the limbus (FIG. 1). The overall geometry of the system makes it advantageous that the delivery instrument incorporates a distal curvature, or a distal angle. In the former case, the shunt can be flexible to facilitate delivery along the curvature or can be more loosely held to move easily along an accurate path. In the latter case, the shunt can be relatively rigid. The delivery instrument can incorporate a shunt advancement element (e.g. pusher) that is flexible enough to pass through the distal angle.

In some embodiments, during clinical use, the shunt and delivery instrument can be advanced together through the anterior chamber 32 from an incision at or near the limbus, across the iris, and through the ciliary muscle attachment until the shunt outlet portion is located in the uveoscleral outflow pathway (e.g. exposed to the suprachoroidal space 34 defined between the sclera 38 and the choroid 40). FIG. 2 illustrates a transocular implantation approach with the delivery instrument inserted well above the limbus. The incision, however, can be more posterior and closer to the limbus. In other embodiments, the operator can then simultaneously push on a pusher device while pulling back on the delivery instrument, such that the shunt outlet portion maintains its location in the uveoscleral outflow pathway. The shunt is released from the delivery instrument, and the delivery instrument is retracted proximally, as illustrated in FIG. 3. The delivery instrument then can be withdrawn from the anterior chamber through the incision.

In some embodiments, a viscoelastic can be injected into the suprachoroidal space to create a chamber or pocket between the choroid and sclera which can be accessed by a shunt. Such a pocket could expose more of the choroidal and scleral tissue area, and increase uveoscleral outflow, causing a lower TOP. In some embodiments, the viscoelastic material can be injected with a 25 or 27 G cannula, for example, through an incision in the ciliary muscle attachment or through the sclera (e.g. from outside the eye). The viscoelastic material can also be injected through the shunt itself either before, during or after implantation is completed.

In some embodiments, a hyperosmotic agent can be injected into the suprachoroidal space. Such an injection can delay TOP reduction. Thus, hypotony can be avoided in the acute postoperative period by temporarily reducing choroidal absorption. The hyperosmotic agent can be, for example glucose, albumin, HYPAQUE™ medium, glycerol, or poly (ethylene glycol). The hyperosmotic agent can breakdown or wash out as the patient heals, resulting in a stable, acceptably low TOP, and avoiding transient hypotony.

Therapeutic Agents

The therapeutic agents that may be utilized with the ophthalmic implant system may include one or more agents provided below. The therapeutic agents include but are not limited to pharmaceutical agents, biological agents including hormones, enzyme or antibody-related components, oligonucleotides, DNA/RNA vectors and live cells configured to produce one or more biological components. The use of any particular therapeutic agent is not limited to their primary effect or regulatory body-approved treatment indication or manner of use. The listing of any particular agent within any one therapeutic class below is only representative of one possible use of the agent and is not intended to limit the scope of its use with the ophthalmic implant system. Exemplary therapeutic agents may include: anti-angiogenesis agents, including VEGF receptor tyrosine kinase inhibitors and anti-vascular endothelial growth factor (anti-VEGF) agents such as ranibizumab (LUCENTIS®) and bevacizumab (AVASTIN®), pegaptanib (MACUGEN®), sunitinib and sorafenib and any of a variety of known small-molecule and transcription inhibitors having anti-angiogenesis effect; classes of known ophthalmic agents, including: glaucoma agents, such as beta-blocker agents such as betaxolol, carteolol, levobetaxolol, levobunolol and timolol; carbonic anhydrase inhibitor agents such as acetozolamide, brinzolamide, dorzolamide and methazolamide; mydriatic-cycloplegic agents such as atropine, cyclopentolate, succinylcholine, homatropine, phenylephrine scopolamine and tropicamide; prostaglandin analog agents such as bimatoprost, latanoprost, travoprost and unopro stone; sympathomimetic agents such as apraclonidine, brimonidine and dipivefrin; corticosteroidal and non-steroidal anti-inflammatory agents such as beclomethasone, budesonide, dexamethasone, diclofenac, flunisolide, fluorometholone, fluticasone, ketorolac, hydrocortisone, loteprednol, prednisolone, rimexolone and triamcinolone; anti-infective agents such as aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; anti-histamine agents such as azelastine, emedastine and levocabastine; MAST cells stabilizer agents such as cromolyn sodium, ketotifen, lodoxamide, nedocrimil, olopatadine and pemirolastciliary body ablative agents, such as the aformentioned gentimicin and cidofovir; and other ophthalmic agents such as verteporfin, proparacaine, tetracaine, cyclosporine and pilocarpine.

Other therapeutic agents of the same class as the ophthalmic agents listed above that may be used include: other beta-blocker agents such as acebutolol, atenolol, bisoprolol, carvedilol, asmolol, labetalol, nadolol, penbutolol, pindolol and propranolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and. Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; anti-fungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; anti-parasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other anti-bacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprus side, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as lomustine, melphalan and procarbazine antibiotic-like agents such as bleomycin, daunorubicin, doxorubicin, idarubicin, mitomycin and plicamycin; antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

The therapeutic agents may be released or eluted from the ophthalmic implant system, bound to a surface of the ophthalmic implant, and/or used in conjunction with the ophthalmic implant through injection, oral or eye drop delivery routes. The therapeutic agents may also be released from a separate drug eluting device that is implantable in the same or a different location in the eye or orbital cavity. The separate drug eluting device may be located in a physiologic outflow pathway or physiologic cavity of the eye or body, or may be implanted into an artificially formed site of the eye or body. A variety of controlled-release technologies that are known in the art may be used with the ophthalmic implant system, including non-degradable and biodegradable polymeric and non-polymeric release platforms.

Injection/infusion/implantation routes or sites include intravenous and intravitreal routes, choroidal, scleral, conjunctival, retinal, ciliary body, posterior chamber, anterior chamber (including the angle), trabecular meshwork, Schlemm's canal, suprachoroidal, and other sites along the uveoscleral pathway. The vascular routes or sites include but are not limited to the ophthalmic artery, the lacrimal artery, the short posterior ciliary arteries, the long posterior ciliary arteries, the anterior ciliary arteries, the central retinal arteries, the central retinal veins, and episcleral arteries and veins.

In some embodiments, combinations of agents having synergistic and/or complementary effects for a particular disease or set of related conditions or symptoms may be used. In one example, a disease-treating agent may be used in combination with a metabolism-altering agent affecting the cytochrome P450 system to affect the pharmacokinetics of the disease-treating agent. In another example, an anti-infective agent may be combined with an anti-inflammatory agent to treat inflammation resulting from the infection.

Embodiments Illustrated in FIG. 4

FIG. 4 illustrates one embodiment of a shunt 130 that is operable to drain fluid from the anterior chamber to the uveoscleral outflow pathway (e.g., the suprachoroidal space). The shunt 130 has an inflow portion 132 and an outflow portion 134. When the shunt is implanted, the inflow portion 132 is sized and configured to reside in the anterior chamber of the eye and the outflow portion 134 is sized and configured to reside in the uveoscleral outflow pathway. Extending through the shunt 130 is preferably at least one lumen 136 that operates to conduct the fluid through the shunt 130. Each lumen 136 preferably extends from an inflow end 138 to an outflow end 140 along a lumen axis 142.

The shunt 130 preferably has an outer diameter that will permit the shunt 130 to fit within a 21-gauge or 23-gauge needle or hollow instrument during implantation; however, larger or smaller gauge instruments may also be used. The shunt 130 can also have a diameter that is designed to be delivered with larger needles. For example, the shunt 130 can also be delivered with 18-, 19- or 20-gauge needles. The shunt 130 can have a constant diameter through most of the length of the shunt 130, or the shunt 130 can have portions of reduced diameter, e.g., annular grooves 146, between the proximal end 138 and the distal end 140. The annular grooves 146 produce an irregular outer surface that can operate to mechanically lock or anchor the shunt 130 in place when implanted. Of course, such surface discontinuities or irregularities can also be formed by barbs or other projections, which extend from the outer surface of the shunt, to inhibit migration of the shunt 130 from its implanted position, as described above.

The outflow portion 134 of the shunt 130 preferably is disposed at or near the distal end 140 of the shunt 130. In the illustrated embodiment, the outflow portion 134 has a tapered portion 144; however, it may also have other shapes (e.g. semi-sphere, a paraboloid, a hyperboloid) with a continually decreasing radial dimension with respect to the lumen axis 142 along the length of the axis 142. The tapered portion 144 preferably terminates with a smaller radial dimension at the outflow end 140. During implantation, the tapered portion 144 can operate to form, dilate, and/or increase the size of, an incision or puncture created in the tissue. For example, the distal end 140 can operate as a trocar to puncture or create an incision in the tissue. Following advancement of the distal end 140 of the shunt 130, the tapered portion 144 can be advanced through the puncture or incision. The tapered portion 144 will operate to stretch or expand the tissue around the puncture or incision to accommodate the increasing size of the tapered portion 144 as it is advanced through the tissue. When the stretched tissue passes over the cylindrical channels 146 having a reduced diameter, the stretched tissue will retract generally to fill the cylindrical channels 146 and will abut the edges of the shunt 130 having a greater diameter. The interaction of the tissue and the edges of the shunt 130 will provide an anchor for the shunt 130 following implantation to inhibit shunt migration.

The tapered portion 144 can also facilitate proper location of the shunt 130 into the supraciliary or suprachoroidal spaces. For example, the shunt 130 is preferably advanced through the tissue within the anterior chamber angle during implantation. This tissue typically is fibrous or porous, which is relatively easy to pierce or cut with a surgical device, such as the tip of the shunt 130. The shunt 130 can be advanced through this tissue and abut against the sclera once the shunt extends into the uveoscleral outflow pathway. As the shunt 130 abuts against the sclera, the tapered portion 144 preferably provides a generally rounded edge or surface that facilitates sliding of the shunt 130 within the suprachoroidal space along the interior wall of the sclera. For example, as the shunt 130 is advanced into the uveoscleral outflow pathway and against the sclera, the shunt 130 will likely be oriented at an angle with respect to the interior wall of the sclera. As the tip of the shunt 130 engages the sclera, the tip preferably has a radius that will permit the shunt 130 to slide along the sclera instead of piercing or substantially penetrating the sclera. As the shunt 130 slides along the sclera, the tapered portion 144 will provide an edge against which the shunt 130 can abut against the sclera and reduce the likelihood that the shunt will pierce the sclera.

Once the shunt 130 is implanted in position with the inflow portion 132 residing in the anterior chamber and the outflow portion 134 residing in the uveoscleral outflow pathway, aqueous humor flows from the anterior chamber to the uveoscleral outflow pathway through the lumen 136 of the shunt. The flow of fluid is preferably restricted by the size of the lumen 136, which produces a capillary effect that limits the fluid flow for given pressures. The capillary effect of the lumen allows the shunt to restrict flow and provides a valveless regulation of fluid flow. The flow of fluid through the shunt 130 is preferably configured to be restricted to flow rated that will reduce the likelihood of hypotony in the eye. For example, in some embodiments, the flow rate can be limited to about 2.5 µL/min or less. In some embodiments the flow rate can be limited to between about 1.9 µL/min and about 3.1 µL/min. In other applications, a plurality of shunts 130 can be used in a single eye to conduct fluid from the anterior chamber to the uveoscleral outflow pathway. In such applications, the cumulative flow rate through the shunts preferably is within the range of about 1.9 µL/min to about 3.1 µL/min, although the flow rate for each of the shunts can be significantly less than about 2.5 µL/min. For example, if an application called for implantation of five shunts, then each shunt 130 can be configured to have a flow rate of about 0.5 µL/min.

While the lumen is depicted in FIG. 4 as extending substantially through the longitudinal center of the shunt 130, in some embodiments, the lumen can be offset from the longitudinal center of the shunt. For example, while FIG. 4 depicts the shunt as having a tapered portion 144 that terminates substantially where the tapered portion 144 meets the lumen 136, the lumen 136 can be offset from the center of the shunt 130 such that lumen 136 opens along one of the sides of the tapered portion 144. Accordingly, the tapered portion 144 can terminate at a location offset from the lumen axis 142 and can extend beyond the point at which the interior lumen 136 and the exterior tapered portion 144 meet. Additionally, the lumen can vary in direction along its length.

The shunt 130 preferably comprises any of the materials previously described above. The shunt 130 can be fabricated through conventional micro machining techniques or through procedures commonly used for fabricating optical fibers. For example, in some embodiments, the shunts 130 are drawn with a bore, or lumen, extending therethrough. In some embodiments, the tapered portion 144 at the outflow portion 134 can be constructed by shearing off an end tubular body. This can create a tapered portion 144 that can be used to puncture or incise the tissue during implantation and dilate the puncture or incision during advancement of the shunt 130. Other materials can be used for the shunt of FIG. 4, and other methods of manufacturing the shunt 130 can also be used. For example, the shunt 130 can be constructed of metals or plastics, and the shunts can be machined with a bore that is drilled as described above.

The shunt 130 of FIG. 4 represents a shunt having a construction that provides for the opportunity to vary the size of the shunt 130 or the lumen 136. Additionally, the shunt 130 is able to be delivered in small needles. For example, the shunt 130 can fit within a needle for the implantation procedure. The needle preferably has a size of about 18 gauge to about 23 gauge, and most preferably about 23 gauge. The shunt also need not have a unitary configuration; that is, be formed of the same piece of material. For example, a proximal portion of the shunt can be formed of glass drawn to have at least one small diameter lumen. A distal portion of the shunt can be a cap formed of a different material. The cap includes a tissue-piercing end and one or more outlet openings. Each of the one or more outlet openings communicates with at least one of the one or more lumens in the proximal portion. In one preferred mode, the cap has a conically shaped tip with a plurality of outlet openings disposed proximal of the tip's distal end.

Embodiments Illustrated in FIGS. 5 and 6

Additional embodiments of shunts are depicted in FIG. 5. FIG. 5 illustrates a shunt 230 having a relatively similar construction as that of FIG. 4. FIG. 5 illustrates an embodiment of a shunt 230 having an elongate body with an inflow portion 232 and an outflow portion 234. A lumen(s) 236 preferably extends between an inflow end 238 and an outflow end 240. Proximate the outflow end 240 is preferably a tapered portion 244 having a construction similar to the embodiments described above with respect to FIG. 4. Alternatively, the bodies of the shunts can be formed of a porous material which has one or more flow paths from the inflow portion 232 to the outflow portion 240.

FIG. 5 depicts a plurality of apertures 246 extending through the wall of the shunt 230. While the apertures 246 are depicted as extending through a middle portion of the shunt 230, the apertures can extend through other portions of the shunt 230. For example, the apertures 246 can also extend through the outflow portion 234, or more particularly, through the tapered portion 244. The plurality of apertures 246 can provide several functions. One such function is that when the shunt 230 is inserted into the uveoscleral outflow pathway, the apertures 246 provide a plurality of routes through which the aqueous humor can drain. For example, once the shunt 230 is inserted into the eye, if the shunt 230 only has one outflow channel (e.g., one end of a lumen), that outflow channel can be plugged, for example, by the shunt's abutment against the interior wall of the sclera or the outer wall of the choroid. Additionally, the outflow channel can be clogged with tissue that is accumulated during the advancement of the shunt 230 through the fibrous or porous tissue. The plurality of apertures 246 provides a plurality of routes through which the fluid may flow to maintain patency and operability of the drainage shunt 230. In embodiments where the shunt has a porous body, the apertures 246 can define surface discontinuities to assist in anchoring the shunt once implanted.

FIG. 6 depicts embodiments of a shunt 330 having an elongate body with an inflow portion 332 and an outflow portion 334. The body of the shunt 330 is formed of a porous material. Proximate the outflow end 340 is preferably a tapered portion 344 having a construction similar to the embodiments described above with respect to FIG. 4. In some embodiments, the shunt 330 includes cylindrical recessed portions along the elongate body to provide enhanced gripping features during implantation and anchoring following implantation within the eye tissue.

The shunts depicted in FIGS. 5 and 6 are preferably constructed of metals, ceramics, or plastics; although several of the other materials noted herein can also be used. For example, the shunts 230, 330 can be constructed of titanium and manufactured by conventional sintering, micro machining, laser machining, and/or electrical discharge machining. The shunt 230 of FIG. 5 preferably restricts fluid flow in similar manners described above with respect to the embodiments of FIG. 4. Alternatively, where the shunts 230, 330 include a porous body the cross-section and porosity can be calibrated (done to 0.5 micrometers) to control the flow rates of aqueous humor through the shunt. The flow rates through the shunts illustrated in FIGS. 5 and 6 preferably are similar to the rates specified above.

Embodiments Illustrated in FIGS. 7 and 8

FIGS. 7-8 depict embodiments of another shunt 430 having an elongate body with an inflow portion 432 and an outflow portion 434. A lumen 436 preferably extends between an inflow end 438 and an outflow end 440. Although the illustrated embodiment includes just one lumen, other embodiments can include multiple lumens, each including the flow restriction described below.

Proximate the outflow end 440 is preferably a tapered portion 444 that decreases in a radial dimension along a lumen axis 442. In some embodiments, the shunt 430 includes cylindrical recessed portions 446 along the elongate body to provide enhanced gripping features during implantation and anchoring following implantation within the eye tissue. The lumen 436 is preferably configured to accommodate placement therein of a spiral flow channel core 448 that is configured to provide preferred flow restriction.

The core 448 is preferably configured to extend through the lumen 436 between the inflow end 438 and the outflow end 440 and includes a tortuous or spiral flow channel 450 extending generally along the exterior of the core 448. In effect, the spiral flow channel 450 provides an extended path for the flow of fluid between the two ends of the shunt 430 that is greater than a straight lumen extending between the ends of the shunt 430. The extended path provides a greater potential resistance of fluid flow through the shunt without increasing the length of the shunt.

While the core 448 is depicted in FIGS. 7 and 8 as having only a single spiral flow channel 450, the core 448 could have a plurality of spiral flow channels 450 for providing a plurality of flow paths through which fluid may flow through the shunt 430. For example, the core 448 can have two or more spiral flow channels 450. Additionally, the core 448 can also have one or more straight lumens extending through the core 448.

The shunt 430 is preferably manufactured of metals, ceramics, or plastics through conventional micro machining, laser machining, or electrical discharge machining. For example, the shunt 430 can be constructed of titanium, glass, or noble metals. In some embodiments, the core 448 is made of the same material as the body of the shunt 430 while in yet further embodiments, the core 448 includes a material that is different than the body of the shunt 430.

Embodiments Illustrated in FIGS. 9 and 10

FIGS. 9-10 depicts embodiment of another shunt 530 having an elongate body with an inflow portion 532 and an outflow portion 534. The shunt 530 preferably includes a lumen 536 that extends between an inflow end 538 and an outflow end 540. The shunt 530 preferably includes a tapered portion 544 at the outflow end 540 that decreases in a radial dimension along a lumen axis 542. In some embodiments, the shunt 530 includes cylindrical recessed portions 546 along the elongate body to provide enhanced gripping features during implantation and anchoring following implantation within the eye tissue.

The shunt 530 is preferably configured to conduct fluid between the anterior chamber and the uveoscleral outflow pathway with the inflow end 538 exposed to the anterior chamber and the outflow end 540 exposed to the suprachoroidal space. The shunt 530 preferably reduces the likelihood of hypotony of the eye by providing a ball-check pressure regulator. For example, when the intraocular pressure exceeds a particular pressure, the ball-check pressure regulator will open and permit fluid to flow between the anterior chamber and the uveoscleral outflow pathway. When the intraocular pressure reaches a second, lower pressure, the ball-check pressure regulator will close and limit or inhibit fluid from being conducted to the uveoscleral outflow pathway. The ball-check pressure regulator will remain closed until the intraocular pressure again reaches the particular pressure, and at which time the ball-check valve will reopen to permit or enhance drainage of fluid to the uveoscleral outflow pathway. Accordingly, the shunt 530 provides drainage of the anterior chamber through the shunt 530 based on the intraocular pressure levels and reduces the likelihood for over-draining the anterior chamber and causing hypotony.

The ball-check regulator is preferably configured to be positioned within the lumen 536 of the shunt 530 and includes a luminal spring 552 that is configured to reside within the lumen. The luminal spring 552 is depicted as a coil spring, but the luminal spring 552 can be any type of spring or biasing member that is resilient or reversibly compressible. For example, the spring 552 can comprise Nitinol or other flexible or resilient materials. The ball-check regulator also preferably includes a ball 554 that preferably has a diameter less than the diameter of the lumen 536 of the shunt 530 so as to permit movement of the ball 554 within the lumen 536 and to permit the flow of fluid between the ball 554 and the inner wall of the lumen 536 when the ball 554 resides within the lumen 536. The luminal spring 552 is preferably configured to engage a ball 554 at one end of the luminal spring 552 and to permit the ball 554 to move between different positions within the lumen 536.

A ball sleeve 556 is preferably provided within at least a portion of the lumen 536 and is positioned adjacent to the ball 554 opposite the luminal spring 552. For example, FIGS. 9 and 10 depict the ball sleeve 556 positioned adjacent the inflow end 538. The luminal spring 552 is depicted as extending from the outflow portion 534 toward the inflow portion 532 with the ball 554 interposed between one end of the luminal spring 552 and the ball sleeve 556. The portion of the ball sleeve 556 that is adjacent the ball 554 preferably has a lumen that has a diameter less than that of the ball 554 and limits movement of the ball 554 so the ball is unable to pass through the ball sleeve lumen. This end of the ball sleeve 556 preferably provides a ball seat 558 against which the ball 554 can rest when urged against the ball sleeve 556 by the luminal spring 552. In some embodiments, the ball 554 prevents flow when contacting seat of the ball sleeve 556; however, in other embodiments, some restricted flow can occur through the shunt even when the ball 554 rests against the seat. Such flow can occur through one or more parallel flow paths or through one or more relatively small flow paths that extend around the ball 554 and remain open when the ball 554 contacts the seat of the ball sleeve 556.

The shunt 530 also preferably includes a distal taper or cone 560 that is configured to reside at least partially within the lumen 536. The distal cone 560 preferably includes radial flanges 562 that provide a means for securing the cone 560 in place by engaging the inner wall of the lumen 536 while providing a space between the distal cone 560 and the inner wall of the lumen 536. In some embodiments, the distal cone 560 provides radial channels 562 instead of flanges through which the fluid can be conducted. The space between the inner wall of the lumen 536 and the cone 560 or the channels 562 permits fluid conducted through the lumen 536 to exit the shunt by flowing around the distal cone 560.

When the ball-check pressure regulator is assembled, the luminal spring 552 is preferably seated against the distal cone 560 on one end and presses against the ball 554 on the other end with a determined force. The ball 554 is moved against the ball seat 558 of the ball sleeve 556 as a reaction to the force of the luminal spring 552. When the shunt 530 is inserted within the eye with the inflow end 538 exposed to the anterior chamber and the outflow end 540 exposed to the suprachoroidal space, the ball 554 will be exposed to the intraocular pressure of the anterior chamber. The ball 554 will be pressed against the ball seat 558 and limit or inhibit flow of fluid past the ball 554 until the intraocular pressure exerts a force upon the ball 554 that is greater than the force applied by the luminal spring 552. When the luminal spring 552 force is overpowered by the intraocular pressure, the ball 554 will be moved down the lumen 536 away from the ball seat 558, thus permitting fluid to pass around the ball 554, through the lumen 536, and out the outflow portion 534 between the radial flanges 562 of the distal cone 560. When the intraocular pressure drops, the force pressing against the ball 554 will be reduced, and when the force applied on the ball 554 by the intraocular pressure is less than the force applied on the ball 554 by the luminal spring 552, the ball 554 will be moved through the lumen 536 until it is pressed against the ball seat 558, thus stopping the flow of fluid through the lumen 536.

Figure 11:
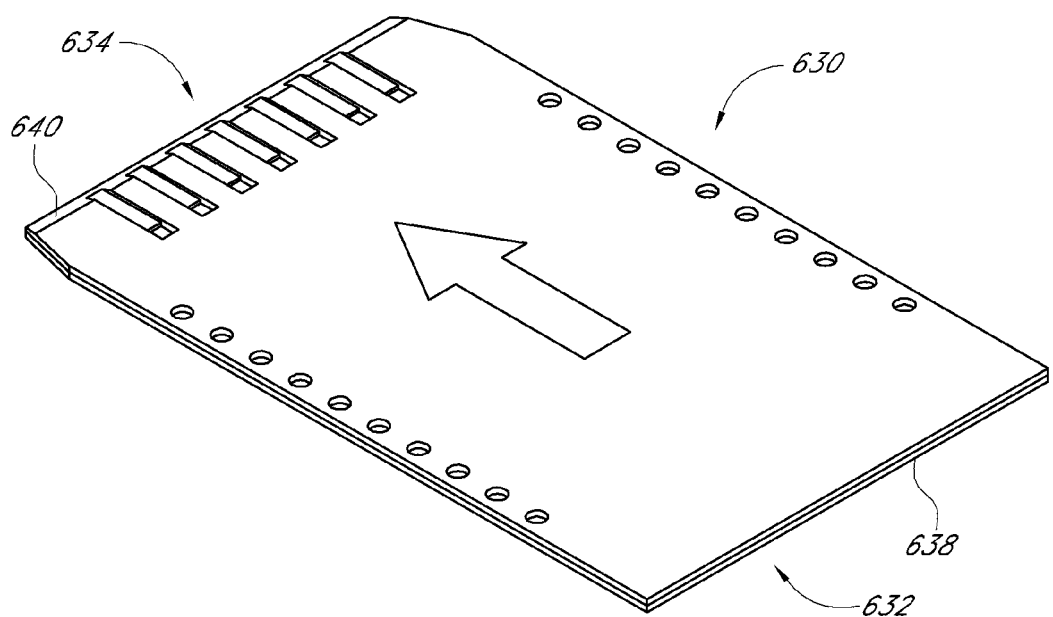
FIG. 11 illustrates another drainage implant in accordance with embodiments disclosed herein.
Figure 12:
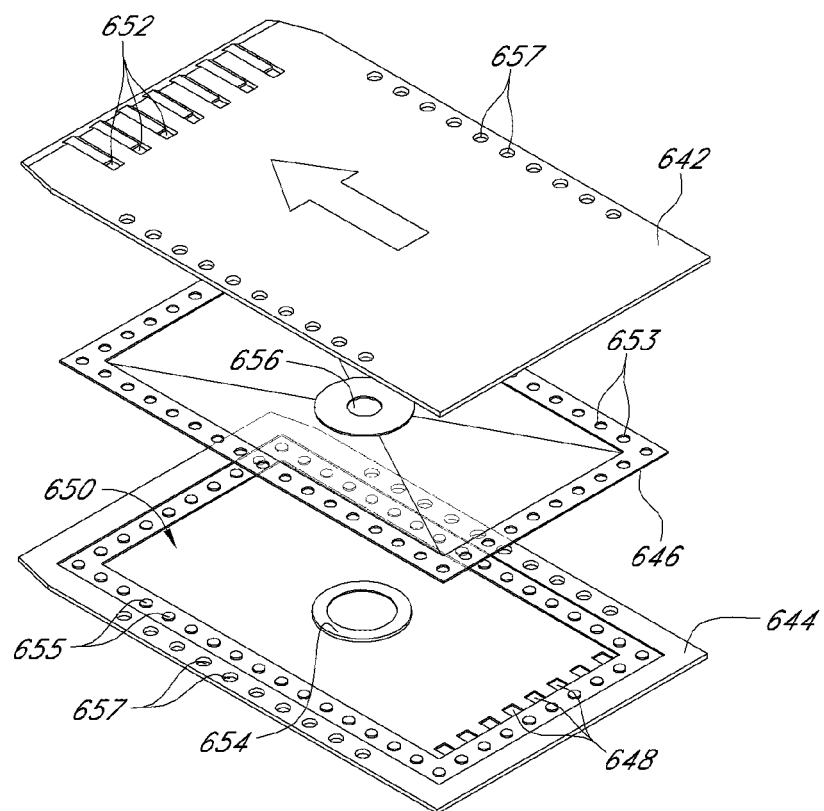
FIG. 12 illustrates an exploded view of the implant of FIG. 11.

Embodiments Illustrated in FIGS. 11 and 12

FIGS. 11 and 12 illustrate embodiments of a generally flat pressure regulator shunt 630. The shunt 630 preferably includes an inflow portion 632 and an outflow portion 634. The inflow portion 632 preferably includes a plurality of inlets along an inflow end 638, and the outflow portion 634 preferably includes a plurality of outlets along an outflow end 640. The shunt 630 is preferably constructed of three portions: a top portion 642, a bottom portion 644, and a middle portion 646. The top portion 642 and the bottom portion 644 are preferably substantially rigid and provide a housing for the shunt 630. The top portion 642 is engageable with the bottom portion 644 by aligning a plurality of apertures 651 extending along the edges of the portions 642, 644. The two portions 642, 644 can be secured together by glue, solder, or other means for connection the portions. The bottom portion 644 preferably includes inflow apertures 648 that are configured to permit fluid to enter into a chamber 650 formed by the edges of the shunt 630. The top portion 642 preferably includes a plurality of outflow apertures 652 through which fluid can exit the chamber 650 and be discharged from the shunt 630.

A flexible or resilient middle portion 646 is preferably positioned between the two portions 642, 644. The middle portion 646 is preferably a biased membrane that is biased toward the bottom portion 644 when the shunt 630 is assembled and rests on a membrane seat 654. A plurality of apertures 653 along the edges of the membrane preferably coincides with a plurality of protrusions 655 on the top and bottom portions 642, 644. When the shunt 630 is assembled, the interlocking protrusions 655 and apertures 653 create a seal that reduces the likelihood of fluid from leaking from the chamber 650. The middle portion 646 is preferably constructed of a nitinol sputter deposited silicone membrane. The membrane preferably pressed against the bottom portion 644 and has an aperture 656 extending therethrough. The aperture 656 provides a flow path through which fluid conducted through the shunt 630 can pass when the membrane does not rest on the membrane seat 654.

In operation, the shunt is inserted into the eye with the inflow portion 632 exposed to the anterior chamber and the outflow portion 634 exposed to the uveoscleral outflow pathway. Fluid from the anterior chamber will enter into the inflow apertures 648 and fill the chamber 650 on one side of the membrane of the middle portion 646. Because the middle portion membrane 646 is biased toward the membrane seat 654, the aperture 656 will not permit fluid to flow to the other side of the membrane. When the intraocular pressure reaches an elevated level, the fluid pressure within the chamber 650 will create a force against the membrane 646 and cause the membrane 646 to disengage the membrane seat 654. As the membrane 646 disengages the membrane seat 654, the membrane aperture 656 permits fluid to flow through the membrane 646 into the other side of the chamber 650 and out the outflow apertures 652. The pressure at which the membrane will be deflected from the membrane seat 654 preferably corresponds to acceptable intraocular pressure levels. The large surface area of the membrane 646 will provide for a low tolerance of pressure regulation.

The shunt 630 is preferably implanted following the creation of an incision in the tissue. In some embodiments, the delivery instrument may create the incision for the shunt 630 and insert the shunt 630 into the incision. In yet other embodiments, the shunt 630 can have a sharpened outflow end 640 and create the incision itself as it is advanced through the tissue.

Figure 13:
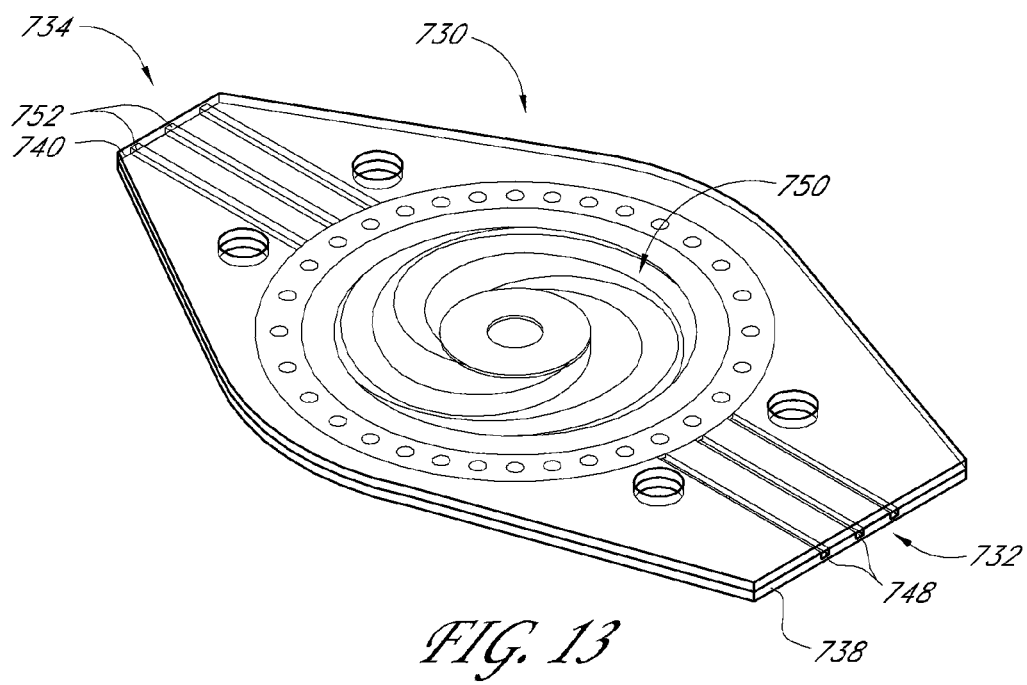
FIG. 13 illustrates another drainage implant in accordance with embodiments disclosed herein.
Figure 14:
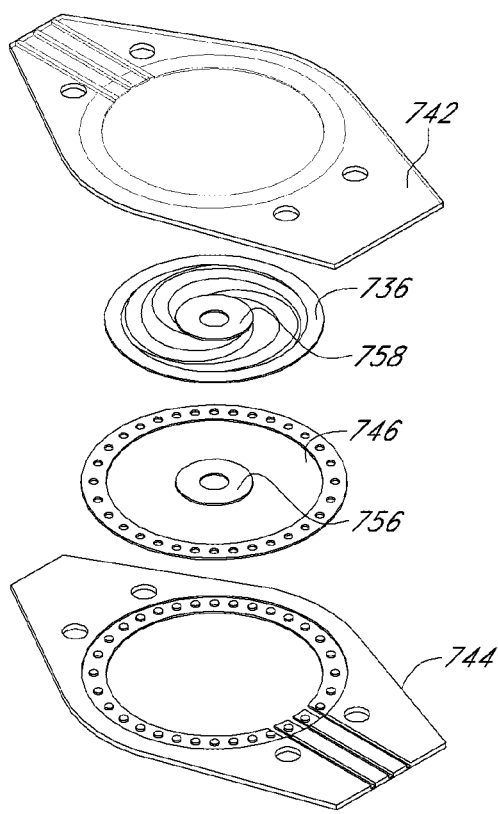
FIG. 14 illustrates an exploded view of the implant of FIG. 13.

Embodiments Illustrated in FIGS. 13 and 14

FIGS. 13 and 14 depict a shunt 730 that operates under similar principles as that of the embodiments depicted in FIGS. 11 and 12. The shunt has an inflow portion 732 and an outflow portion 734. The inflow portion 732 includes an inflow end 738 and inflow apertures 748. The outflow portion 734 includes an outflow end 740 and outflow apertures 752. The inflow apertures 748 and the outflow apertures 752 are in fluid communication with a shunt chamber 750. The shunt 730 preferably includes four portions: a top portion 742, a spring or biasing portion 736, a membrane portion 746, and a bottom portion 744. When the shunt is assembled, the sprint or biasing portion 736 preferably presses the membrane portion 746 against the bottom portion 744, thus restricting the fluid communication through the shunt 730. When the intraocular pressure reaches a certain level, the resultant force exerted against the membrane portion 746 will exceed that of the spring or biasing portion 736 and cause the membrane portion 746 to disengage the bottom portion 744. When the membrane portion 746 is not pressing against the bottom portion 744, an aperture 756 will permit fluid to flow through the membrane 746 and through an aperture 758 in the spring or biasing portion 736. During the period of flowing fluid, the aqueous humor will flow through the chamber 750 and out the shunt 730 through the outflow apertures 752.

In some embodiments of the illustrated shunts in FIGS. 11-14, an intraocular pressure regulator is provided having an inlet portion that provide at least one ingress flow path that include one or more influent openings. The openings preferably have a total cross-sectional flow area and communicate with an interior chamber within the shunt. In some embodiments, the shunts include an outlet portion that provides an egress flow path that has one or more effluent openings. In yet further embodiments, the shunts have a pressure regulation valve that includes a deflectable plate with a surface area exposed to fluid within the interior chamber. The surface area preferably is substantially greater than the total cross-sectional flow area. The valve is preferably located between the interior chamber and one or more effluent openings such that movement of the deflectable plate regulates flow from the interior chamber to the one or more effluent openings. The plate preferably extends in a direction generally parallel to the inlet flow path and to the outlet flow path.

Figure 15:
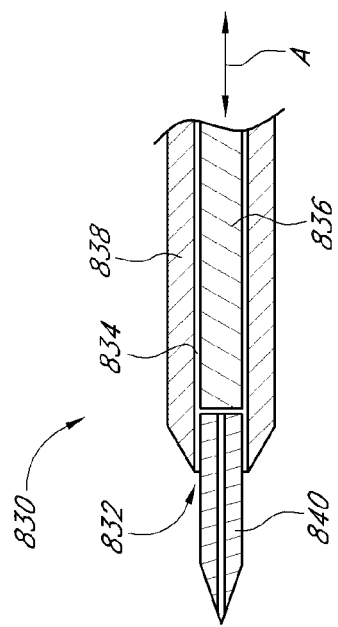
FIG. 15 illustrates a cross-sectional view of one embodiment of a delivery device with an implant extending therefrom.

Embodiments Illustrated in FIG. 15

FIG. 15 illustrates one embodiment of a delivery instrument 830 that can be used with at least several of the shunt embodiments described herein. The delivery instrument 830 preferably includes an open distal end 832 with a lumen 834 extending therethrough. Positioned within the lumen 834 is preferably a pusher tube 836 that is axially movable within the lumen 834, as indicated by the arrows A. A wall 838 of the delivery instrument 830 preferably extends beyond pusher tube 836 to accommodate placement within the lumen 834 of a shunt 840. The shunt 840 can be secured in position. For example, the shunt 840 can be secured by viscoelastic or mechanical interlock with the pusher tube 836 or wall 838. When the shunt is brought into position adjacent the tissue in the anterior chamber angle, the pusher tube 836 is advanced axially toward the open distal end 832 of the delivery instrument 830. As the pusher tube 836 is advanced, the shunt 840 is also advanced. When the shunt 840 is advanced through the tissue and such that it is no longer in the lumen 834 of the delivery instrument 830, the delivery instrument 830 is retracted, leaving the shunt 840 in the eye tissue.

Figure 16:
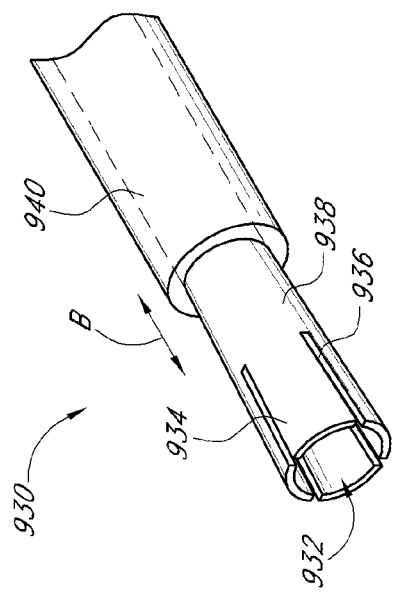
FIG. 16 illustrates a perspective view of another embodiment of a delivery device.

Embodiments Illustrated in FIG. 16

FIG. 16 illustrates another embodiment of a delivery instrument 930 that can be used with embodiments of shunts described herein. The delivery instrument 930 preferably has an open distal end 932 that is configured to receive a shunt (not shown). The delivery instrument 930 preferably has a plurality of prongs 934 that are separated circumferentially by axially-extending slots 936 in an inner cylinder 938 of the delivery instrument. The prongs 934 are preferably slightly biased radially outward and are able to be forced radially inward to grasp a shunt that resides within the open distal end 932. A slider tube 940 is preferably positioned around the inner cylinder 938 and has an inner diameter that is slightly larger than the outer diameter of the inner cylinder 938. The slider tube 940 is preferably axially movable over the inner cylinder 938 in the direction of the arrows B. As the slider tube 940 is advanced over the prongs 934, the prongs 934 are forced radially inward and the gaps created by the slots 936 are reduced. As the prongs 934 are forced radially inward, the inner diameter of the inner cylinder 938 is reduced, and the prongs 934 can firmly grasp a shunt that is positioned therein. When the shunt is properly positioned within the eye tissue, the slider tube 940 is withdrawn to permit the prongs 934 to expand radially outwardly, and the shunt is released from the grip of the prongs 934. The delivery instrument 930 is then removed from the eye. If the shunt needs to be repositioned, the delivery instrument 930 can re-grip the shunt by placing the prongs 934 over the shunt and advancing the slider tuber 940 over the prongs. The shunt can be release following its repositioning or orienting in the same manner as described above. If multiple shunts are required, a new shunt can be inserted into the delivery instrument and deliver in the same manner as described above.

Figure 17:
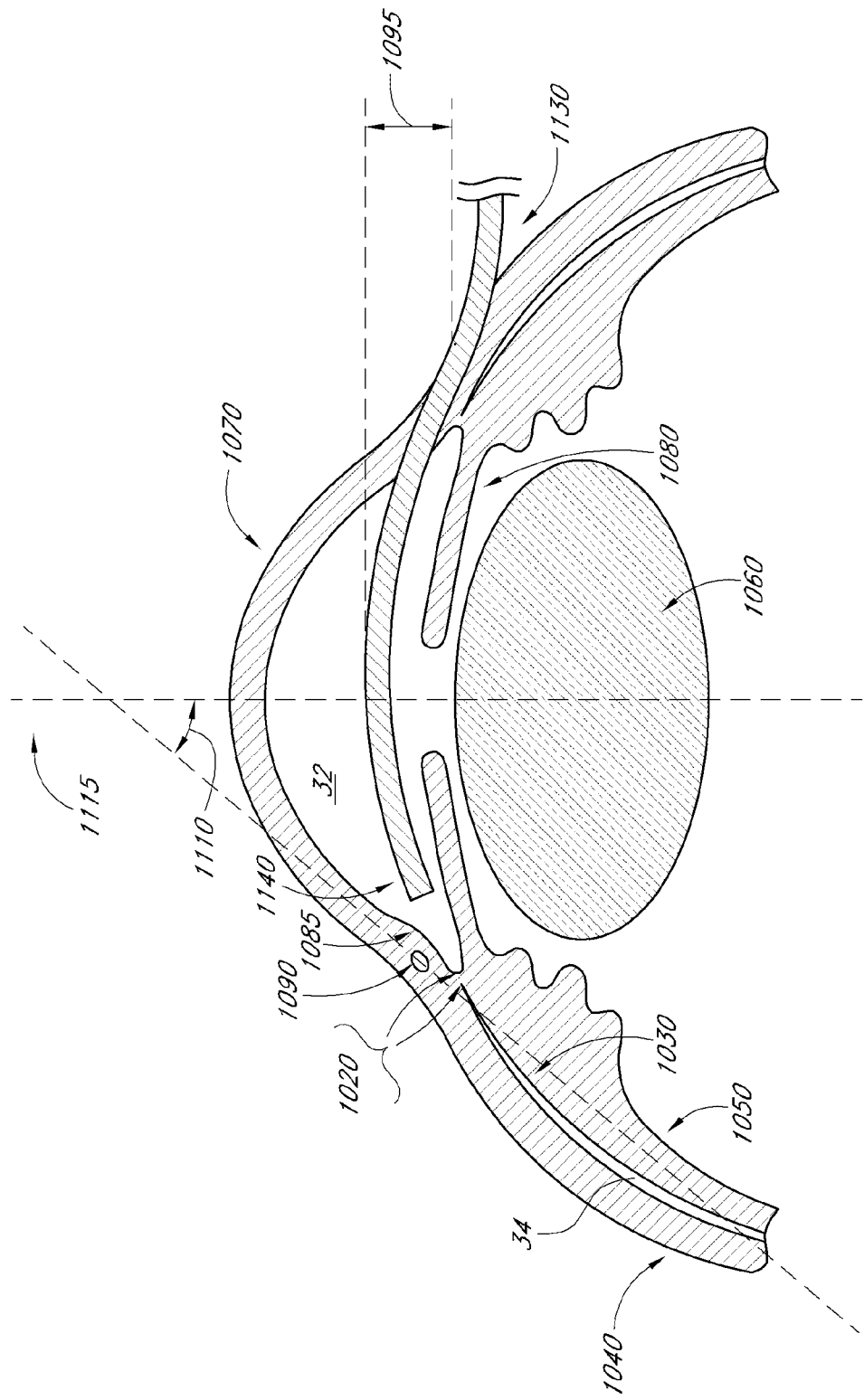
FIG. 17 illustrates a schematic cross-sectional view of an eye with another delivery device being advanced across the anterior chamber.
Figure 18:
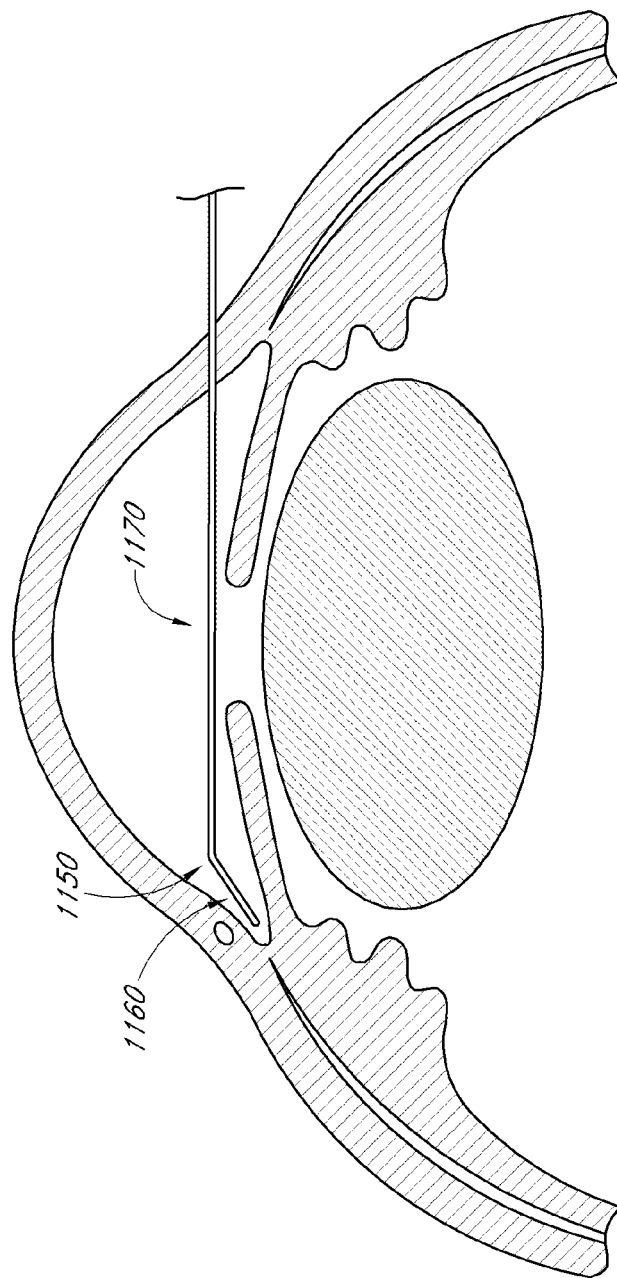
FIG. 18 illustrates a schematic cross-sectional view of an eye with another delivery device being advanced across the anterior chamber.

Embodiments Illustrated in FIGS. 17 and 18

FIG. 17 shows a meridional section of the anterior segment of the human eye and schematically illustrates another embodiment of a delivery instrument 1130 that can be used with embodiments of shunts described herein. In FIG. 17, arrows 1020 show the fibrous attachment zone of the ciliary muscle 1030 to the sclera 1040. The ciliary muscle is part of the choroid 1050. The suprachoroidal space 34 is the interface between the choroid and the sclera. Other structures in the eye include the lens 1060, the cornea 1070, the anterior chamber 32, the iris 1080, and Schlemm's canal 1090.

In some embodiments, it is desirable to implant a shunt through the fibrous attachment zone, thus connecting the anterior chamber to the uveoscleral outflow pathway, in order to reduce the intraocular pressure in glaucomatous patients. In some embodiments, it is desirable to deliver the shunt with a device that traverses the eye internally (ab interno), through a small incision in the limbus.

The delivery instrument/shunt assembly must be passed between the iris and the cornea to reach the iridocorneal angle. Therefore, the height of the delivery instrument/shunt assembly (dimension 1095 in FIG. 17) preferably is less than about 3 mm, and more preferably less than 2 mm.

The suprachoroidal space between the choroid and the sclera generally forms an angle 1110 of about 55 degrees with the optical axis 1115 of the eye. This angle, in addition to the height requirement described in the preceding paragraph, are features to consider in the geometrical design of the delivery instrument/shunt assembly.

The overall geometry of the system makes it advantageous that the delivery instrument 1130 incorporates a distal curvature 1140, as shown in FIG. 17, or a distal angle 1150, as shown in FIG. 18. The distal curvature (FIG. 17) is expected to pass more smoothly through the corneal or scleral incision at the limbus. However, the shunt preferably is curved or flexible in this case. Alternatively, in the design of FIG. 18, the shunt may be mounted on the straight segment of the delivery instrument, distal of the "elbow" or angle 1150. In this case, the shunt may be straight and relatively inflexible, and the delivery instrument can incorporate a delivery mechanism that is flexible enough to advance through the angle. In some embodiments, the shunt is a rigid tube, provided that the shunt is no longer than the length of the distal segment 1160.

The distal curvature 1140 of delivery instrument 1130 may be characterized as a radius of approximately 10 to 30 mm, and preferably about 20 mm. The distal angle of the delivery instrument depicted in FIG. 18 may be characterized as approximately 90 to 170 degrees relative to an axis of the proximal segment 1170 of the delivery instrument, and preferably about 145 degrees. The angle incorporates a small radius of curvature at the "elbow" so as to make a smooth transition from the proximal segment 1170 of the delivery instrument to the distal segment 1160. The length of the distal segment 1160 may be approximately 0.5 to 7 mm, and preferably about 2 to 3 mm.

Figure 19:
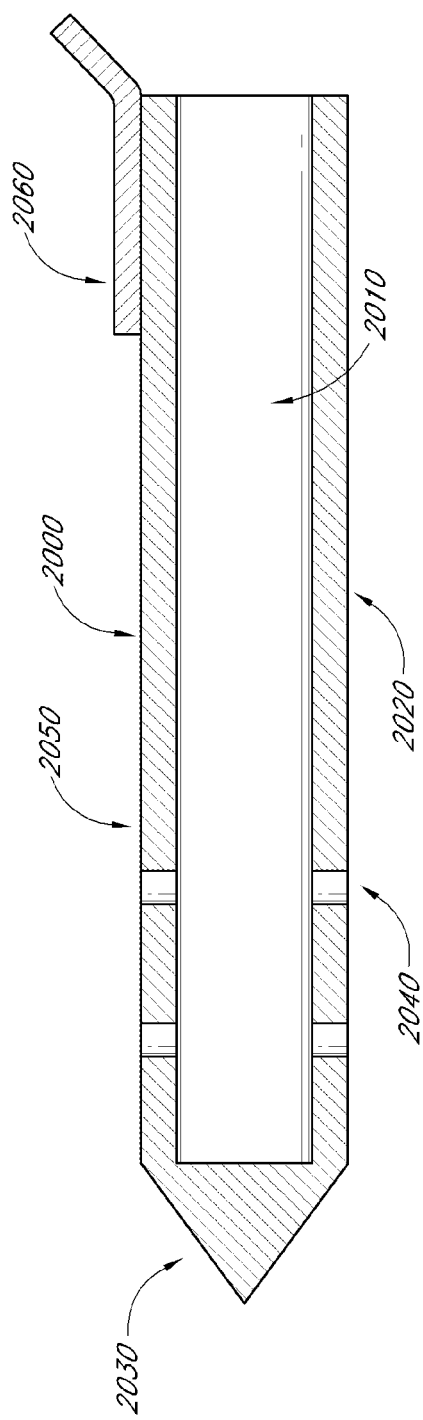
FIG. 19 illustrates a cross-sectional view of another drainage implant in accordance with embodiments disclosed herein.
Figure 20:
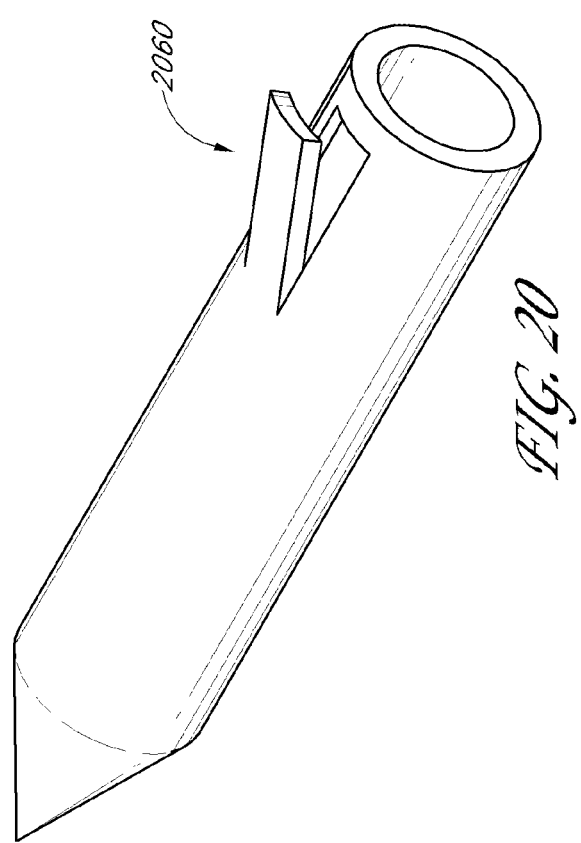
FIG. 20 illustrates a perspective view of another drainage implant in accordance with embodiments disclosed herein.

Embodiments Illustrated in FIGS. 19 and 20

FIG. 19 illustrates in cross-section another embodiment of a shunt 2000 that is operable to drain fluid from the anterior chamber to the suprachoroidal space. The shunt can include one or more lumens 2010, a circumferential wall 2020, and a tip 2030. The tip may be pointed (for pushing through resistant tissue), or rounded (to be incapable of penetrating through tissue such as the sclera). One or more side holes 2040 in the wall permit the egress of aqueous fluid flowing from the anterior chamber through lumen(s) 2010. The tip 2030 may be comprised of, for example, but without limitation, a thermoplastic material such as polyurethane or Pebax or polymethylmethacrylate or polyimide, or elastomeric material such as silicone, or metal material such as titanium, steel, or nitinol. The tip 2030 may be unitary with or be attached to the longitudinal body section 2050 of the shunt by molding, or adhesive bonding, or thermal bonding. The longitudinal body may be comprised of, for example, but without limitation, a thermoplastic material such as polyurethane or Pebax or polymethylmethacrylate or polyimide, or elastomeric material such as silicone, or metal material such as titanium, steel, or nitinol. The body material is preferably flexible, such as polyurethane or Pebax or silicone. However, it may be comprised of rigid material such as polymethylmethacrylate or metal. In this case, the shunt may be made flexible by creating one or more indentations, or by etching or machining or laser processing a relief pattern in the wall of the shunt, such is known in the art of design and fabrication of shunts for the coronary arteries. The shunt does not need to provide a solid tubular conduit between the anterior chamber and the suprachoroidal space, as the shunt will be surrounded by tissue, and the fluid flow will thus be constrained within the tubular envelope created by the shunt.

In some embodiments, the flexible shunt has an outer diameter of approximately 0.1 to 2.0 mm diameter, preferably about 0.4 mm. The length of the shunt is approximately 0.5 to 7 mm, preferably about 2 to 4 mm.

The shunt may also incorporate fixation features 2060, such as flexible radial extensions. The extensions may be separate pieces attached to the shunt, or may be formed by slitting the shunt wall, and thermally forming or mechanically deforming the extensions radially outward, as shown in FIG. 20. If the extensions 2060 are separate pieces, they may be comprised of flexible material such as nitinol or polyimide (and may assume an extended shape once implanted in tissue). The extensions 2060 may be located at the anterior or posterior ends of the shunt, or both, to inhibit extrusion of the shunt from its intended location. The flexibility of the fixation features will facilitate entry through the corneal incision, and also through the ciliary muscle attachment tissue.

Figure 21:
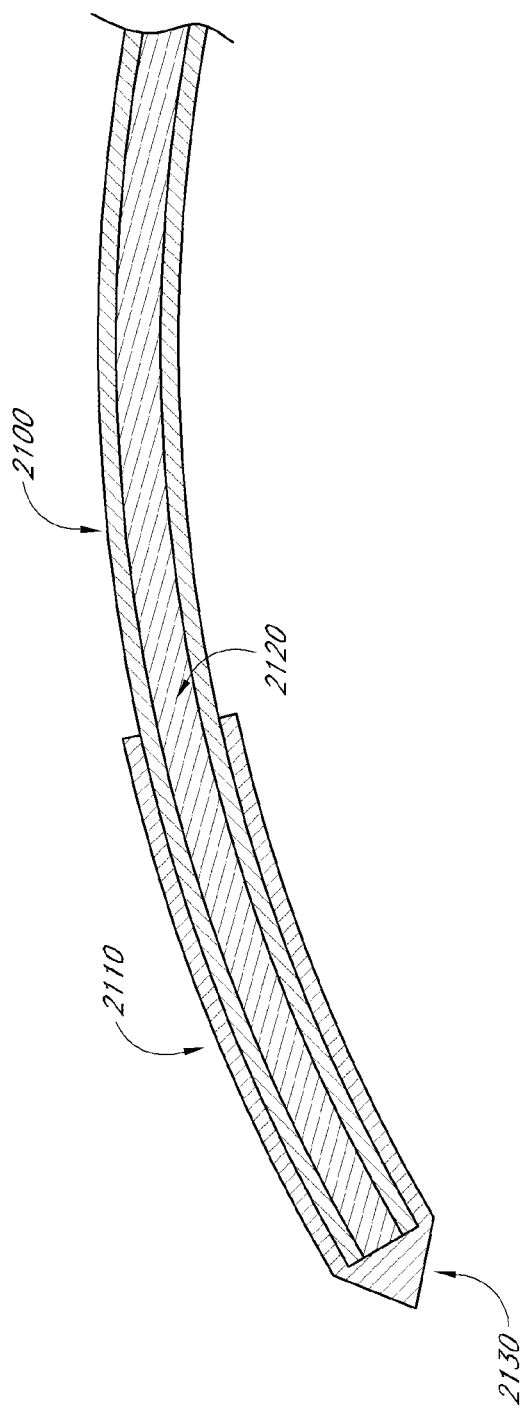
FIG. 21 illustrates a cross-sectional view of another embodiment of a delivery device.

Embodiments Illustrated in FIG. 21

FIG. 21 shows another embodiment of a system that can be used to perform a variety of methods or procedures. The curved shaft of a delivery instrument 2100 can be hollow, and the shunt 2110 can be slidably mounted on the outer diameter of the delivery instrument. The shunt is preferably flexible. A flexible, slidable stylet 2120 can be inserted through the shaft of the delivery instrument, and pushes against the inner wall of shunt tip 2130. The stylet 2120 can be comprised of a flexible material with a high modulus of elasticity, such as stainless steel, and preferably nitinol. The proximal end of the delivery instrument is not shown, but provides for a sliding mechanism to advance and retract the stylet 2120 by the operator. The mechanism may be incorporated into a handle, such as the push-pull controls in the handles of electrophysiology catheters known in the art; or the proximal end of the stylet 2120 may extend outward from the proximal end of the shaft, such that the operator may grasp it directly to push and pull it.

In some embodiments, during clinical use, the shunt and shaft assembly can be advanced together through the limbus, across the iris, and through the ciliary muscle until the shunt tip is located in the suprachoroidal space. The operator then simultaneously pushes on the stylet 2120 while pulling back on the delivery instrument 2100, such that the shunt tip maintains its location in the suprachoroidal space. The shunt 2110 is released distally from the delivery instrument 2100, and the delivery instrument 2100 is retracted proximally. At this point, the shunt 2110 is still riding on the distal end of the stylet 2120. The next step is to withdraw the stylet 2120, leaving the shunt 2110 in place in the tissue. Finally, the delivery instrument 2100 is withdrawn from the anterior chamber through the incision.

A shunt and delivery instrument assembly, including a flexible stylet, similar to that shown in FIG. 21 can also be used in conjunction with the angled delivery instrument of FIG. 18 and a rigid tube shunt. The operation is similar to that described in the preceding paragraph.

Figure 22:
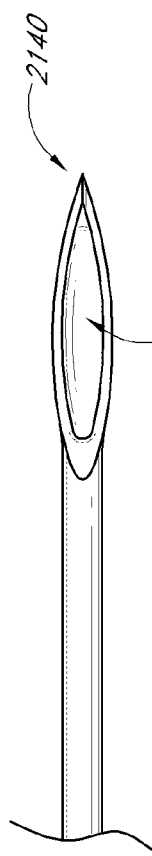
FIG. 22 illustrates another delivery device in accordance with embodiments disclosed herein.

Embodiments Illustrated in FIGS. 22 and 23

Figure 23A:
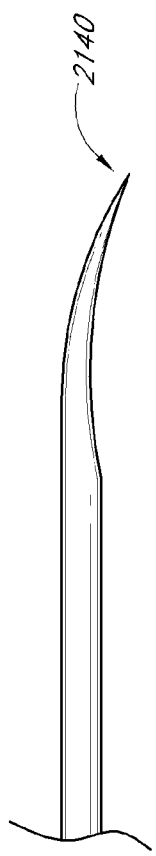
FIGS. 23A-B illustrates side views of the delivery device of FIG. 22.
Figure 23B:
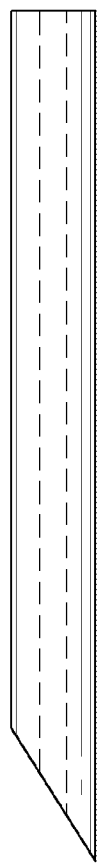

FIGS. 22, 23A and 23B show an example of a delivery instrument for a shunt. In some embodiments, the shunt is delivered through a needle with a cutting tip 2140. The shunt can be loaded inside of the shaft of the needle for delivery through the eye. The needle can be curved on the side of the needle opposite to the beveled opening 2150, as illustrated in FIG. 23(*a*). This allows the curved part of the needle to take a "downward" direction without appreciably affecting the effective height of the device. This geometry can be advantageous for passage through the anterior chamber between the iris and the cornea. At the same time, the curve permits the sharp tip of the needle to follow the angle of the ciliary muscle/sclera interface (angle 1110 shown in FIG. 17). Further, the design of the curved tip as shown in FIG. 23A can limit the depth of the dissection of the ciliary muscle from the sclera to the minimum depth necessary to cut through the fibrous attachment tissue. This depth is estimated to be less than about 0.5 mm. In addition, the curvature of the tip act as a baffle to redirect the shunt as it is pushed distally outward through the needle. In other embodiments, the needle cutting tip is straight, as illustrated in FIG. 23B.

Figure 24:
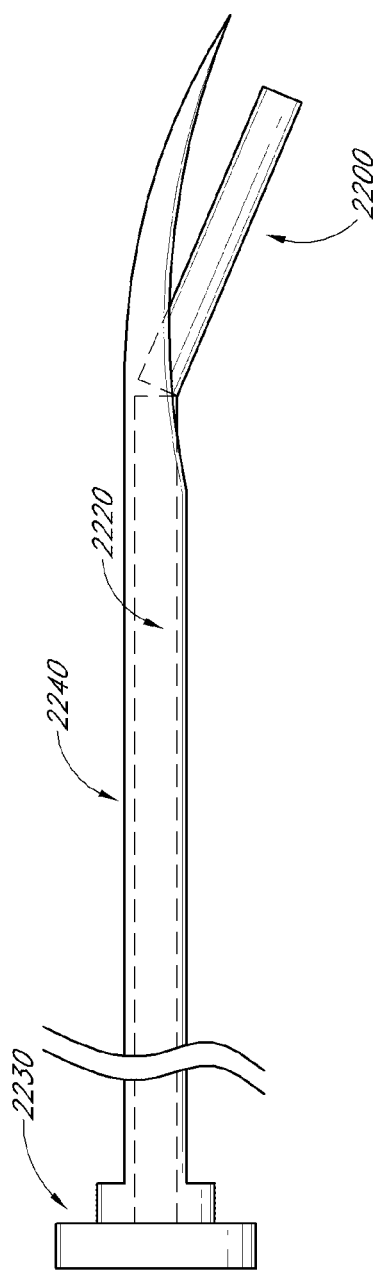
FIG. 24 illustrates another delivery device in accordance with embodiments disclosed herein.

Embodiments Illustrated in FIG. 24

FIG. 24 shows another embodiment of a system that can be used to perform a variety of methods or procedures. The shunt 2200 is deflected "downward" at an angle that parallels the suprachoroidal space. The depth of insertion can be determined by the length of the pushrod 2220, whose travel can be limited by the stop 2230. It is preferred that the pushrod ends at the proximal edge of the opening of the needle 2240. In this way, the shunt will not be pushed below the anterior surface of the ciliary muscle.

Figure 25:
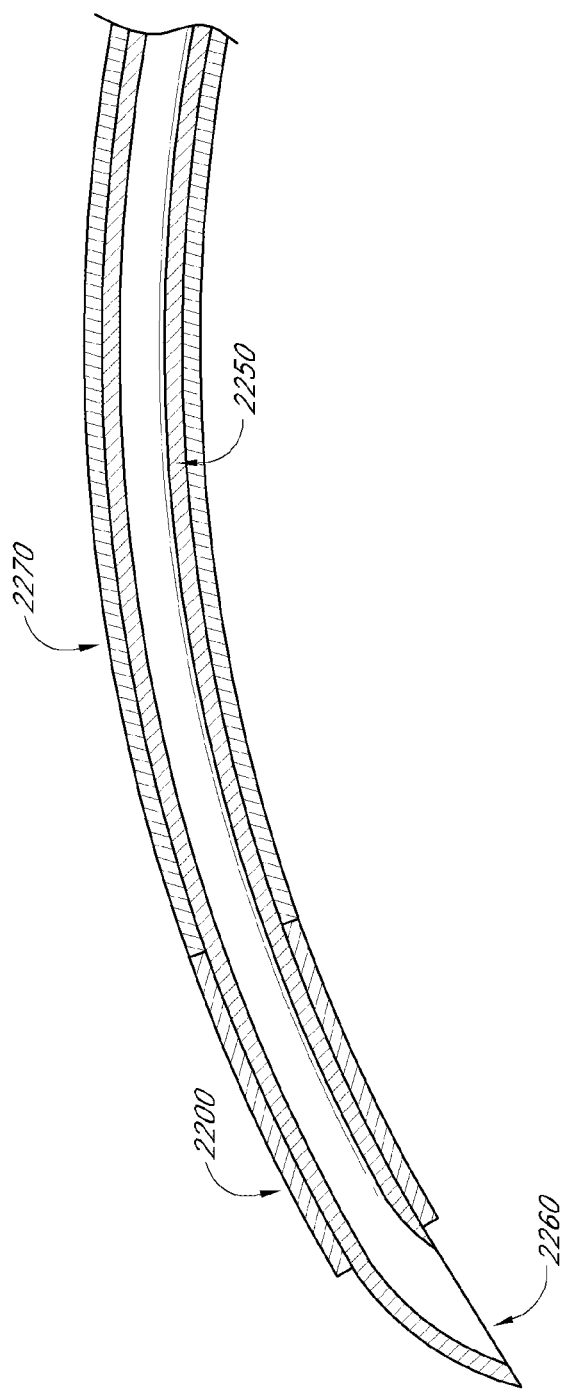
FIG. 25 illustrates a cross-sectional view of another drainage implant in accordance with embodiments disclosed herein.

Embodiments Illustrated in FIG. 25

FIG. 25 shows another embodiment of a system that can be used to perform a variety of methods or procedures. In the illustrated embodiment, the shunt 2200 is mounted on a curved or angled shaft 2250. The shaft 2250 can be tubular (as shown), or solid and the distal end 2260 can be sharpened. The shunt 2200 can be curved with approximately the same radius as the delivery device, so that the shunt can be relatively stiff and still slide along the shaft. In some embodiments, a pusher tube 2270 causes the shunt to slide distally along the shaft and be released. In operation in some embodiments, the sharpened end 2260 makes an incision in the fibrous tissue attaching the ciliary muscle and the sclera. In some embodiments, the distance between the sharpened tip 2260 and the distal end of the shunt determines how deeply the tissue may be incised. After making the cut, the operator can advance the pusher tube 2270 while holding the mounting shaft 2250 fixed. This action causes the shunt 2200 to be advanced into the incision. The distance of shunt advance can be determined by the length of the pusher tube 2270, whose travel can be limited by a stop, as depicted in FIG. 24.

Further embodiments of the invention incorporate injection of viscoelastic through the shunt or through the shaft 2250 in order to accomplish posterior dissection of the suprachoroidal tissue, thereby creating a volumetric chamber or reservoir for aqueous humor. In addition or in the alternative, therapeutic agents (e.g., a hyperosmatic agent) can be delivered into the suprachoroidal space through the shunt 2220 or through the shaft 2250.

Embodiments Illustrated in FIG. 26

FIG. 26 illustrates various embodiments of a cap 2280 for a shunt 2290 that is operable to drain fluid from the anterior chamber to the suprachoroidal space. The cap 2280 can include a tissue-piercing end 2300 and one or more outlet openings 2310. Each of the one or more outlet openings 2310 can communicate with at least one of the one or more lumens 2320. In some embodiments cap can have a conically shaped tip 2330 with a plurality of outlet openings 2310 disposed proximal of the tip's distal end. In other embodiments, the cap can have a tapered angle tip 2330. The tip 2330 can be sufficiently sharp to pierce eye tissue near the scleral spur of the eye. The tip also can be sufficiently blunt so as not to substantially penetrate scleral tissue of the eye. In some embodiments, the conically shaped tip 2330 facilitates delivery of the shunt to the desired location. In some embodiments, the cap 2280 has an outlet opening 2310 on a side surface to allow fluid flow. In the embodiment illustrated in FIG. 26a, there is a plurality of outlet openings 2310 on the conical surface of the cap. In the embodiment illustrated in FIG. 26b, the cap has a plurality of outlet openings 2310 on a side surface to allow fluid flow. The openings 2310 on the cap can facilitate fluid flow through the shunt. The openings 2310 may provide an alternate route for fluid flow which is beneficial in case the primary outflow portion of the shunt becomes blocked.

Embodiments Illustrated in FIG. 27

FIG. 27 shows another embodiment of a system that can be used to perform a variety of methods or procedures. The shunt 2350 illustrated in FIG. 27 has a portion 2360 which has an accordion-like structure. The accordion-like structure provides flexibility. FIG. 27(a) depicts the accordion-like portion 2360 in an expanded configuration. FIG. 27(b) depicts the accordion-like portion 2360 in a compressed configuration. FIG. 27(c) depicts the accordion-like portion 2360 in a curved or bended configuration.

Embodiments Illustrated in FIG. 28

Figure 28A:
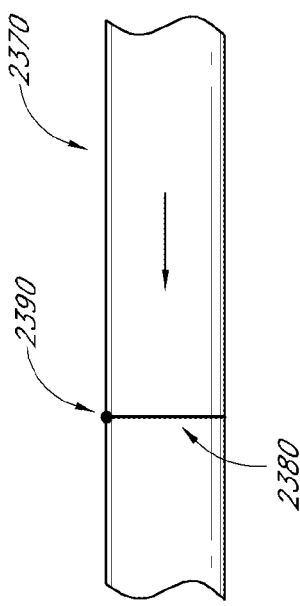
FIGS. 28A-B illustrates a reed-type valve in accordance with embodiments disclosed herein.
Figure 28B:
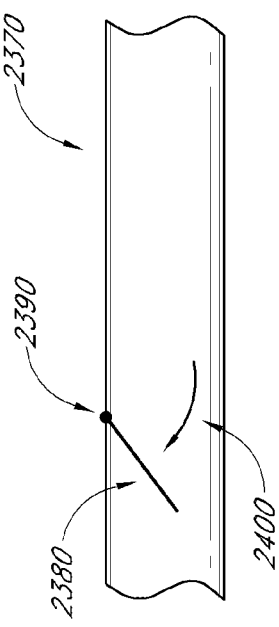

FIG. 28 illustrates another embodiment of a shunt 2370 that is operable to drain fluid from the anterior chamber to the suprachoroidal space. In the illustrated embodiment, the shunt 2370 has a reed-type valve 2380 to regulate flow. One end 2390 of the reed valve 2380 may be fixed to a portion of the shunt. The body of the reed valve 2380 is capable of being deflected 2400 in order to allow flow. The reed valve 2380 illustrated in FIG. 28a is shown in a closed configuration. Pressure from fluid in the anterior chamber can deflect the body of the reed valve 2380, thereby causing the valve to open, as depicted in FIG. 28b.

Figure 29:
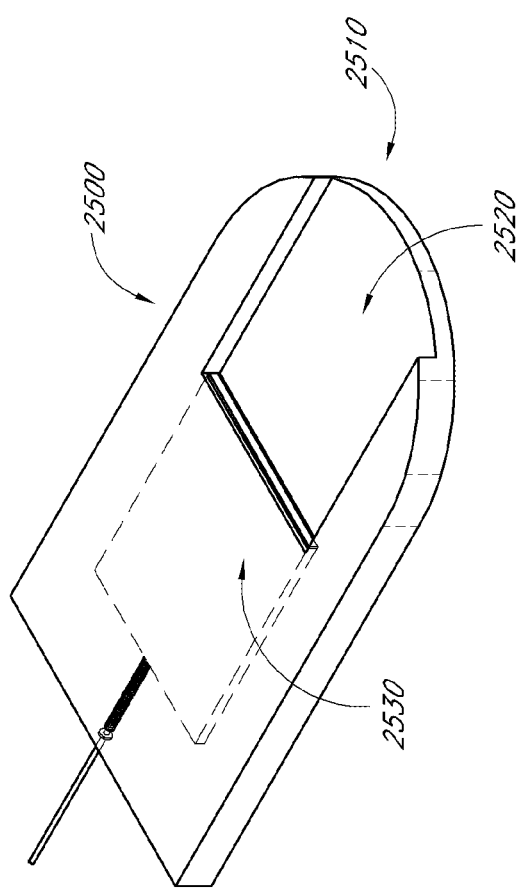
FIG. 29 illustrates another delivery device in accordance with embodiments disclosed herein.

Embodiments Illustrated in FIG. 29

FIG. 29 shows another embodiment of a system that can be used to perform a variety of methods or procedures. In the illustrated embodiment, a delivery instrument includes a distal end 2500 having a spatula shape. The spatula shape can have a sharpened forward edge 2510. The spatula shape can include a recess 2520 to contain the shunt. The recess can include a pusher 2530 or other suitable means to push out or eject the shunt.

Figure 30:
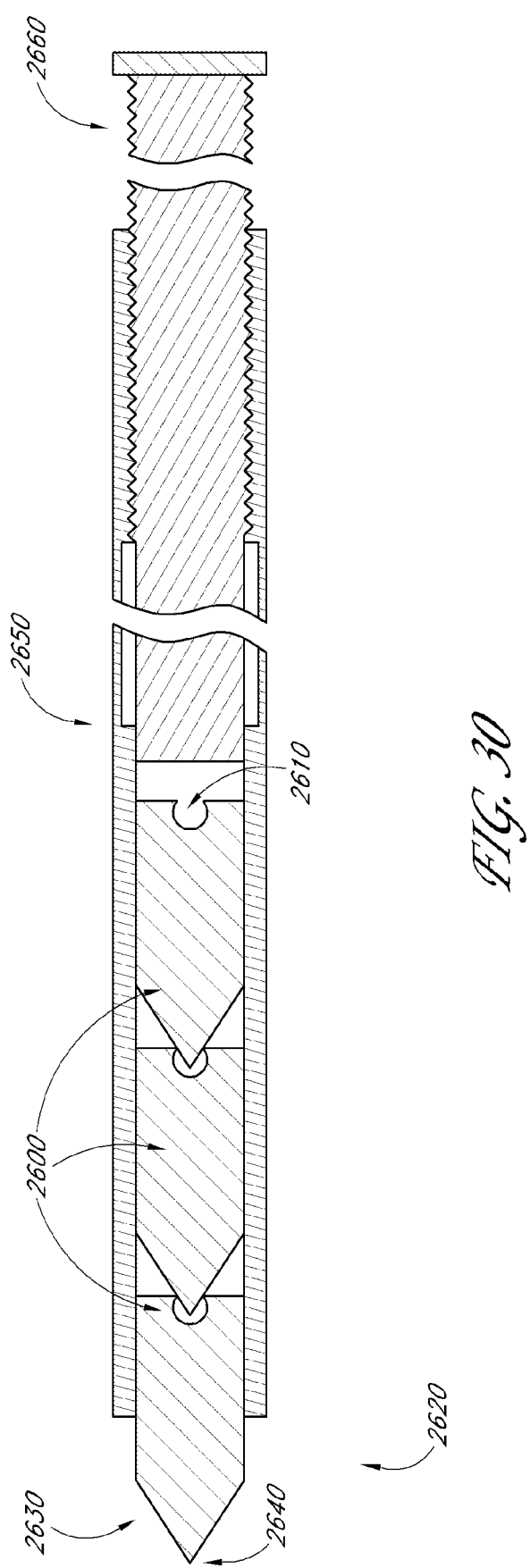
FIG. 30 illustrates a cross-sectional view of another embodiment of a delivery device.

Embodiments Illustrated in FIG. 30

FIG. 30 shows another embodiment of a system that can be used to perform a variety of methods or procedures. Multiple shunts 2600 are configured to be delivered during a single procedure. In the illustrated embodiment, the shunts 2600 (which are schematically shown) are arranged tandemly. The shunt can include a tip protector 2610 at one end. The tip protector 2610 can comprise a recess shaped to receive and protect, for example, the tip 2620 of an adjacent shunt. The tip protector 2610 is shaped to contact the sides 2630 of the generally conical tip while protecting the more tapered tip, or end 2640, from impact. The delivery instrument 2650 can include a pusher 2660 (e.g. a threaded push rod) or other suitable means to push out or eject each shunt 2600.

Figure 31:
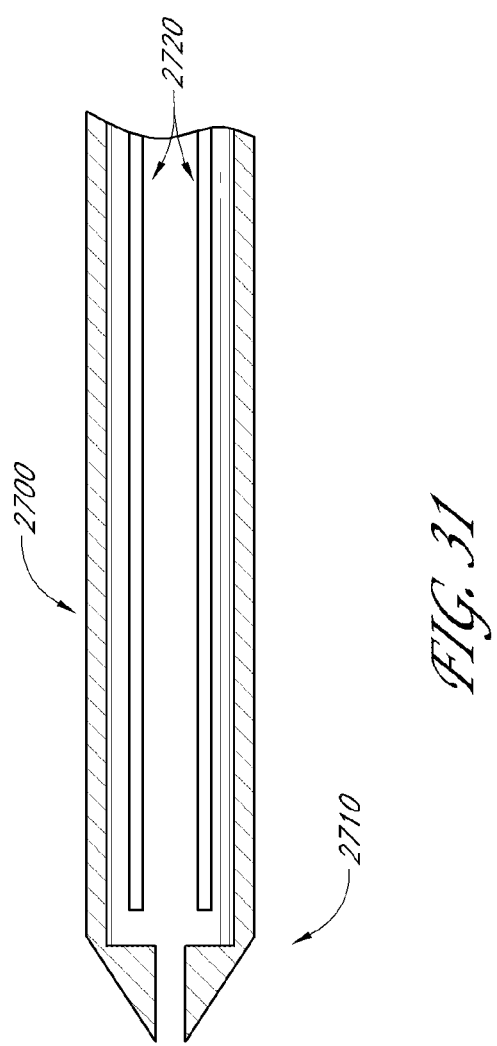
FIG. 31 illustrates a cross-sectional view of another embodiment of a delivery device.

Embodiments Illustrated in FIG. 31

FIG. 31 shows another embodiment of a system that can be used to perform a variety of methods or procedures. Delivery of the shunt 2700 is achieved by applying a driving force at or near the distal end 2710 of the shunt 2700 using, for example, a pusher 2720. The driving force can be a pushing force applied to the distal end 2710 of the shunt 2700. The delivery device alternatively can extend through or around the shunt to supply a pulling force to draw the shunt through tissue.

Figure 32:
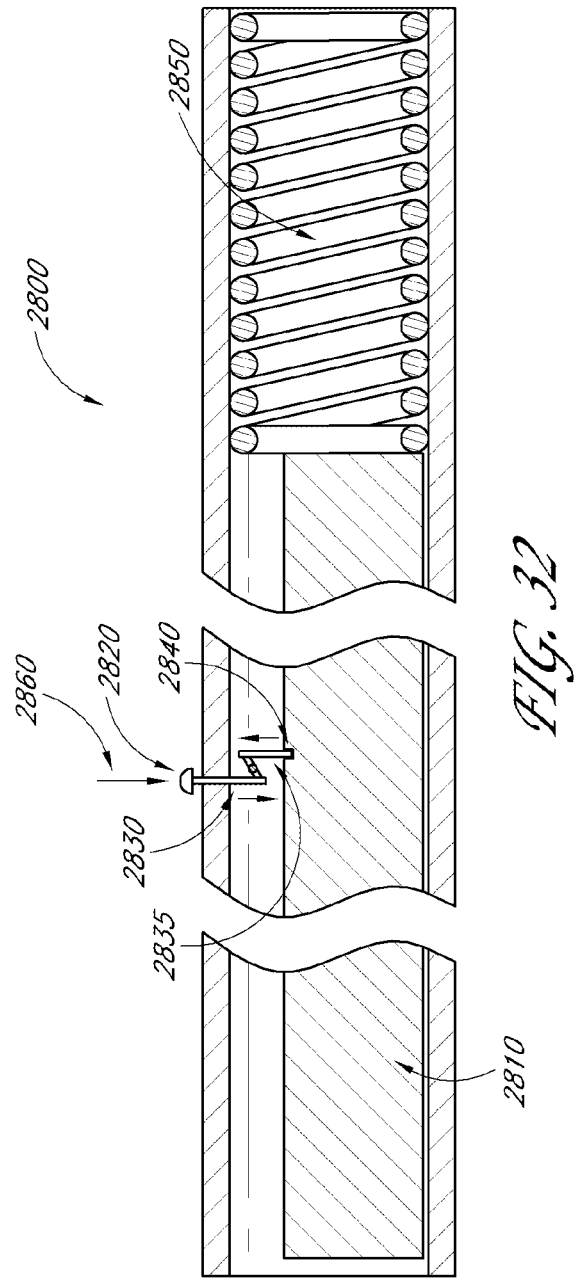
FIG. 32 illustrates a cross-sectional view of another embodiment of a delivery device.

Embodiments Illustrated in FIG. 32

FIG. 32 shows another embodiment of a system 2800 that can be used to perform a variety of methods or procedures. A spring-loaded pusher system 2800 can be used for delivery of a shunt. The spring-loaded pusher 2810 preferably includes a button 2820 operably connected to a hinged rod device 2830. The distal portion 2835 of the hinged rod device 2830 engages a depression 2840 in the surface of the pusher 2810, keeping the spring 2850 of the pusher 2810 in a compressed conformation. When the user pushes downwards 2860 on the button 2820, the distal portion 2835 of the hinged rod device 2830 is disengaged from the depression 2840, thereby allowing the spring 2850 to decompress, thereby advancing the pusher 2810 forward.

Figure 33:
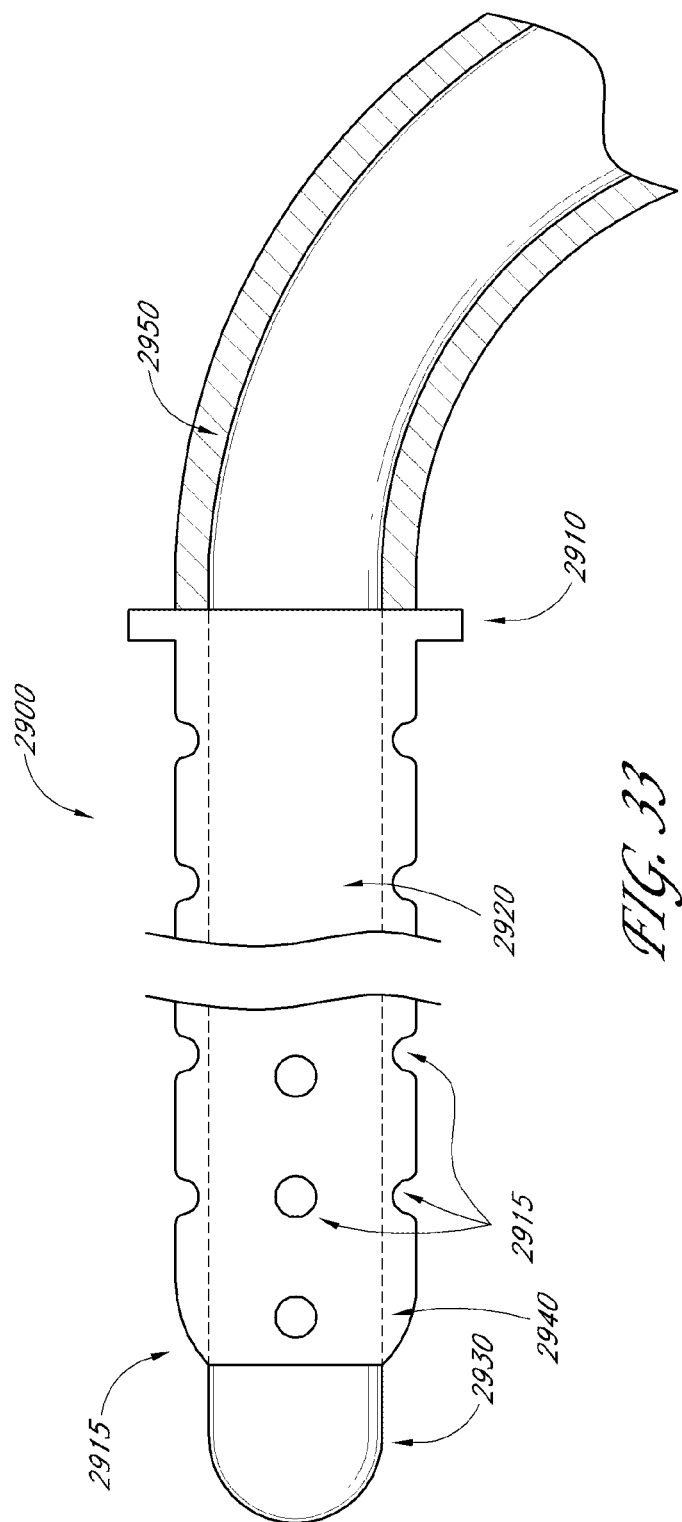
FIG. 33 illustrates a cross-sectional view of another embodiment of a delivery device and an associated shunt.

Embodiments Illustrated in FIG. 33

FIG. 33 shows another embodiment of a system that can be used to perform a variety of methods or procedures. In the illustrated embodiment, an over-the-wire system 2920 is used to deliver the shunt 2900. The shunt 2900 can have a generally rounded distal portion 2915 at the distal end. The radius of the distal portion can be about 70 to about 500 microns. The distal portion 2915 can gradually increase in cross-sectional size towards the proximal direction, preferably at a generally constant taper or radius or in a parabolic manner as shown.

In some embodiments, the implant comprises one or more openings 2905 communicating with an interior chamber, or lumen, within the implant. Preferably, the edges of the openings are rounded as shown. In addition or in the alternative, the implant can include other exterior surface irregularities (e.g., annular grooves) to anchor the implant, as described above.

In some embodiments the shunt can have a flange 2910 at a proximal portion of the implant. Preferably, the flange has sharp edges and corners as shown. The sharp edges and corners tend to inhibit cell proliferation near the influent end of the implant.

The wire or similar elongated structure 2920 can function as a trocar. Preferably, the wire 2920 is self-trephinating. The radius of the tip of the distal portion 2930 of the wire 2920 can be about 10 to about 500 microns. In some embodiments, the radius of the tip of the distal portion 2930 of the wire 2920 can be about 70 to about 200 microns. The distal portion 2930 of wire 2920 can increase in cross-sectional size towards the proximal direction. In some embodiments, the increase can be in a parabolic manner. In the depicted embodiment, the wire 2920 has a distal portion 2930 having a gradual increase in cross-sectional size in a parabolic manner towards the proximal direction. The wire 2920 can have a rounded distal tip of the distal portion 2930. In other embodiments, the distal portion can be tapered. The wire can be superelastic, flexible, or relatively inflexible with respect to the shunt. The wire can be pre-formed to have a certain shape. The wire can be curved. The wire can have shape memory, or be elastic. In some embodiments, the wire is a pull wire. The wire can be a steerable catheter.

In some embodiments, a pusher 2950 can used in conjunction with the wire 2920 to aid in delivery of the shunt 2900. The pusher 2950 can be used to hold the shunt 2900 in place as the wire 2920 is withdrawn proximally after the shunt 2900 has been delivered to a desired location.

The pusher 2950, trocar 2920 and implant 2900 preferably are sized to fit and move (e.g., slide) within an outer sheath or needle. The needle preferably includes a sharpened distal end to penetrate tissue (e.g., corneal tissue) when accessing the anterior chamber of the eye.

Figure 35:
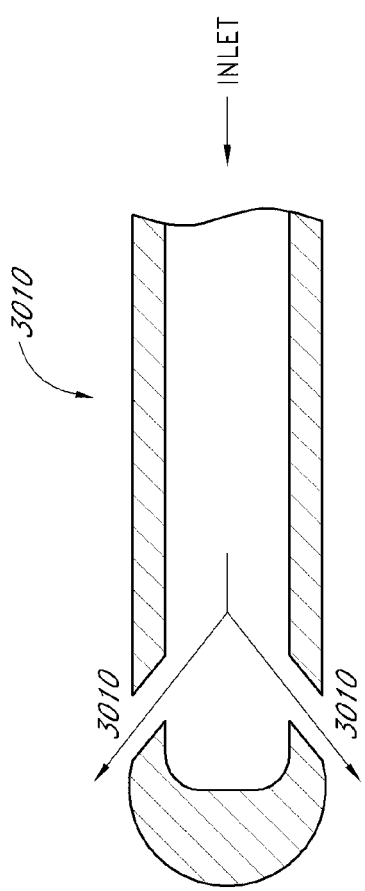
FIG. 35 is a cross-sectional view of another embodiment of a shunt with side ports.
Figure 36:
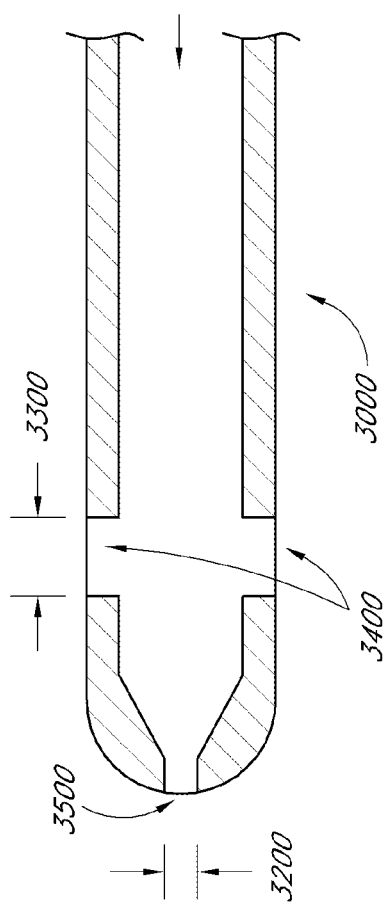
FIG. 36 is a cross-sectional view of another embodiment of a shunt with side ports.

Embodiments Illustrated in FIGS. 34-36

FIGS. 34-36 illustrate other embodiments of a shunt that is operable to conduct fluid from the anterior chamber to the suprachoroidal space. In the embodiments illustrated in FIGS. 34A, 34B and 35, the shunt 3000 has an outflow configuration 3010 wherein the flow exits normal (+/−90°) from the axis of the shunt through a side port exit hole 3020. This outflow configuration can prevent adhesion and/or encapsulation of the tissues that make up the supraciliary or suprachoroidal space (e.g., choroid and sclera and any other membranes within) by, for example, the fluid pressure created, and/or a rinsing effect. As such, the outflow pathway is kept clear and unobstructed. In addition, in this outflow configuration, the flow can exit and directly impinge the tissues that form the uveoscleral outflow pathway. This flow can push and hold the surrounding tissue away form the stent, thereby preventing tissue adhesion to the shunt 3000 at the location of the fluid path. The flow can also help to create a stenting effect, i.e., holding the space open and enlarging. In some embodiments, the stenting can facilitate absorption into the choroid and/or the sclera by increasing the contact area between the pool of aqueous humor and the tissues. The side port exit holes 3020 also can prevent tissues and cells from accumulating in an axial hole during the insertion operation, i.e., the scraping/snowplowing of cells/tissues that could get lodged in the tip and block flow.

In the embodiment illustrated in FIG. 35, the shunt 3000 has an outflow configuration 3100 wherein the flow exits the device not axially, nor at a 90° angle to the device main axis, but at an angle that bisects the two options, i.e., 30-60°. This outflow configuration can help to prevent tissue adhesion and provide the other benefits described above. In addition, this outflow configuration allows the flow to exit the shunt without the slowdown that occurs when it is turned at a 90° angle. That is, the configuration presents a less restrictive flow path. This outflow configuration consequently can provide a greater opportunity for the flow to be directed deeper into the suprachoroidal space.

The outflow configuration shown in FIGS. 34A, 34B and 35 can be combined with one or more axial outlets, as shown in FIG. 36. In the embodiment illustrated in FIG. 36, the shunt 3000 has a combination of axial 3200 and side port 3300 flow. In this embodiment, the relative sizes of the ports 3400, 3500 can be varied to achieve the correct balance between the two flow directions. For example, the axial flow lumen can be sized down so that the side port openings 3400 receive an adequate amount of flow to realize the advantages of side port flow 3300 without sacrificing axial flow 3200 and maximal flow penetration deep into the uveoscleral outflow pathway. In other words, each side port opening 3400 has a size 3300 larger than the size 3200 of the axial 3300 port 3500. Alternatively, in some applications, the axial port 3500 can be larger than one or more, or all of the side port 3400.

The shunt aspects described in connection with FIGS. 34-36 can be incorporated into other embodiments of the shunt, such as the embodiment depicted in FIG. 33.

Figure 37:
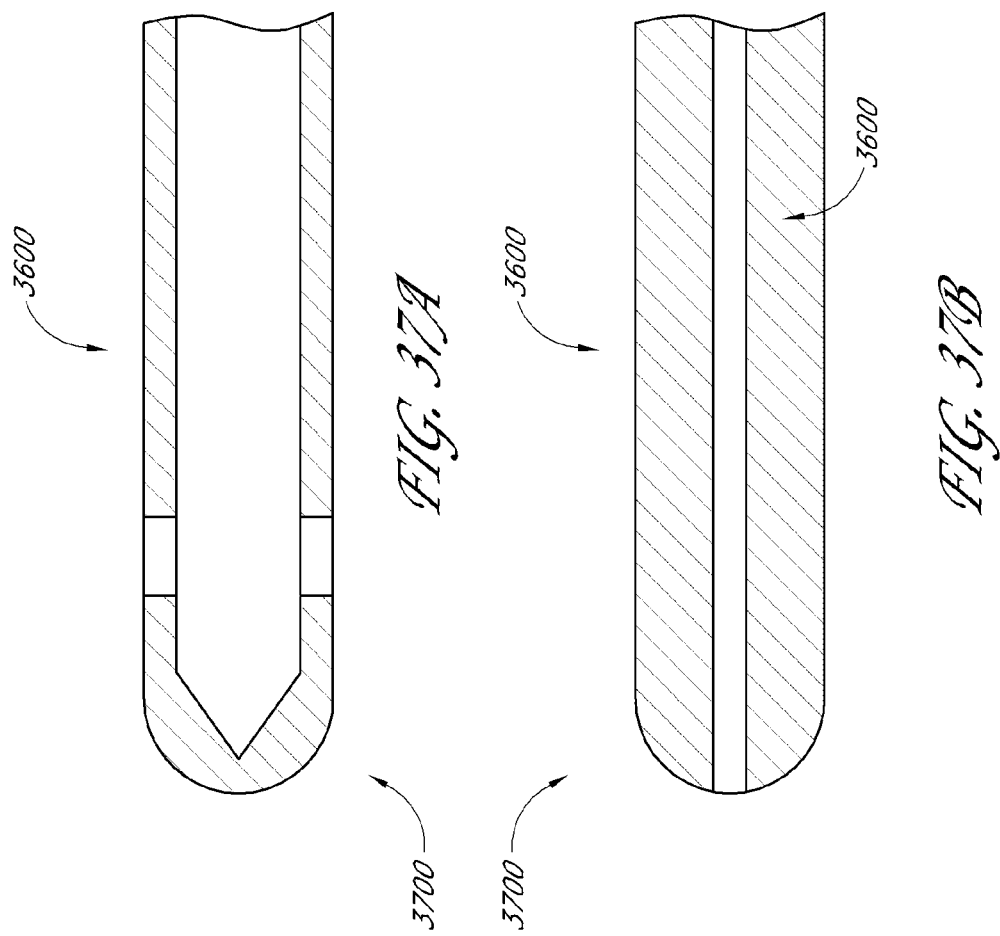
FIGS. 37A and 37B illustrate cross-sectional views of other drainage implants in accordance with embodiments disclosed herein.

Embodiments Illustrated in FIGS. 37A and 37B

FIGS. 37A and 37B show another embodiments of a system that can be used to perform a variety of methods and procedures. The shunt 3600 illustrated in these figures has a solid and rounded tip with a central lumen 3800 (as illustrated in FIG. 37A) or without a central lumen (as illustrated in FIG. 38B).

Figure 38:
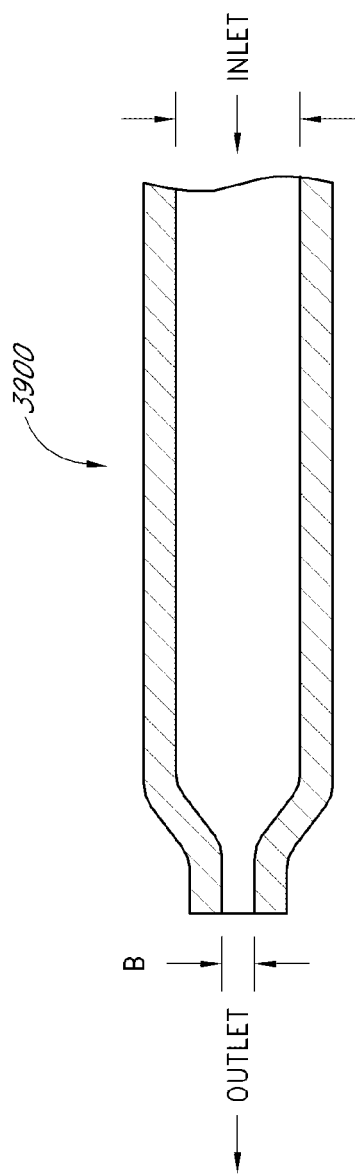
FIG. 38 illustrates a cross-sectional view of another drainage implant in accordance with embodiments disclosed herein.

Embodiments Illustrated in FIG. 38

FIG. 38 shows another embodiment of a system that can be used to perform a variety of methods or procedures. The shunt 3900 illustrated in FIG. 37 has a reduced diameter B at the point where the fluid exits the stent, compared with the inlet orifice diameter A. The reduced diameter B can result in an increased fluid velocity $V_B$, compared to the fluid inlet velocity $V_A$. The increased fluid velocity can help to keep tissue at bay, thereby preventing adhesion to the shunt. The increased fluid velocity can also create space for absorption of fluid into the choroid and sclera. The increased fluid velocity can also cause deeper penetration of the fluid once it exits the shunt.

Figure 39:
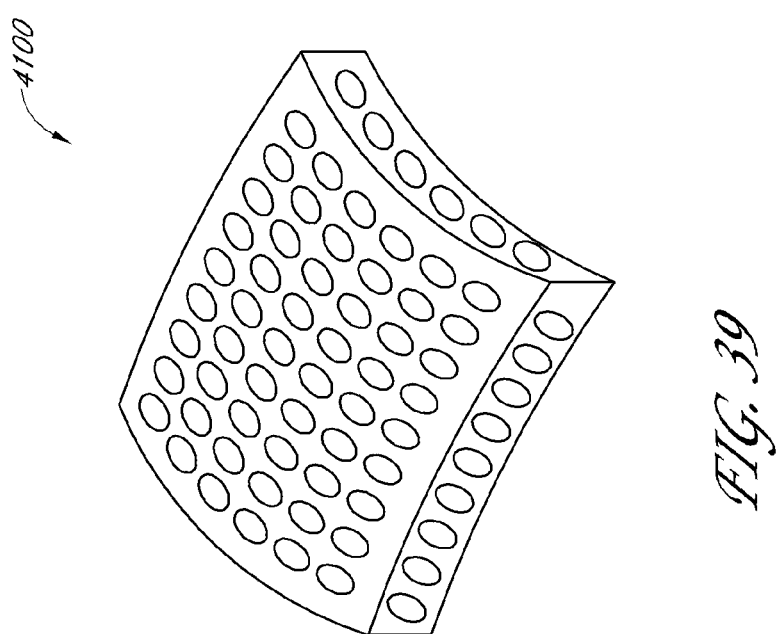
FIG. 39 is a perspective view of an implant configured in accordance with another embodiment of the present invention.

Embodiments Illustrated in FIGS. 39 and 40A-B

FIGS. 39, 40A and 40B shows another embodiment of a system that can be used to perform a variety of methods or procedures. A matrix, or grating 4100 can be positioned within the uveoscleral outflow pathway to create, and hold open a space between the ciliary muscle bundlres, or the choroid and the sclera, into which fluid can flow. The grating 4100 can effectively decrease or essentially eliminate the resistance that the fluid would encounter upon entering the uveoscleral outflow pathway from a single or double entry point from the anterior chamber, and establish open fluid communication, or, in longer embodiments, contact to a large surface area of choroid and/or sclera for absorption and dissipation. The grating 4100 can be made from a number of biocompatible materials such as, for example, metals like gold, platinum, tantalum, titanium, etc., or from a biocompatible polymer such as silicone, PMMA, polyimide, polyether sulfone (PES), styrene-b-isobutylene-b-styrene (SIBS), ceramic, or from a combination of materials, such as a coating, plating, or coextrusion of one of the mentioned materials with another one of the mentioned or other materials. The grating 4100 can be separate, or integral with a shunt that establishes a patent opening from the anterior chamber 4105 to the suprachoroidal space 4110. As shown in FIG. 40B, the grating 4100 can be injected or otherwise placed through a small opening such as a tube 4120 and unfold or otherwise expand once in the suprachoroidal space so that it can be delivered ab interno. In other embodiments, the grating can be placed ab externo. The grating 4100 can also include one or more therapeutic agent, which is carried by, embedded within, integrated with and/or coated on the grating 4100.

Embodiments Illustrated in FIGS. 41A-J

FIGS. 41A-J show other embodiments of a system that can be used to perform a variety of methods or procedures. The shunts 4200 illustrated in FIGS. 41A-J include a retention feature(s) to engage the fibrous muscle adhesion 4210 (FIG. 41A) that attaches the choroid to the sclera at its furthest anterior extent of the choroid. The feature can help prevent the stent from moving once implanted. The feature can also give the surgeon tactile feedback as to the ideal axial positioning of the device. Such a feature can be in the form of a circumferential groove, a protruding anchor, a flange, etc.

Figures 41D, 41F:
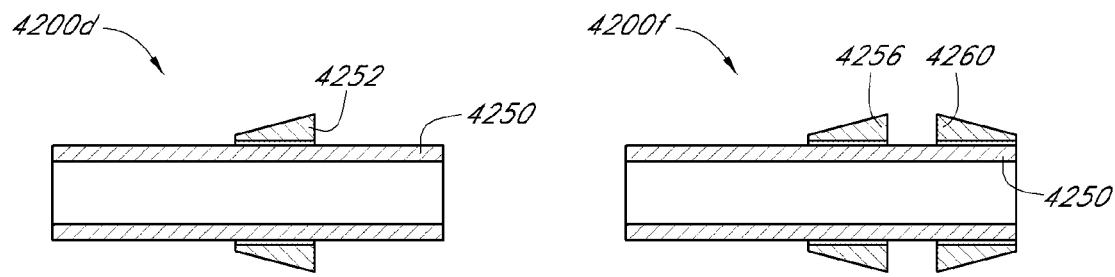
Figure 41E:
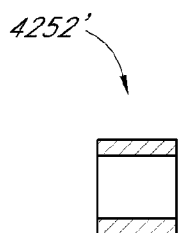
Figure 41G:
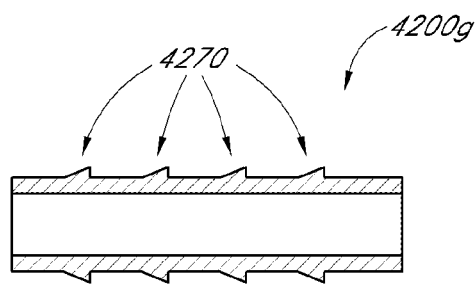
Figure 41H:
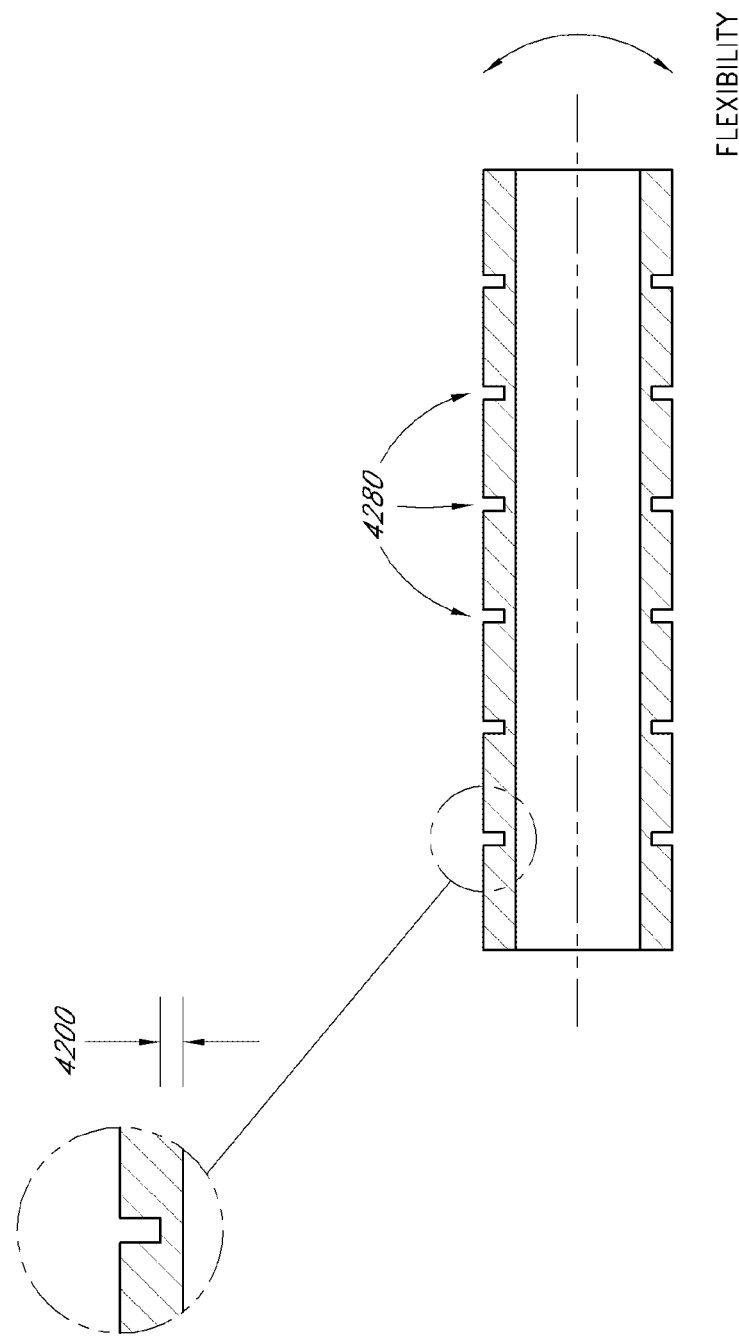

The shunt 4200a illustrated in FIG. 41A includes an annular barb 4215 that projects from the outer surface of the shunt 4200a. The shunt 4200b illustrated in FIG. 41B includes a feature formed by wire 4232 which is placed through a hole 4230 in the shunt 4232. Preferably, the wire is preformed and elastic, which allows it to fold down during implantation using a delivery device. The shunt 4200c illustrated in FIG. 41C includes two annular barbs 4234, 4236 that are arranged back-to-back. As such, the barbs 4234, 4236 form an annular groove about the shunt 4200c. FIG. 41D illustrates another embodiment of a shunt 4200d with an annular barb 4252. In this embodiment, the barb 4252 is formed apart from a tubular body of the implant 4250 and is attached thereto with suitable mechanical fasteners (e.g., detents and grooves) or chemical adhesives (e.g., cyanoacrylate). FIG. 41E illustrates another embodiment of the barb 4252' with a cylindrical shape. FIG. 41F illustrates an embodiment of a shunt 4200f that includes a plurality of barbs 4256, 4260 that are arranged to form an annular groove on the exterior of the shunt 4200f. FIG. 41G illustrates yet another embodiment of a shunt 4200g with a plurality of annular ribs 4270 formed on an exterior surface of the shunt 4200g. In some embodiments, the retention feature(s) may be cut deep enough to make the body of a shunt made from plastic or metal flexible enough for insertion through bent tube, such as a cannula, and to conform to anatomy after placement. FIG. 41H shows a plurality of retention features 4280 on the body of a shunt 4200H which have been sized to weaken the wall of the shunt and to provide flexibility of the tube. Any of these retention features can be used with the above-described embodiments of shunts and delivery devices.

Embodiments Illustrated in FIGS. 42A-D

Figure 42A:
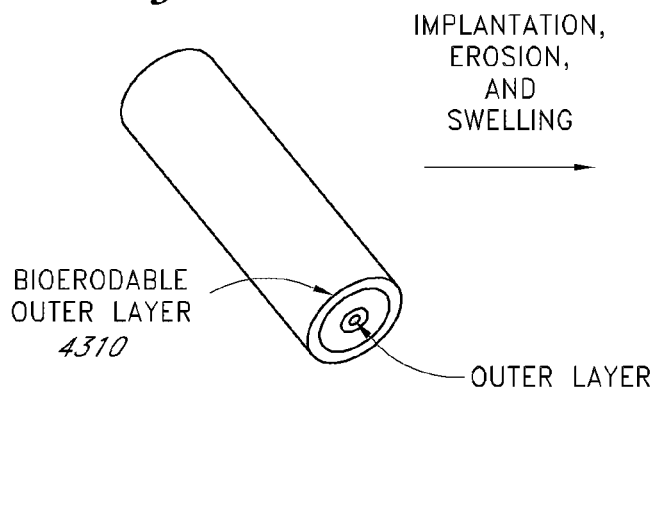
FIGS. 42A to 42D illustrate cross-sectional views of other drainage implants in accordance with embodiments disclosed herein.
Figure 42B:
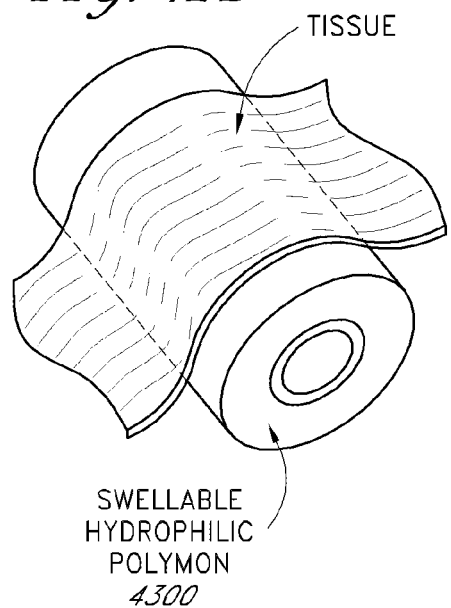
Figure 42C:
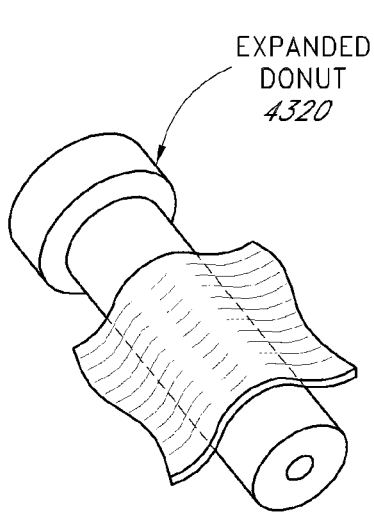
Figure 42D:
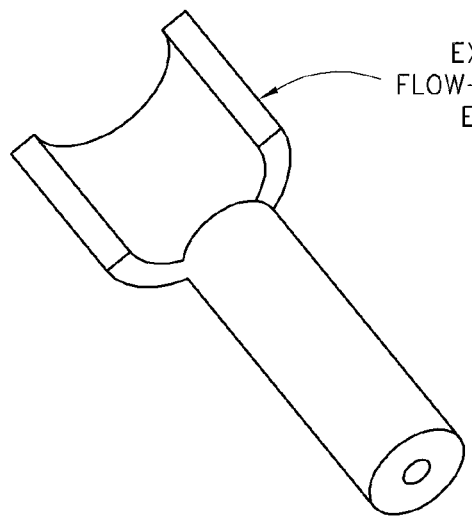

FIGS. 42A-D show other embodiments of a system that can be used to perform a variety of methods or procedures. The shunts illustrated in FIGS. 42A-D are made of a swellable hydrophilic polymer 4300. The swellable hydrophilic polymer can be, for example, swellable hydrophilic aliphatic polyurethane. Swelling of the polymer after insertion of the shunt can create a tight fit in the tissue, as shown in FIGS. 42A and 42B. The swellable material can be applied by, for example, dip coating, spray coating, or coextrusion to a core tubular structure comprised of a nonswellable polymeric or metal or ceramic material. Alternatively, the stent can be molded or extruded from the swellable hydrophilic material. In either of these cases, the outer surface can be covered by a thin layer of a biodegradable polymer 4310 such as polylactic acid, as shown in FIG. 42A. The layer of biodegradable polymer can prevent the swellable polymer from swelling until after it is implanted. A layer of viscoelastic may also accomplish this purpose. The swellable material may be formed as one or two "donuts" 4320 to further enhance retention of the stent, and prevention of anterior or posterior migration. The swellable material may also be designed to form a flow-dispersing component upon swelling.

Variations

In some embodiments, the shunt can facilitate delivery of a therapeutic agent. The therapeutic agent can be, for example, heparin, TGF-beta, an intraocular pressure-lowering drug, and an anti-proliferative agent. In some embodiments, the therapeutic agent is introduced concurrently with the delivery of the shunt to the eye. The therapeutic agent can be part of the shunt itself. For example, the therapeutic agent can be embedded in the material of the shunt, or coat at least a portion of the shunt. The therapeutic agent may be present on various portions of the shunt. For example, the therapeutic agent may be present on the distal end of the shunt, or the proximal end of the shunt. The shunt can include combination of therapeutic agents. The different therapeutic agents can be separated or combined. One kind of therapeutic agent can be present at the proximal end of the shunt, and a different kind of therapeutic agent can be present at the distal end of the shunt. For example, an anti-proliferative agent may be present at the distal end of the shunt to prevent growth, and a growth-promoting agent may be applied to the proximal end of the shunt to promote growth. In some embodiments, the therapeutic agent is delivered through the implant to the desired location in the eye, such as the uveoscleral outflow pathway. In some embodiments, the therapeutic agent is delivered to the uveoscleral outflow pathway in combination with a therapeutic agent delivered via trans pars plana vitrectomy, thereby delivering a therapeutic agent to both sides of the retina. In some embodiments, the shunt can improve access of topical medication to the posterior uvea. In some embodiments, the shunt is used to delivery a topical medication to treat a chorio-retinal disease.

If desired, more than one shunt of the same or different type may be implanted. For example, the shunts disclosed herein may be used in combination with trabecular bypass shunts, such as those disclosed in U.S. Patent Publication 2004/0050392 (Appendix A), and those described in U.S. Patent Publication 2005/0271704, filed Mar. 18, 2005, the entirety of which is incorporated herein by reference and made a part of this specification and disclosure. Additionally, implantation may be performed in combination with other surgical procedures, such as cataract surgery. All or a portion of the shunt may be coated, e.g. with heparin, preferably in the flow path, to reduce blood thrombosis or tissue restenosis.

If desired, a multiplicity of shunts having different flow capacities and/or lumen sizes may be implanted. For example, a single "large" lumen stent can be implanted first, and subsequent, depending on the pressure response to the first stent, a second can be added with potentially smaller flow capacity in order to "fine tune" the desired IOP. For example, the IOP of a first patient can safely be brought down to approximately 12-18 mm Hg, and once the flow capacity of the first stent is matched with the IOP reduction, a calculation can be made as to what additional outflow is required to achieve target pressures of, for example, approximately 8-12 mmHg. An appropriately sized stent can be added to accomplish the target pressure. Both stents can be proactively added at the same time based on calculated outflow requirements. Alternatively, the stents can be added sequentially as described above based on the measured effect of the first stent.

While certain embodiments of the disclosure have been described, these embodiments have been presented by way of example only, and are not intended to limit the scope of the disclosure. Indeed, the novel methods, systems, and devices described herein may be embodied in a variety of other forms. For example, embodiments of one illustrated or described shunt can be combined with embodiments of another illustrated or described shunt. Moreover, the shunts described above can be utilized for other purposes. For example, the shunts can be used to drain fluid from the anterior chamber to other locations of the eye or outside the eye. Furthermore, various omissions, substitutions and changes in the form of the methods, systems, and devices described herein may be made without departing from the spirit of the disclosure.

What is claimed is:

1. A system for treating an ocular disorder, the system comprising:
   a shunt made of a flexible material, the shunt comprising:
      a proximal end, a distal end, and a lumen extending from the proximal end to the distal end, a radius of a tip of the distal end being sufficiently blunt so that as the shunt is advanced into a supraciliary or suprachoroidal space of an eye, the shunt slides along an interior wall of a sclera without penetrating the sclera; and
      radial extensions located on an exterior surface of the shunt to resist extrusion of the shunt from the supraciliary or suprachoroidal space after insertion of the shunt into the supraciliary or suprachoroidal space; and
   a delivery instrument configured to deliver the shunt, the delivery instrument comprising a body with an open distal end and a plurality of members being at least partially disposed within the body and being longitudinally moveable relative to each other to aid in delivery of the shunt, the plurality of members comprising:
      a flexible wire being movable within the lumen of the shunt; and
      a pusher circumferentially surrounding a proximal portion of the flexible wire and adapted to block a proximal movement of the shunt when the flexible wire is withdrawn through the proximal end of the shunt.

2. The system of claim 1, wherein a curvature of a distal portion of the flexible wire has a radius between 10 millimeters and 30 millimeters.

3. The system of claim 1, wherein the flexible material is polyethersulfone.

4. The system of claim 1, wherein the shunt has a length between 1.5 millimeters and 5 millimeters.

5. The system of claim 1, wherein the flexible wire has a rounded distal end.

6. A system for treating an ocular disorder, the system comprising:
   a shunt made of a flexible material, the shunt comprising:
      a proximal end, a distal end, and a lumen extending from the proximal end to the distal end, a radius of a tip of the distal end being between 70 microns to 200 microns, the tip providing an edge against which the shunt abuts a sclera and slides along an interior wall of the sclera as the shunt is advanced into a supraciliary or suprachoroidal space of an eye; and
      radial extensions located on an exterior surface of the shunt to resist extrusion of the shunt from the supraciliary or suprachoroidal space after insertion of the shunt into the supraciliary or suprachoroidal space;
   a delivery instrument configured to deliver the shunt, the delivery instrument comprising a body with an open distal end and a plurality of members being at least partially disposed within the body and being longitudinally moveable relative to each other to aid in delivery of the shunt, the plurality of members comprising:
      a flexible wire movable within the lumen of the shunt; and
      a pusher circumferentially surrounding a proximal portion of the flexible wire, the flexible wire being movable relative to the pusher, the pusher sized to block a movement of the shunt when the proximal portion is withdrawn from the proximal end of the shunt.

7. The system of claim 6, wherein a curvature of a distal portion of the flexible wire has a radius between 10 millimeters and 30 millimeters.

8. The system of claim 6, wherein the shunt has a length between 1.5 millimeters and 5 millimeters.

9. The system of claim 6, wherein the flexible material is polyethersulfone.

10. The system of claim 6, wherein the shunt has a cross-sectional size between 0.1 mm and 1.0 mm.

11. The system of claim 6, wherein the shunt has a cross-sectional size between 0.3 mm and 0.4 mm.

12. A system for treating an ocular disorder, comprising:
   a shunt made of a flexible material, the shunt comprising:
      a proximal end, a distal end, and a lumen extending from the proximal end to the distal end, a tip of the distal end providing an edge against which the shunt abuts a sclera of an eye, the edge adapted to slide along an interior wall of the sclera without penetrating the sclera as the shunt is advanced into a supraciliary or suprachoroidal space of the eye; and
      a flange at the proximal end of the shunt, the flange having a distal-most face and an outer surface that extends along and circumferentially surrounds the lumen, the flange further comprising a sharp corner that circumferentially surrounds the lumen and joins the distal-most face to the outer surface; and
   a delivery instrument configured to deliver the shunt, the delivery instrument comprising a body with an open distal end and a plurality of members being at least partially disposed within the body and being longitudinally moveable relative to each other to aid in delivery of the shunt, the plurality of members comprising:
      a flexible wire being movable within the lumen of the shunt; and
      a pusher circumferentially surrounding a proximal portion of the flexible wire and adapted to block a proximal movement of the shunt when the flexible wire is withdrawn through the proximal end of the shunt.

13. The system of claim 12, wherein a curvature of a distal portion of the flexible wire has a radius between 10 millimeters and 30 millimeters.

14. The system of claim 12, wherein the shunt has a length between 1.5 millimeters and 5 millimeters.

15. The system of claim 12, wherein the flexible material is polyethersulfone.

16. The system of claim 12, wherein the shunt has a cross-sectional size between 0.1 mm and 1 mm.

17. The system of claim 12, wherein the shunt has a cross-sectional size between 0.3 mm and 0.4 mm.

18. A method for implanting a drainage implant ab interno in an eye to divert aqueous humor from an anterior chamber to a suprachoroidal space, the method comprising:
   inserting a delivery instrument into the anterior chamber of the eye through an opening in the eye;
   transporting the drainage implant through the anterior chamber to an anterior chamber angle of the eye;
   abutting a portion of a distal tip of the drainage implant against a sclera;
   sliding the distal tip of the drainage implant along an interior wall of the sclera to advance the drainage implant into a uveoscleral outflow pathway while avoiding penetrating the interior wall of the sclera; and
   positioning the drainage implant within the uveoscleral outflow pathway such that an inflow portion of the drainage implant is in the anterior chamber and an outflow portion is in the suprachoroidal space.

19. The method of claim 18, further comprising withdrawing a flexible wire from a lumen of the drainage implant while maintaining a position of the outflow end in the suprachoroidal space.

20. The method of claim 18, further comprising advancing the shunt through an incision in a tissue that lies posterior to a scleral spur.

\* \* \* \* \*